US006797488B1

(12) United States Patent
Sukhatme

(10) Patent No.: US 6,797,488 B1
(45) Date of Patent: Sep. 28, 2004

(54) METHODS OF PRODUCING ANTI-ANGIOGENIC PROTEINS

(75) Inventor: Vikas P. Sukhatme, Newton Center, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/589,483

(22) Filed: Jun. 7, 2000

Related U.S. Application Data

(63) Continuation of application No. PCT/US98/25892, filed on Dec. 8, 1998.
(60) Provisional application No. 60/108,536, filed on Nov. 16, 1998, provisional application No. 60/082,663, filed on Apr. 22, 1998, and provisional application No. 60/067,888, filed on Dec. 8, 1997.

(51) Int. Cl.⁷ .............................................. C12P 21/02
(52) U.S. Cl. ...................... 435/69.1; 435/69.6; 435/483
(58) Field of Search .............................. 435/69.1, 69.6, 435/483, 172.3; 530/350

(56) References Cited

U.S. PATENT DOCUMENTS 5,854,205 A    12/1998   O'Reilly et al.
6,057,122 A  *  5/2000   Davidson

FOREIGN PATENT DOCUMENTS

| WO | WO 95/29242 | 11/1995 |
| WO | WO 96/35774 | 11/1996 |
| WO | WO 97/15666 | 5/1997 |
| WO | wo97/15666 | * 5/1997 |
| WO | WO 98/54217 | 12/1998 |
| WO | WO 99/16889 | 4/1999 |
| WO | WO 99/26480 | 6/1999 |
| WO | WO 99/29855 | 6/1999 |
| WO | WO 99/29856 | 6/1999 |
| WO | WO 99/29878 | 6/1999 |
| WO | WO 00/20610 | 4/2000 |

OTHER PUBLICATIONS

Paivi et al. Cloning of mouse type xv collagen sequences and mapping of the corresponding gene to 4B1–3 Genomics 45, 31–41 1997.*
O'Reilly, et al., "Endostatin: An Endogenous Inhibitor of Angiogenesis and Tumor Growth", *Cell* 88:277–285 (1997).
Ständker et al., "Isolation and Characterization of the Circulating Form of Human Endostatin", *FEBS*:129–133 (1997).
Dhanabal, et al., Endostatin: Yeast Production, Mutants, and Antitumor Effect in Renal Cell Carcinoma, *Cancer Research*, 59:189–197 (1999).

Hohenester, et al., "Crystal Structure of the Angiogenesis Inhibitor Endostatin at 1.5 A Resolution", *EMBO Journal*:17(6):1656–1664 (1998).
Boehm, et al., "Zinc–Binding of Endostatin is Essential for Its Antiangiogenic Activity", *Biochemical and Biophysical Research Communication*, 252:190–194 (1998).
Boehm, et al., "Disruption of the KEX1 Gene in Pichia Pastoris Allows Expression of Full–Length Murine and Human Endostatin", *Yeast* 15:563–572 (1999).
Ding et al., "Zinc–Dependent Dimers Observed in Crystals of Human Endostatin", *Proc. Natl. Acad. Sci.*, 95:10443–10448 (1998).
Sasaki, et al., "Structure Function and Tissue Forms of the C–Terminal Globular Domain of Collagen XVIII Containing the Angiogenesis Inhibitor Endostatin", *EMBO Journal* 17(15):4249–4256 (1998).
Dhanabal, et al., "Cloning, Expression, and In Vitro Activity of Human Endostatin", *Biochemical and Biophysical Research Communications*, 258:345–352 (1999).
Sim et al., "A Recombinant Human Angiostatin Protein Inhibits Experimental Primary and Metastatic Cancer", *Cancer Research* 57:1329–1334 (1997).
Rehn et al., "Primary Structure of the α1 Chain of Mouse Type XVIII Collagen, Partial Structure of the Corresponding Gene, and Comparison of the α1 (XVIII) Chain with Its Homologue, the α1 (XV) Collagen Chain", *The Journal of Biological Chemistry* 269(19):13929–13935 (1994).
Ramchandran, et al., "Antiangiogenic Activity of Restin, NC10 Domain of Human Collagen XV: Comparison to Endostatin", *Biochemical and Biophysical Research Communications* 255:735–739 (1999).
Griparic, et al., "Cloning and Expression of Chicken CLIP–170 and Restin Isoforms", *Gene* 206:195–208 (1998).
O'Reilly, et al., "Angiostatin: A Novel Angiogenesis Inhibitor That Mediates the Suppression of Metastases by a Lewis Lung Carcinoma", *Cell* 79:315–328 (1994).
Cregg, et al. "Recent Advances in the Expression of Foreign Genes in *Pichia Pastoris*", *Biotechnology* 11:905–910 (1993).
Fogler, et al., "Recombinant Human Angiostatin Protein Expressed in *Pichia Pastoris* Inhibits B16BL6 Melanoma in an Experimental Metastasis Model", *Proceedings of the Amer. Ass. for Cancer Research Annual Meeting*, 39:46 (Mar., 1998).
Folkman, J., "Endogenous Inhibitors of Angiogenesis," *The Harvey Lectures*, 92:65–82 (1998).

* cited by examiner

*Primary Examiner*—James Ketter
(74) *Attorney, Agent, or Firm*—Barbara A. Gyure; Kathleen Williams; Palmer & Dodge LLP

(57) ABSTRACT

Methods for making proteins with anti-angiogenic properties are disclosed. The system used is a yeast expression system which produces biologically active proteins at high titer.

21 Claims, 31 Drawing Sheets

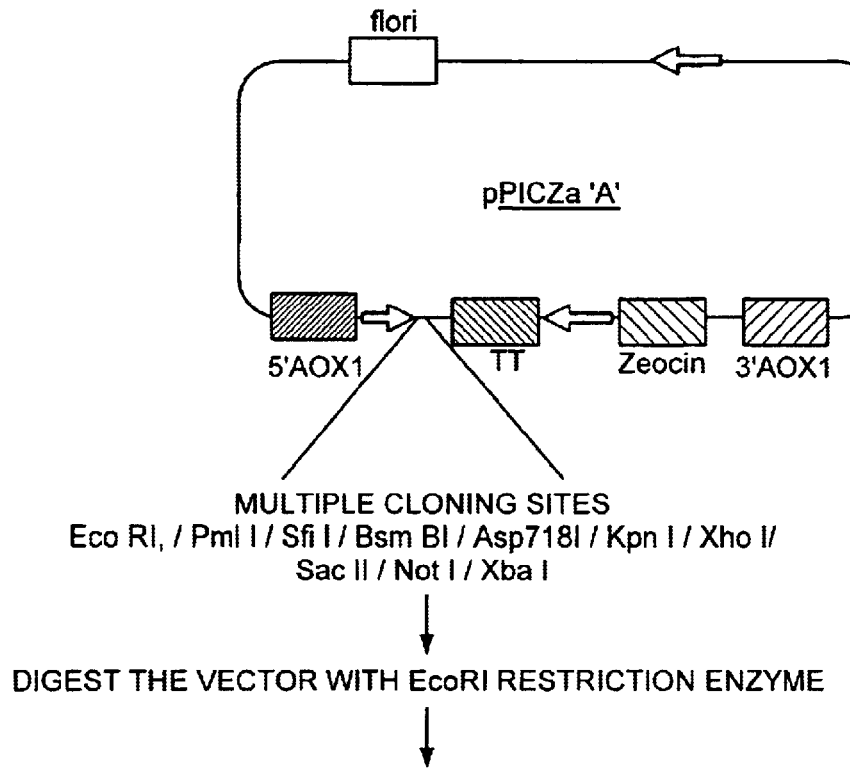

MULTIPLE CLONING SITES
Eco RI, / Pml I / Sfi I / Bsm BI / Asp718I / Kpn I / Xho I/
Sac II / Not I / Xba I

DIGEST THE VECTOR WITH EcoRI RESTRICTION ENZYME

DENATURE AND ANNEAL TWO COMPLIMENTARY OLIGO WHICH
WOULD INCORPORATE His. Tag MOTIF AND Nde I, Nhe I RESTRICTION
SITES (His. Tag REGION WOULD BE HELPFUL TO SIMPLIFY
PURIFICATION AND THE PRESENCE OF Nde I AND Nhe I RESTRICTION
SITES FACILITATE SHUTTLING OF PCR FROM PROKARYOTIC
EXPRESSION SYSTEM TO YEAST EXPRESSION WITHOUT GOING
THROUGH PCR AMPLIFICATION PROCESS)

5' AAT TCC ATC ACC ATC ACC ATC ACC ATA TGG CTA GCA 3'
5' AAT TTG CTA GCC ATA TGG TGA TGG TGA TGG TGA TGG 3'

MODIFIED PICHIA EXPRESSION VECTOR (pPICZ. His. A)

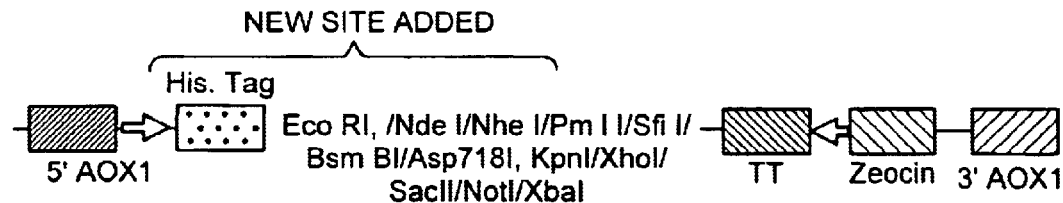

FIG. 2

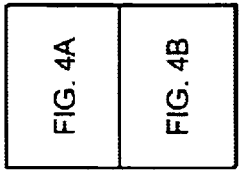

FIG. 4 endo sequence from Collagen XVIII.
Sequence Range: 1-555
Nucleotide 1 = Start for Endostatin and fragments EM1 and EM2.
EM1 fragment ends at nucleotide 525, EM2 fragment ends at nucleotide 501.

```
         5              10              15              20              25              30              35              40              45
CAT ACT CAT CAG GAC TTT CAG CCA GTG CTC CAC CTG GTG GCA CTG AAC
GTA TGA GTA GTC CTG AAA GTC GGT CAC GAG GTG GAC CAC CGT GAC TTG
        50              55              60              65              70              75              80              85              95
ACC CCC CTG TCT GGA GGC ATG CGT GGT ATC CGT GGA GCA GAT TTC CAG
TGG GGG GAC AGA CCT CCG TAC GCA CCA TAG GCA CCT CGT CTA AAG GTC
       100             105             110             115             120             125             130             135             140
TGC TTC CAG CAA GCC CGA GTG GGG CTG TCG GGC ACC TTC CGG GCT
ACG AAG GTC GTT CGG GCT CCC CAC AGC CCG AGC CCG TGG AAG GCC CGA
       145             150             155             160             165             170             175             180             190
TTC CTG TCC TCT AGG CTG CAG GAT CTC TAT AGC GTG CGC CGT GCT
AAG GAC AGG AGA TCC GAC GTC CTA GAG ATA TCG TAG CAC GCG GCA CGA
       195             200             205             210             215             220             225             230             240
GAC CGG GGG TCT GTG CCC ATC AAC CTG AAG GAC GAG GTG CTA TCT
CTG GCC CCC AGA CAC GGG TAG GTT GAC TTC CTC CAC GAT AGA
```

FIG. 4A

```
     245         250         255         260         265         270         275         280         285
CCC AGC TGG GAC TCC CTG TTT TCT GGC TCC CAG GGT CAA CTG CAA CCC
GGG TCG ACC CTG AGG GAC AAA AGA CCG AGG GTC CCA GTT GAC GTT GGG 290         295         300         305         310         315         320         325         330         335
GGG GCC CGC ATC TTT TCT TTT GAC GGC AGA GAT GTC CTG AGA CAC CCA
CCC CGG GCG TAG AAA AGA AAA CTG CCG TCT CTA CAG GAC TCT GTG GGT 340         345         350         355         360         365         370         375         380
GCC TGG CCG CAG AAG AGC GTA TGG CAC GGC TCG GAC CCC AGT GGG CGG
CGG ACC GGC GTC TTC TCG CAT ACC GTG CCG AGC CTG GGG TCA CCC GCC 385         390         395         400         405         410         415         420         425         430
AGG CTG ATG GAG AGT TAC TGT GAG ACA TGG CGA ACT GAA ACT ACT GGG
TCC GAC TAC CTC TCA ATG ACA CTC TGT GCT TGA CTT TGA TGA CCC 435         440         445         450         455         460         465         470         475         480
GCT ACA GGT CAG GCC TCC TCC CTG CTG TCA GGC CTC CTG GAA CAG
CGA TGT CCA GTC CGG AGG AGG GAC AGT CCG TCC GAG GAC CTT GTC 485         490         495         500         505         510         515         520         525
AAA GCT GCG AGC TGC CAC AAC AGC TAC ATC CTG TGC ATT GAG AAT
TTT CGA CGC TCG ACG GTG TTG TCG ATG TAG CAG GAC TAA CTC TTA 530         535         540         545         550         555
AGC TTC ATG ACC TCT TTC TCC AAA TAG
TCG AAG TAC TGG AGA AAG AGG TTT ATC
```

FIG. 4B

ENDOSTATIN

| Construct Name | Primer Sequence | Cloning Sites | Vector | Protein Sequence |
|---|---|---|---|---|
| MOUSE | ENDOSTATIN | | | |
| pET17b/ his.mendo | 5'-GGC ATA TGC ATA CTC ATC AGG-ACT TT-3' (up) (SEQ ID NO:4) | NdeI & XhoI | Prokaryotic expression, pET (E. coli his.endo) | MGHHHHHHHHSSGHIDDDDKH M-mendo (SEQ ID NO:14) |
| | 5' AAC TCG AGC TAT TTG GAG AAA- GAG GT-3' (down) (SEQ ID NO:5) | | | |
| pET28a/ mendo | 5'-GGC ATA TGC ATA CTC ATC AGG- ACT TT-3' (up) (SEQ ID NO:4) | NdeI & NotI | Prokaryotic expression, pET (E. coli his.endo) | MGSSHHHHHHSSGLVPRGSHM- mendo (SEQ ID NO:15) |
| | 5'-AAG CGG CCG CCT ATT TGG AGA- AAG AGG T-3' (down) (SEQ ID NO:6) | | | |
| pET28a/ EM-1 | 5' TTC CAT ATG CAT ACT CAT CAG- GAC TTT CAG CCA-3' (up) (SEQ ID NO:7) | | Prokaryotic expression, pET (E. coli EM1) | MGSSHHHHHHSSGLVPRGSHM-e ndo (SEQ ID NO:15) |
| | 5' TTA GCG GCC GCC TAC TCA ATG- CAC AGG ACG ATG TA-3' (down) (SEQ ID NO:8) | | | |
| pET28a/ EM-2 | 5' TTC CAT ATG CAT ACT CAT CAG- GAC TTT CAG CCA-3' (up) (SEQ ID NO:7) | | Prokaryotic expression, pET (E. coli EM2) | MGSSHHHHHHSSGLVPRGSHM-e ndo (SEQ ID NO:15) |
| | 5' TTA GCG GCC GCC TAG TTG TGG- CAG CTC GCA GCT TTC TG-3' (down) (SEQ ID NO:9) | | | |

FIG. 5A

| Construct Name | Primer Sequence | Cloning Sites | Vector | Protein Sequence |
|---|---|---|---|---|
| pPICZαA/ mendo (yeast mus endo) | 5' GGG AAT TCC ATA CTC ATC AGG- ACT TT-3' (up) (SEQ ID NO:10) | EcoRI & NotI | Eukaryotic expression, yeast/pPICZαA (yeast mouse endostatin) | EF-mendo (SEQ ID NO:16) |
| | 5' AAG CGG CCG CCT ATT TGG AGA- AAG AGG T-3' (down) (SEQ ID NO:6) | | | |
| pPICZαA/ His.mendo | 5' AAG AAT TCC ATC ATC ATC- ATC ACA GCA GC-3' (up) (SEQ ID NO:11) | EcoRI & NotI | Eukaryotic expression, yeast/pPICZαA (yeast mouse his.endostatin) | EFMGHHHHHHHHSSGHIDDDD KHM-mendo (SEQ ID NO:17) |
| | 5' AAG CGG CCG CCT ATT TGG AGA- AAG AGG T-3' (down) (SEQ ID NO:6) | | | |
| HUMAN ENDOSTATIN | | | | |
| pPICZαA/ Hendo | 5' TTT GAA TTC GCC CAC AGC CAC- CGC GAC TTC CAG CCG GTG CTC- CAC-3' (up) (SEQ ID NO:12) | EcoRI & NotI | Eukaryotic expression, yeast/pPICZαA (yeast human endostatin) | EF-hendo (SEQ ID NO:18) |
| | 5' AAA AGC GGC CGC CTA CTT GGA- GGC AGT CAT GAA GCT GTT CTC- AAT-3' (down) (SEQ ID NO:13) | | | |

FIG. 5B

Sequence Range: 1-546
Upstream primers for Restin and Apomigren are underlined,
downstream primer for both is double underlined. Primer
nucleotides not in the Restin sequence are shown in lower case.

```
    ttt ttt gaa ttc->
     5       10      15      20      25      30      35      40      45
->ATT TCA AGT GCC AAT TAT GAG AAG CCT GCT CTG CAT TTG GCT CTG
   TAA AGT TCA CGG TTA ATA CTC TTC GGA CGA GTA AAC CGA CGA GAC
    50      55      60      65      70      75      80      85      90      95
  AAC ATG CCA TTT TCT GGG GAC ATT CGA GCT GAT TTT CAG TGC TTC AAG
  TTG TAC GGT AAA AGA CCC CTG TAA GCT CGA CTA AAA GTC ACG AAG TTC
  100     105     110     115     120     125     130     135     140
  CAG GCC AGA GCT GCA GGA CTG TTG TCC ACC TAC CGA GCA TTC TTA TCT
  GTC CGG TCT CGA CGT CCT GAC AAC AGG TGG ATG GCT CGT AAG AAT AGA
  145     150     155     160     165     170     175     180     185     190
  TCC CAT TTG CAA GAT CTG TCC ACC ATT GTG AGG AAA GCA GAG AGA TAC
  AGG GTA AAC GTT CTA GAC AGG TGG TAA CAC TCC TTT CGT CTC TCT ATG
  195     200     205     210     215     220     225     230     235     240
  AGC CTT CCC ATA GTG AAC CTC AAG GGC CAA GTA CTT TTT AAT AAT TGG
  TCG GAA GGG TAT CAC TTG GAG TTC CCG GTT CAT GAA AAA TTA TTA ACC
```

FIG. 22A

| FIG. 22A |
|----------|
| FIG. 22B |

FIG. 22

```
         245         250         255         260         265         270         275         280         285
    GAC TCA ATT TTT TCT GGC CAC GGA GGT CAG TTC AAT ATG CAT ATT CCA
    CTG AGT TAA AAA AGA CCG GTG CCT CCA GTC AAG TTA TAC GTA TAA GGT
    ttc cat atg->
         290         295         300         305         310         315         320         325         330         335
    ->ATA TAC TCC TTT GAT GGT CGA GCT GTT GAC ATA ATG ACA GAT CCT TCT TGG CCC
       TAT ATG AGG AAA CTA CCA GCT CTG TAT TAC TGT CTA GGA AGA ACC GGG
         340         345         350         355         360         365         370         375         380
    CAG AAA GTC ATT TGG CAT GGC TCC AGC CCC CAT GGC GTC CGC CTT GTG
    GTC TTT CAG TAA ACC GTA CCG AGG TCG GGG GTA CAG CCG GAA CAC
         385         390         395         400         405         410         415         420         425         430
    GAT AAC TAC TGT GAA GCA CTT CGT ACC TGG CGA GAC ACA GCG GTC ACG GGA
    CTA TTG ATG ACA CTT CGT GAA GCA TGG ACC GCT CGC CTG TGT CGC CAG TGC CCT
         435         440         445         450         455         460         465         470         475         480
    CTT GCC TCC CCG AGC ACG CCG AGG AAG ATT CTG GAC CAG AAA GCA TAC
    GAA CGG AGG GGC GAC TCG TGC TGC CCC TTC TAA GAC CTG GTC TTT CGT ATG
         485         490         495         500         505         510         515         520         525
    AGC TGT GCT AAT CGG CTA ATT GTC CTA TGT GAT ACA AAC AGT TTC ATG
    TCG ACA CGA TTA GCC GAT TAA CAG GAT ACA TAG CTT TTG TCA AAG TAC
         530         535         540         545
    ACA GAC GCT AGG AAG TAA
    TGT CTG CGA TCC TTC ATT cgc cgg cgt aag aa
```

FIG. 22B

```
Sequence Range: 1 to 181

5      10    15    20    25    30    35    40    45
ISS  ANY  EKP  ALH  LAA  LNM  PFS  GDI  RAD  FQC  FKQ  ARA  AGL  LST  YRA  FLS 50   55    60    65    70    75    80    85    90    95
SHL  QDL  STI  VRK  AER  YSL  PIV  NLK  GQV  LFN  NWD  SIF  SGH  GGQ  FNM  HIP 100   105   110   115   120   125   130   135   140
IYS  FDG  RDI  MTD  PSW  PQK  VIW  HGS  SPH  GVR  LVD  NYC  EAW  RTA  DTA  VTG 145   150   155   160   165   170   175   180
LAS  PLS  TGK  ILD  QKA  YSC  ANR  LIV  LCI  ENS  FMT  DAR  K
```

FIG. 23

HUMAN RESTIN

| Construct Name | Primer Sequence | Cloning Sites | Vector | Protein Sequence |
|---|---|---|---|---|
| pPICZαA/Restin | 5' TTT TTT GAA TTC ATT TCA AGT- GCC AAT TAT GAG AAG CCT GCT- CTG CAT-TTG-3' (up) (SEQ ID NO:21) | EcoRI & NotI | Eukaryotic (Yeast), Pichia, pPICZαA | EF-restin (SEQ ID NO:27) |
|  | 5' AAG AAT GCG GCC GCT TAC TTC- CTA GCG TCT GTC ATG AAA CTG- TTT TCG AT-3' (down) (SEQ ID NO:22) |  | (yeast human restin) |  |
| pPICZαA/His.Restin | 5' AAT TCC ATC ACC ATC ACC ATC- ACG-3' (up) (SEQ ID NO:23) | EcoRI (oligo insertion) | Eukaryotic (Yeast), Pichia, pPICZαA | EFHHHHHH-restin (SEQ ID NO:28) |
|  | 5' AAT TCG TGA TGG TGA TGG TGA-TGG-3' (down) (SEQ ID NO:24) |  | (yeast human his.restin) |  |
| pET28a/apomigren | 5' TTC CAT ATG ATA TAC TCC TTT- GAT GGT CGA GAC ATA ATG ACA-3' (up) (SEQ ID NO:25) | NdeI & NotI | Prokaryotic, pET system | MGSSHHHHHHSSGLVPRGSHM-apomigren (SEQ ID NO:29) |
|  | 5' AAT GCG GCC GCT TAC TTC CTA- GCG TCT GTC ATG AAA CTG TTT- TCG AT-3' (down) (SEQ ID NO:26) |  | (E.coli human apomigren) |  |
| pPICZαA/apomigren | 5' AAG AAT TCC ATC ATC ATC ATC- ATC ACA GCA GC-3' (up) (SEQ ID NO:11) | EcoRI & NotI | Eukaryotic (Yeast), Pichia, pPICZαA | EFMGSSHHHHHHSSGLVPRGSHM-apomigren (SEQ ID NO:30) |
|  | 5' AAT GCG GCC GCT TAC TTC CTA- GCG TCT GTC ATG AAA CTG TTT- TCG AT-3' (down) (SEQ ID NO:26) |  | (yeast human apomigren) |  |

FIG. 25

SEQUENCE LISTING

<160> NUMBER OF SEQ ID NOS: 34

<210> SEQ ID NO 1
<211> LENGTH: 36
<212> TYPE: DNA
<213> ORGANISM: Artificial Sequence
<220> FEATURE:
<223> OTHER INFORMATION: Oligonucleotide

<400> SEQUENCE: 1
aattccatca ccatcaccat caccatatgg ctagca                       36

<210> SEQ ID NO 2
<211> LENGTH: 36
<212> TYPE: DNA
<213> ORGANISM: Artificial Sequence
<220> FEATURE:
<223> OTHER INFORMATION: Oligonucleotide

<400> SEQUENCE: 2
aatttgctag ccatatggtg atggtgatgg tgatgg                       36

<210> SEQ ID NO 3
<211> LENGTH: 555
<212> TYPE: DNA
<213> ORGANISM: Mus musculus
<220> FEATURE:
<221> NAME/KEY: misc_feature
<222> LOCATION: (1)...(525)
<223> OTHER INFORMATION: EM1
<221> NAME/KEY: misc_feature
<222> LOCATION: (1)...(501)
<223> OTHER INFORMATION: EM2

<400> SEQUENCE: 3
catactcatc aggactttca gccagtgctc cacctggtgg cactgaacac cccctgtct      60 ggaggcatgc gtggtatccg tggagcagat ttccagtgct tccagcaagc ccgagccgtg    120
gggctgtcgg gcaccttccg ggctttcctg tcctctaggc tgcaggatct ctatagcatc    180
gtgcgccgtg ctgaccgggg gtctgtgccc atcgtcaacc tgaaggacga ggtgctatct    240
cccagctggg actccctgtt ttctggctcc cagggtcaac tgcaacccgg ggcccgcatc    300
ttttcttttg acggcagaga tgtcctgaga cacccagcct ggccgcagaa gagcgtatgg    360
cacggctcgg accccagtgg gcggaggctg atggagagtt actgtgagac atggcgaact    420
gaaactactg gggctacagg tcaggcctcc tccctgctgt caggcaggct cctggaacag    480
aaagctgcga gctgccacaa cagctacatc gtcctgtgca ttgagaatag cttcatgacc    540
tctttctcca aatag                                                     555

<210> SEQ ID NO 4

```
<211> LENGTH: 26
<212> TYPE: DNA
<213> ORGANISM: Artificial Sequence
<220> FEATURE:
<223> OTHER INFORMATION: Oligonucleotide

<400> SEQUENCE: 4
ggcatatgca tactcatcag gacttt                                        26

<210> SEQ ID NO 5
<211> LENGTH: 26
<212> TYPE: DNA
<213> ORGANISM: Artificial Sequence
<220> FEATURE:
<223> OTHER INFORMATION: Oligonucleotide

<400> SEQUENCE: 5
aactcgagct atttggagaa agaggt                                        26

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide

<400> SEQUENCE: 6
aagcggccgc ctatttggag aaagaggt                                      28

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide

<400> SEQUENCE: 7
ttccatatgc atactcatca ggactttcag cca                                33

<210> SEQ ID NO 8
<211> LENGTH: 35
<212> TYPE: DNA
<213> ORGANISM: Artificial Sequence
<220> FEATURE:
<223> OTHER INFORMATION: Oligonucleotide

<400> SEQUENCE: 8
ttagcggccg cctactcaat gcacaggacg atgta                              35

<210> SEQ ID NO 9
<211> LENGTH: 38
<212> TYPE: DNA
<213> ORGANISM: Artificial Sequence
<220> FEATURE:
<223> OTHER INFORMATION: Oligonucleotide

<400> SEQUENCE: 9
ttagcggccg cctagttgtg gcagctcgca gctttctg                           38

<210> SEQ ID NO 10
<211> LENGTH: 26
<212> TYPE: DNA
<213> ORGANISM: Artificial Sequence
<220> FEATURE:
<223> OTHER INFORMATION: Oligonucleotide

<400> SEQUENCE: 10
```
gggaattcca tactcatcag gacttt                                          26

<210> SEQ ID NO 11
<211> LENGTH: 32
<212> TYPE: DNA
<213> ORGANISM: Artificial Sequence
<220> FEATURE:
<223> OTHER INFORMATION: Oligonucleotide

<400> SEQUENCE: 11
aagaattcca tcatcatcat catcacagca gc                                   32

<210> SEQ ID NO 12
<211> LENGTH: 45
<212> TYPE: DNA
<213> ORGANISM: Artificial Sequence
<220> FEATURE:
<223> OTHER INFORMATION: Oligonucleotide

<400> SEQUENCE: 12
tttgaattcg cccacagcca ccgcgacttc cagccggtgc tccac                     45

<210> SEQ ID NO 13
<211> LENGTH: 45
<212> TYPE: DNA
<213> ORGANISM: Artificial Sequence
<220> FEATURE:
<223> OTHER INFORMATION: Oligonucleotide

<400> SEQUENCE: 13
aaaagcggcc gcctacttgg aggcagtcat gaagctgttc tcaat                     45

<210> SEQ ID NO 14
<211> LENGTH: 24
<212> TYPE: PRT
<213> ORGANISM: Artificial Sequence
<220> FEATURE:
<223> OTHER INFORMATION: Leader peptide on protein produced y
      prokaryotic expression system pET17

<400> SEQUENCE: 14

Met Gly His His His His His His His His His His Ser Ser Gly His
 1               5                   10                  15

Ile Asp Asp Asp Asp Lys His Met
            20

<210> SEQ ID NO 15
<211> LENGTH: 21
<212> TYPE: PRT
<213> ORGANISM: Artificial Sequence
<220> FEATURE:
<223> OTHER INFORMATION: Leader peptide on protein produced y
      prokaryotic expression system pET28A

<400> SEQUENCE: 15

Met Gly Ser Ser His His His His His His Ser Ser Gly Leu Val Pro
 1               5                   10                  15

Arg Gly Ser His Met
            20

<210> SEQ ID NO 16
<211> LENGTH: 2
<212> TYPE: PRT
<213> ORGANISM: Artificial Sequence
<220> FEATURE:

-continued

<223> OTHER INFORMATION: Leader peptide on protein produced y
      prokaryotic expression system pPICZaA

<400> SEQUENCE: 16

Glu Phe
 1

<210> SEQ ID NO 17
<211> LENGTH: 26
<212> TYPE: PRT
<213> ORGANISM: Artificial Sequence
<220> FEATURE:
<223> OTHER INFORMATION: Leader peptide on protein produced y
      prokaryotic expression system pPICZaA

<400> SEQUENCE: 17

Glu Phe Met Gly His His His His His His His His Ser Ser
 1               5                  10                  15

Gly His Ile Asp Asp Asp Asp Lys His Met
            20                  25

<210> SEQ ID NO 18
<211> LENGTH: 3
<212> TYPE: PRT
<213> ORGANISM: Artificial Sequence
<220> FEATURE:
<223> OTHER INFORMATION: Leader peptide on protein produced y
      prokaryotic expression system pPICZaA

<400> SEQUENCE: 18

Glu Phe Ala
 1

<210> SEQ ID NO 19
<211> LENGTH: 546
<212> TYPE: DNA
<213> ORGANISM: Homo sapiens
<220> FEATURE:
<221> NAME/KEY: misc_feature
<222> LOCATION: (289)...(543)
<223> OTHER INFORMATION: apomigren DNA sequence

<400> SEQUENCE: 19
atttcaagtg ccaattatga gaagcctgct ctgcatttgg ctgctctgaa catgccattt      60
tctggggaca ttcgagctga ttttcagtgc ttcaagcagg ccagagctgc aggactgttg     120
tccacctacc gagcattctt atcttcccat ttgcaagatc tgtccaccat tgtgaggaaa     180
gcagagagat acagccttcc catagtgaac ctcaagggcc aagtactttt taataattgg     240
gactcaattt tttctggcca cggaggtcag ttcaatatgc atattccaat atactccttt     300
gatggtcgag acataatgac agatccttct tggccccaga aagtcatttg gcatggctcc     360
agcccccatg gcgtccgcct tgtggataac tactgtgaag catggcgaac cgcggacaca     420
gcggtcacgg gacttgcctc cccgctgagc acggggaaga ttctggacca gaaagcatac     480
agctgtgcta atcggctaat tgtcctatgt atcgaaaaca gtttcatgac agacgctagg     540
aagtaa                                                               546

<210> SEQ ID NO 20
<211> LENGTH: 181
<212> TYPE: PRT
<213> ORGANISM: Homo sapiens

<400> SEQUENCE: 20

―continued

```
Ile Ser Ser Ala Asn Tyr Glu Lys Pro Ala Leu His Leu Ala Ala Leu
 1               5                  10                  15

Asn Met Pro Phe Ser Gly Asp Ile Arg Ala Asp Phe Gln Cys Phe Lys
             20                  25                  30

Gln Ala Arg Ala Ala Gly Leu Leu Ser Thr Tyr Arg Ala Phe Leu Ser
         35                  40                  45

Ser His Leu Gln Asp Leu Ser Thr Ile Val Arg Lys Ala Glu Arg Tyr
     50                  55                  60

Ser Leu Pro Ile Val Asn Leu Lys Gly Gln Val Leu Phe Asn Asn Trp
 65                  70                  75                  80

Asp Ser Ile Phe Ser Gly His Gly Gly Gln Phe Asn Met His Ile Pro
                 85                  90                  95

Ile Tyr Ser Phe Asp Gly Arg Asp Ile Met Thr Asp Pro Ser Trp Pro
                100                 105                 110

Gln Lys Val Ile Trp His Gly Ser Pro His Gly Val Arg Leu Val
             115                 120                 125

Asp Asn Tyr Cys Glu Ala Trp Arg Thr Ala Asp Thr Ala Val Thr Gly
        130                 135                 140

Leu Ala Ser Pro Leu Ser Thr Gly Lys Ile Leu Asp Gln Lys Ala Tyr
145                 150                 155                 160

Ser Cys Ala Asn Arg Leu Ile Val Leu Cys Ile Glu Asn Ser Phe Met
                165                 170                 175

Thr Asp Ala Arg Lys
            180
```

<210> SEQ ID NO 21
<211> LENGTH: 51
<212> TYPE: DNA
<213> ORGANISM: Artificial Sequence
<220> FEATURE:
<223> OTHER INFORMATION: Oligonucleotide

<400> SEQUENCE: 21 tttttttgaat tcatttcaag tgccaattat gagaagcctg ctctgcattt g    51

<210> SEQ ID NO 22
<211> LENGTH: 50
<212> TYPE: DNA
<213> ORGANISM: Artificial Sequence
<220> FEATURE:
<223> OTHER INFORMATION: Oligonucleotide

<400> SEQUENCE: 22
aagaatgcgg ccgcttactt cctagcgtct gtcatgaaac tgttttcgat    50

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide

<400> SEQUENCE: 23
aattccatca ccatcaccat cacg    24

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide

```
<400> SEQUENCE: 24
aattcgtgat ggtgatggtg atgg                                          24

<210> SEQ ID NO 25
<211> LENGTH: 42
<212> TYPE: DNA
<213> ORGANISM: Artificial Sequence
<220> FEATURE:
<223> OTHER INFORMATION: Oligonucleotide

<400> SEQUENCE: 25
ttccatatga tatactcctt tgatggtcga gacataatga ca                      42

<210> SEQ ID NO 26
<211> LENGTH: 47
<212> TYPE: DNA
<213> ORGANISM: Artificial Sequence
<220> FEATURE:
<223> OTHER INFORMATION: Oligonucleotide

<400> SEQUENCE: 26
aatgcggccg cttacttcct agcgtctgtc atgaaactgt tttcgat                 47

<210> SEQ ID NO 27
<211> LENGTH: 2
<212> TYPE: PRT
<213> ORGANISM: Artificial Sequence
<220> FEATURE:
<223> OTHER INFORMATION: Leader peptide on protein produced by
      eukaryotic yeast expression system pPICZaA

<400> SEQUENCE: 27

Glu Phe
 1

<210> SEQ ID NO 28
<211> LENGTH: 8
<212> TYPE: PRT
<213> ORGANISM: Artificial Sequence
<220> FEATURE:
<223> OTHER INFORMATION: Leader peptide on protein produced by
      eukaryotic yeast expression system pPICZaA

<400> SEQUENCE: 28

Glu Phe His His His His His His
 1               5

<210> SEQ ID NO 29
<211> LENGTH: 21
<212> TYPE: PRT
<213> ORGANISM: Artificial Sequence
<220> FEATURE:
<223> OTHER INFORMATION: Leader peptide on protein produced by
      prokaryotic expression system pET

<400> SEQUENCE: 29

Met Gly Ser Ser His His His His His His Ser Ser Gly Leu Val Pro
 1               5                  10                  15

Arg Gly Ser His Met
            20

<210> SEQ ID NO 30
<211> LENGTH: 23
<212> TYPE: PRT
<213> ORGANISM: Artificial Sequence
```

-continued

```
<220> FEATURE:
<223> OTHER INFORMATION: Leader peptide on protein produced by
      prokaryotic expression system pET

<400> SEQUENCE: 30

Glu Phe Met Gly Ser Ser His His His His His His Ser Ser Gly Leu
 1               5                  10                  15

Val Pro Arg Gly Ser His Met
            20

<210> SEQ ID NO 31
<211> LENGTH: 29
<212> TYPE: DNA
<213> ORGANISM: Artificial Sequence
<220> FEATURE:
<223> OTHER INFORMATION: Oligonucleotide

<400> SEQUENCE: 31
aagaattcgt gttgtatctg tcagaatgt                                      29

<210> SEQ ID NO 32
<211> LENGTH: 27
<212> TYPE: DNA
<213> ORGANISM: Artificial Sequence
<220> FEATURE:
<223> OTHER INFORMATION: Oligonucleotide

<400> SEQUENCE: 32
agcggccgcc taccctcctg tctctga                                        27

<210> SEQ ID NO 33
<211> LENGTH: 26
<212> TYPE: DNA
<213> ORGANISM: Artificial Sequence
<220> FEATURE:
<223> OTHER INFORMATION: Oligonucleotide

<400> SEQUENCE: 33
aagaattcgt gtatctctca gagtgc                                         26

<210> SEQ ID NO 34
<211> LENGTH: 27
<212> TYPE: DNA
<213> ORGANISM: Artificial Sequence
<220> FEATURE:
<223> OTHER INFORMATION: Oligonucleotide

<400> SEQUENCE: 34
agcggccgcc tattctgttc ctgagta                                        27
```

METHODS OF PRODUCING ANTI-ANGIOGENIC PROTEINS

RELATED APPLICATIONS

This application is a continuation of international application PCT/US98/25892, filed Dec. 8, 1998, which claims priority to application 60/067,888, filed Dec. 8, 1997, 60/082,663, filed Apr. 22, 1998, and 60/108,536, filed Nov. 16, 1998, the entire teachings of all of which are incorporated herein by reference.

BACKGROUND OF THE INVENTION

The prognosis for metastatic cancer remains highly unfavorable. Despite advances in radiation therapy and chemotherapy, the long term survival of treated patients has shown only marginal improvement over the past few decades. The lack of significant treatment options available for metastatic cancers emphasizes the need to focus on the development of novel therapeutic strategies. In this regard, targeting tumor vasculature of solid tumors has recently shown promising results in several animal model systems (Baillie et al. (1995) *Br. J. Cancer* 72:257–67; Bicknell, R. (1994) *Ann. Oncol.* 5 (Suppl.) 4:45–50; Fan et al. (1995) *Trends Pharmacol. Sci.* 16:57–66, Thorpe, P. E. and Burrows, F. J. (1995) *Breast Cancer Res. Treat.* 36:237–51; Burrows, F. J. and Thorpe, P. E. (1994) *Pharmacol. Ther.* 64:155–74). In a nude mouse model, for instance, introduction of a wild type VHL gene into 786-0 cells, a RCC tumor cell line, inhibited tumor growth (Iliopoulos et al. (1995) *Nat. Med.* 1:822–26) and angiogenesis.

The growth of solid tumors beyond a few $mm^3$ depends on the formation of new blood vessels (Folknan, J. (1971) *N. Engl. J. Med.* 285:1182–86). Numerous studies have shown that both primary tumor and metastatic growth are angiogenesis-dependent (Folkman, J. (1971) *N. Engl. J. Med.* 285:1182–86; Folkman, J. (1972) *Ann. Surg.* 175:409–16; Folknan, J. and Shing, Y. (1992) *J. Biol. Chem.* 267:10931–34; Folkman, J. (1996) *Sci. Am.* 275:150–54). A number of angiogenesis inhibitors have been identified. Certain ones, such as platelet factor-4 (Maione et al. (1990) *Science* 247:77–79; Gupta et al. (1995) *Proc. Natl. Acad. Sci. (USA)* 92:7799–7803), interferon, interferon-inducible protein-10, and PEX (Angiolillo et al. (1995) *J. Exp. Med.* 182:155–62; Stricter et al. (1995) *Biochem. Biophys. Res. Commun.* 210:51–57; Brooks et al. (1998) *Cell* 92:391–400), are not "associated with tumors," whereas two others, angiostatin and endostatin, are "tumor-associated" (O'Reilly et al. (1994) *Cell* 79:315–28; O'Reilly et al. (1997) *Cell* 88:277–85). Angiostatin, a potent endogenous inhibitor of angiogenesis generated by tumor-infiltrating macrophages that upregulate matrix metalloelastase (Dong et al. (1997) *Cell* 88:801–10), inhibits the growth of a wide variety of primary and metastatic tumors (Lannutti et al. (1997) *Cancer Res.* 57:5277–80; O'Reilly et al. (1994) *Cold Spring Harb. Symp. Quant. Biol.* 59:471–82; O'Reilly, M. S., (1997) *Exs.* 79:273–94; Sim et al. (1997) *Cancer Res.* 57:1329–34; Wu et al. (1997) *Biochem. Biophys. Res. Commun.* 236:651–54). Recently, O'Reilly, et al. ((1997) *Cell* 88:277–85) have isolated endostatin, an angiogenesis inhibitor from a murine hemangioendothelioma cell line (EOMA). Circulating levels of a fragment of human endostatin have been detected in patients with chronic renal insufficiency with no detectable tumor (Wu et al. (1997) *Biochem. Biophys. Res. Commun.* 236:651–54).

The amino terminal sequence of endostatin corresponds to the carboxy terminal portion of collagen XVIII. Endostatin is a specific inhibitor of endothelial proliferation and angiogenesis. Systemic administration of non-refolded precipitated protein expressed in *Escherichia coli* caused growth regression of Lewis lung carcinoma, T241 fibrosarcoma, B16 melanoma and EOMA cells (O'Reilly et al. (1997) *Cell* 88:277–85)in a xenograft model. Moreover, no drug resistance was noted in three of the tumor types studied. Repeated cycles of administration with endostatin have been reported to result in tumor dormancy (Boehm et al.(1997) *Nature* 390:404–407).

The results from these angiostatin and endostatin studies open new avenues for treatment of cancer and provide promising routes for overcoming the drug resistance often seen during chemotherapy. However, in all of these investigations, a non-refolded precipitated form of the inhibitor protein was administered in the form of a suspension to tumor bearing animals. In addition, large amounts of protein were required to cause tumor regression and to lead to tumor dormancy. As pointed out by Kerbel ((1997) *Nature* 390:335–36), oral drug equivalents of these proteins are needed. Mechanistic investigations could be undertaken if recombinant forms of these proteins were available in soluble form. Moreover, initial testing could be done in vitro with soluble protein before studying its efficacy under in vivo conditions.

Furthermore, there have been reports that despite the great promise held by these proteins, evaluation of their clinical potential is stymied due to difficulties in producing enough of the protein to test, and inconsistent test results regarding their anti-angiogenic properties, e.g., anti-angiogenic activity (King, R. T., *Wall Street J.*, Page 1, November 12 (1998); Leffe, D. N., *BioWorld Today*, 9:1, October 20 (1998)). There clearly exists at the present time a great need for a reproducible method of producing soluble forms of anti-angiogenic proteins with sufficient biological activity to be clinically effective and to reliably produce these proteins in high yields without sacrificing such critical activity.

SUMMARY OF THE INVENTION

The present invention relates to the discovery of a reproducible method of producing anti-angiogenic proteins with biological activity sufficient to be clinically effective. As described herein, the anti-angiogenic proteins encompassed by the present methods are reproducibly produced in high yields (for example from 10 to 20 mg/liter of culture medium. Importantly, the anti-angiogenic proteins produced by the methods described herein retain high biological activity.

Anti-angiogenic proteins are well-known to those of skill in the art. For example, angiostatin, endostatin, the 16 kD prolactin fragment, RNAisn, TNP470, 2-methoxy estradiol and heparin, to name a few. As used herein, the term "anti-angiogenic protein(s)" encompass not only intact proteins, but mutants (e.g., with amino acid residues added, deleted or altered), fragments (e.g., specifically with amino acids deleted), derivatives (e.g., modified proteins or peptides, for example to reduce protease degradation) and fusion proteins wherein the fusion proteins comprise a combination of two or more known anti-angiogenic proteins (e.g., angiostatin and endostatin, or biologically active fragments of angiostatin and endostatin), or an anti-angiogenic protein in combination with a targeting agent (e.g., endostatin with epidermal growth factor (EGF) or RGD peptides), or an anti-angiogenic protein in combination with an immunoglobulin molecule (e.g., endostatin and IgG, specifically with the Fc portion removed). The term "fusion protein" as used herein can also encompass additional components for e.g., delivering a chemotherapeutic agent, wherein a polynucleotide encoding the chemotherapeutic agent is linked to the polynucleotide encoding the anti-angiogenic protein. Fusion proteins can also encompass multimers of the anti-angiogenic protein, e.g., a dimer or trimer of endostatin.

It is also to be recognized that any of the anti-angiogenic proteins described herein can be post-translationally modified to encompass targeting moieties (e.g., vascular endotheleial growth factor (VEGF) or chemotherapeutic agents, such as ricin, or radioisotopes. Additional post-translational modifications can include multimerization, e.g., by chemical cross-linking using techniques well-know to those of skill in the art. However, for brevity, the term "anti-angiogenic protein" is used herein without specifically referring to mutant, derivatives, fragments and fusion proteins.

Encompassed by the present invention are methods of producing a biologically active anti-angiogenic protein, or a biologically active mutant, fragment, derivative or fusion protein thereof, using a prokaryotic or eukaryotic expression system. Specifically encompassed is the use of a yeast expression system, more specifically the *Pichia pastoris* yeast expression system.

The method steps involve inserting an isolated polynucleotide comprising a polynucleotide sequence encoding an anti-angiogenic protein, or mutant or derivative or fragment or fusion protein thereof, into a suitable expression vector e.g., prokaryotic or eukaryotic. Specifically encompassed by the present invention are yeast expression vectors. Suitable yeast expression vectors are well-known to those of skill in the art. A particularly suitable expression vector for use in the methods described herein is the commercially available Pichia vector comprising pPICzαA plasmid wherein the plasmid contains a multiple cloning site. The polynucleotide sequences of anti-angiogenic proteins are well-known in the art, and novel anti-angiogenic protein sequences, as well as mutant sequences of known anti-angiogenic proteins are also described herein, and in PCT/US98/26058, "Restin and Methods of Use Thereof," by Vikas P. Sukhatme, filed Dec. 8, 1998, and in U.S. Ser. No. 09/589,774, "Restin and Methods of Use Thereof", by Vikas P. Sukhatme, filed Jun. 8, 2000, and in PCT/US98/26057, "Mutants of Endostatin, 'EM1' Having Anti-Angiogenic Activity and Methods of Use Thereof," by Vikas P. Sukhatme, filed Dec. 8, 1998, and in U.S. Ser. No. 09/589,887, "Anti-Angiogenic Peptides and Method of Use Thereof", by Vikas P. Sukhatme, filed Jun. 8, 2000, the teachings of all of which are herein incorporated by reference in their entirety. Inserting the selected polynucleotide sequence into the vector is routine to those of skill, and is also described herein.

After inserting the selected polynucleotide into the vector, the vector is transformed into an appropriate yeast strain and the yeast strain is cultured (e.g., maintained) under suitable culture conditions for the production of the biologically active anti-angiogenic protein, thereby producing a biologically active anti-angiogenic protein, or mutant, derivative, fragment or fusion protein thereof. Typically the anti-angiogenic proteins are produced in quantities of about 10–20 milligrams, or more, per liter of culture fluid.

In one embodiment, the isolated polynucleotide encoding the anti-angiogenic protein additionally comprises a polynucleotide linker encoding a peptide. Such linkers are known to those of skill in the art and, for example, the linker can comprise at least one additional codon encoding at least one additional amino acid. Typically the linker comprises one to about twenty or thirty amino acids. Typically the linker is attached to the 5' end of the polynucleotide encoding the anti-angiogenic protein, but can also be attached to the 3' end. The polynucleotide linker is translated, as is the polynucleotide encoding the anti-angiogenic protein, resulting in the expression of an anti-angiogenic protein with at cast one additional amino acid residue at the amino or carboxyl terminus of the anti-angiogenic protein. For example, as described herein, the anti-angiogenic protein, endostatin is expressed using the methods described herein with two additional amino acid residues 5' to endostatin. (See FIG. 5) These two additional amino acid residues are glutamic acid (E) and phinylalanine (F). Additionally, other amino acid residues can comprise the anti-antiogenic protein (See FIGS. 5 and 25). Importantly, the additional amino acid, or amino acids, do not compromise the activity of the anti-angiogenic protein. In fact, the anti-angiogenic proteins produced by the methods described herein exhibit superior biological activity to anti-angiogenic proteins produced by other expression methods. Typically, the concentrations of anti-angiogenic proteins produced in this embodiment are about 10–20 milligrams per liter of culture medium.

In another embodiment of the present invention, the eukaryotic vector comprises a yeast vector comprising a histadine tag motif. As described herein, one method uses a pPICzαA plasmid wherein the plasmid contains a multiple cloning site which contains a His.Tag motif (also referred to herein as pPICzαA/HIS.). Additionally the vector can be modified to add a Ndel site, or other suitable restriction sites. Such sites are well known to those of skill in the art. Anti-angiogenic proteins produced by this embodiment comprise a histidine tag motif (His.tag) comprising one, or more histadine, typically about 5–20 histidines. Surprisingly, this His.tag does not compromise anti-angiogenic activity. In fact, the anti-angiogenic proteins produced by the methods described herein exhibit superior biological activity to anti-angiogenic proteins produced by other expression methods. Again, the biologically active protein is typically produced at concentrations of about 10–20 milligrams per liter of culture medium (fluid).

Combinations of the above embodiments are also encompassed by the present invention. For example, the selected polynucleotide can comprise a linker and be inserted into a vector comprising his.Tag motif. (See FIGS. 5 and 25).

Also encompassed by the present invention are the anti-angiogenic proteins produced by the methods described herein. Surprisingly, the proteins produced by the methods described herein are produced in high yields and have biological activity sufficient for testing the clinical efficacy of these proteins to inhibit (completely, or substantially reduce) unwanted angiogenic activity.

Further encompassed by this invention are methods of using the anti-angiogenic proteins produced by the methods described herein. For example, the anti-angiogenic proteins described herein can be used to test the efficacy of treating human malignant tumors wherein such treatment would result in the regression, partial, or complete, of the tumor. These proteins can also be used to treat other diseases that have undesirable angiogenesis as described herein.

Further encompassed by the present invention are compositions comprising an effective amount of an anti-angiogenic protein produced by the methods described herein, and a pharmaceutically acceptable carrier. An effective amount of an anti-angiogenic protein is described herein, and typically is an amount sufficient to inhibit endothelial activity such as endothelial cell migration, inhibition of tumor growth, arrest of endothelial cells in $G_1$ phase of the cell cycle, and inducing apoptosis in endothelial cells. Assays to determine these activities are described herein. "$ED_{50}$" is an abbreviation for the amount of anti-angiogenic protein which reduces a biological effect by one-half relative to the biological effect seen in the absence of the anti-angiogenic protein. Comparing the concentration of an anti-angiogenic protein required to reduce a biological effect by one-half, in for example, the endothelial cell proliferation assay, is a useful measure of biological activity and allows comparison between compositions.

Also encompassed by the present invention are methods of using the anti-angiogenic proteins described herein to inhibit undesirable angiogenic activity. The methods encompassed by the present invention can inhibit endothelial cell migration, inhibit tumor growth in mammals, arrest endothelial cells in $G_1$ phase of the cell cycle, and induce apoptosis in endothelial cells. The anti-angiogenic proteins of the present invention specifically and reversibly inhibit endothelial cell proliferation. The inhibitor protein molecules of the invention are also useful as a birth control drug, and for treating other angiogenesis-related diseases, particularly angiogenesis-dependent cancers and tumors.

As a result of the invention described herein, quantities of anti-angiogenic proteins, mutants, derivatives and fragments thereof, as well as anti-angiogenic fusion proteins are now available with sufficient biological activity for the study and treatment of angiogenic diseases. The unexpected and surprising ability of these anti-angiogenic compounds to treat and alleviate angiogenesis-dependent cancers and tumors answers a long felt unfulfilled need in the medical arts, and provides an important benefit to mankind.

BRIEF DESCRIPTION OF THE DRAWINGS

FIG. 2 is a schematic diagram of the modified *Pichia pastoris* expression vector.

FIG. 4 depicts the mouse endostatin sequence and sequences of endostatin mutants EM1 and EM2.

FIG. 5A and FIG. 5B are tables showing yeast construct names, primer sequences, cloning sites, vectors for the production of endostatin. Also shown are protein sequences for the produced proteins. HTH-endo indicates the mouse endostatin amino acid sequence. AHSH-endo indicates the human endostatin amino acid sequence.

FIG. 22 depicts the restin and restin M2 nucleotide sequence.

FIG. 23 depicts the restin amino acid sequence.

FIG. 25 is a graph showing the construct names, primer sequences, cloning sites, and vector systems for producing restin and restin mutants amino acid of restin and mutant restin (Apomigren, also referred to herein as restin-M2) sequences are also shown. The " . . . restin" indicate the restin amino acid sequence.

DETAILED DESCRIPTION OF THE INVENTION

Figure 1:
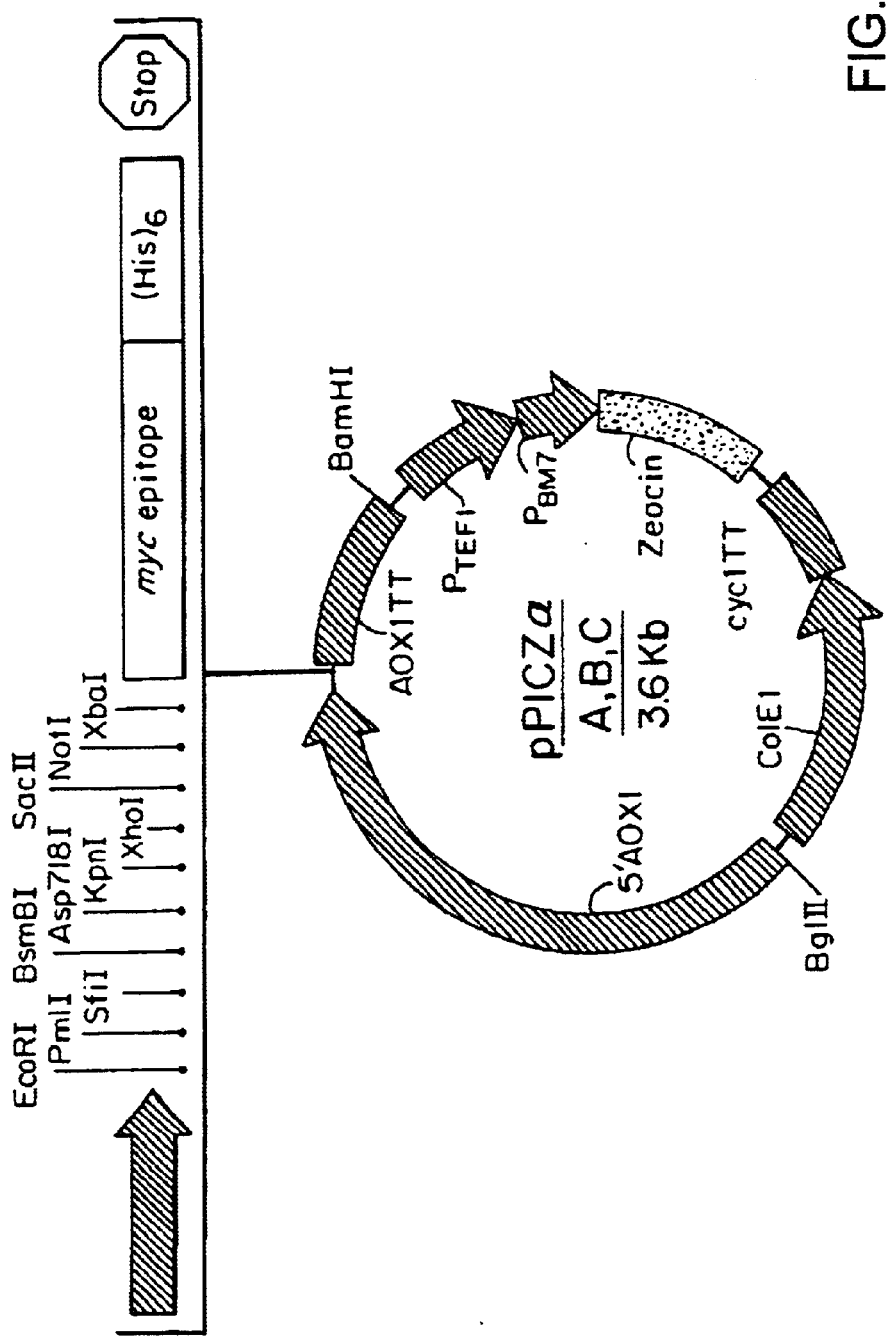
FIG. 1 is a schematic diagram of the *Pichia pastoris* expression vector.

In accordance with the present invention, compositions and methods are provided that are effective for modulating angiogenesis, and inhibiting unwanted angiogenesis, especially angiogenesis related to tumor growth.

The present invention specifically encompasses methods of producing anti-angiogenic proteins, specifically including angiostatin, endostatin and restin, and mutants, derivatives, fragments and fusion proteins thereof. Angiostatin, endostatin, and restin, when produced in E. coli, may be contaminated with endotoxin, or may be denatured (i.e., the protein may be improperly folded). Isolation of the native forms of these proteins from serum or via production in mammalian cells results in proteins with variable, and often very low anti-angiogenic activity levels, and also results in low yields of these proteins. As described herein, however, production of these proteins in the yeast expression system of the present invention results in yields of 10–20 mg of protein per liter of culture.

The yeast expression system of the present invention utilizes the Pichia expression system (InVitrogen, San Diego, Calif.). Pichia pastoris is a methanotrophic yeast strain capable of using methanol as a carbon source. It has the advantages of a eukaryotic expression system, including protein processing, protein folding, and post-translational modifications, and is suitable for large scale fermentation precesses. This system exhibits a high level of heterologous protein expression. In one embodiment the system uses a vector comprising a histidine tag motif. However, other suitable yeast expression systems can also be utilized and vectors can be modified to contain a histidine tag motif using standard techniques. Alternatively, the selected protein to be expressed can be modified with a linker as described herein. Addition of linkers to polynucleotide sequences encoding proteins are well-known to those of skill in the art. The specific steps of the methods of the present invention are described in detail in the Examples.

The term "vector" as used herein means a carrier that can contain or associate with specific nucleic acid sequences (polynucleotides), which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising an anti-angiogenic protein inhibitor DNA sequence is operatively linked to an expression control sequence to form an expression vector capable of expressing the protein.

A "vector" is also referred to herein as a replicon in which another polynucleotide segment is attached, such as to bring about the replication and/or expression of the attached segment. As used herein, "replicon" means any genetic element, such as a plasmid, a chromosome or a virus, that behaves as an autonomous unit of polynucleotide replication within a cell.

The term "control sequence" refers to polynucleotide sequences which are necessary to effect the expression of coding sequences to which they are ligated. The nature of such control sequences differs depending upon the host organism. In eukaryotes, such control sequences generally include promoters, terminators and, in some instances, enhancers. The term "control sequence" thus is intended to include at a minimum all components whose presence is necessary for expression, and also may include additional components whose presence is advantageous. for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide. This region may represent a portion of a coding sequence or a total coding sequence. A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

The term "isolated" as used herein means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Purified" or "isolated" polynucleotide refers to a polynucleotide of interest or fragment thereof which is essentially free, i.e., contains less than about 50%, preferably less than about 70%, and more preferably, less than about 90% of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography or sedimentation according to density.

The term "primer" denotes a specific oligonucleotide sequence complementary to a target nucleotide sequence and used to hybridize to the target nucleotide sequence and serve as an initiation point for nucleotide polymerization catalyzed by either DNA polymerase, RNA polymerase or reverse transcriptase.

A "recombinant polypeptide" as used herein means at least a polypeptide which by virtue of its origin or manipulation is not associated with all or a portion of the polypeptide with which it is associated in nature and/or is linked to a polypeptide other than that to which it is linked in nature. A recombinant or derived polypeptide is not necessarily translated from a designated nucleic acid sequence. It also may be generated in any manner, including chemical synthesis or expression of a recombinant expression system.

"Polypeptide" as used herein indicates a molecular chain of amino acids and does not refer to a specific length of the product. Thus, peptides, oligopeptides and proteins are included within the definition of polypeptide. This term is also intended to refer to post-expression modifications of the polypeptide, for example, glycosylations, acetylations, phosphorylations and the like. "Purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art.

The present invention specifically encompasses methods of producing a protein, which has been named "angiostatin," defined by its ability to overcome the angiogenic activity of endogenous growth factors such as bFGF, in vitro, and by its amino acid sequence homology and structural similarity to an internal portion of plasminogen beginning at approximately plasminogen amino acid 98 (see, e.g., U.S. Pat. Nos. 5,801,012, 5,837,682, 5,733,876, 5,776,704, 5,639,725, 5,792,845, WO 96/035774, WO 95/29242, WO 96/41194 and WO 97/23500). Angiostatin comprises a protein having a molecular weight of between approximately 38 kDa and 45 kDa as determined by reducing polyacrylamide gel electrophoresis and having an amino acid sequence substantially similar to that of a fragment of murine plasminogen beginning at amino acid number 98 of an intact murine plasminogen molecule (O'Reilly, M. S., et al., *Cell,* 79:315–328 (1994), the teachings of which are incorporated herein in their entirety by reference.

The amino acid sequence of angiostatin varies slightly between species. For example, in human angiostatin the amino acid sequence is substantially similar to the sequence of the above described murine plasminogen fragment, although an active human angiostatin sequence may start at either amino acid number 97 or 99 of an intact human plasminogen amino acid sequence. Furthermore, fragments of human plasminogen have similar anti-angiogenic activity as shown in a mouse tumor model. It is to be understood that the number of amino acids in the active angiostatin molecule may vary and all amino acid sequences that have endothelial inhibiting activity are contemplated as being included in the present invention (see, e.g., U.S. Pat. Nos. 5,801,012, 5,837,682, 5,733,876, 5,776,704, 5,639,725, 5,792,845, WO 96/035774, WO 95/29242, WO 96/41194 and WO 97/23500).

Angiostatin is also defined as a protein that has a molecular weight of approximately 38 to 45 kDa that is capable of overcoming the angiogenic activity of endogenous growth factors such as bFGF, in vitro. Angiostatin is a protein having a molecular weight of between approximately 38 kDa and 45 kDa as determined by reducing polyacrylamide gel electrophoresis and having an amino acid sequence substantially similar to that of a murine plasminogen fragment beginning at amino acid number 98 of an intact murine plasminogen molecule.

The term "substantially similar," when used in reference to angiostatin amino acid sequences mean an amino acid sequence having anti-angiogenic activity and having a molecular weight of approximately 38 kD to 45kD, which also has a high degree of sequence similarity, or identity, to the peptide fragment of mouse plasmiogen beginning approximately at amino acid number 98 in mouse plasminogen and weighing 38 kDa to 45 kDa.

"Sequence identity," as used herein, refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. By way of example, the amino acid sequences $R_{20}R_2R_8R_{11}R_6R_{15}$ and $R_9R_1R_{14}R_{11}R_6R_{15}$ have 3 of 6 positions in common, and therefore share 50% sequence identity, while the sequences $R_{20}R_2R_8R_{11}R_6R_{15}$ and $R_1R_{14}R_{11}R_6R_{15}$ have 3 of 5 positions in common, and therefore share 60% sequence identity. The identity between two sequences is a direct function of the number of matching or identical positions. Thus, if a portion of the reference sequence is deleted in a particular peptide, that deleted section is not counted for purposes of calculating sequence identity, e.g., $R_{20}R_2R_8R_{11}R_6R_{15}$ and $R_{20}R_2R_8R_{11}R_{15}$ have 5 out of 6 position in common, and therefore share 83.3% sequence identity.

Identity is often measured using sequence analysis software e.g., BLASTN or BLASTP (available to the public on the world wide web at the web site of the National Center for Biotechnology Information (".ncbi"), National Library of Medicine (".nlm"), National Institutes of Health (".nih") of the United States government (".gov")). The default parameters for comparing two sequences (e.g., "Blast"-ing two sequences against each other) by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1.

When two sequences share "sequence homology," it is meant that the two sequences differ from each other only by conservative substitutions. For polypeptide sequences, such conservative substitutions consist of substitution of one amino acid at a given position in the sequence for another amino acid of the same class (e.g., amino acids that share characteristics of hydrophobicity, charge, pK or other conformational or chemical properties, e.g., valine for leucine, arginine for lysine), or by one or more non-conservative amino acid substitutions, deletions, or insertions, located at positions of the sequence that do not alter the conformation or folding of the polypeptide to the extent that the biological activity of the polypeptide is destroyed. Examples of "conservative substitutions" include substitution of one nonpolar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue, such as aspartic acid or glutamic acid for another; or the use of a chemically derivatized residue in place of a non-derivatized residue; provided that the polypeptide displays the requisite biological activity. Two sequences which share sequence homology may called "sequence homologs." A polypeptide containing a chemically-derivatized residue is a "chemical derivative" of the reference polypeptide.

Homology, for polypeptides, is typically measured using sequence analysis software (e.g., Sequence Analysis Software Package of the Genetics Computer Group, University of Wisconsin Biotechnology Center, 1710 University Avenue, Madison, Wis. 53705). Protein analysis software matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Also encompassed by the present invention are methods of making endostatin. The term "endostatin" refers to a protein that is preferably 18 kDa to 20 kDa in size as determined by non-reduced and reduced gel electrophoresis, respectively. (O'Reilly, M. S., et al., *Cell,* 88:277–285 (1997), the teachings of which are herein incorporated by reference in their entirety. The term endostatin also includes precursor forms of the 18 kDa to 20 kDa protein. Endostatin also includes fragments of the 18 kDa to 20 kDa protein and modified proteins and peptides that have a substantially similar amino acid sequence, and which are capable inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of this invention.

The N-terminal amino acid sequence of endostatin corresponds to an internal 20 amino acid peptide fragment found in mouse collagen alpha 1 type XVIII starting at amino acid 1105 and ending at amino acid 1124 (see, e.g., U.S. Pat. Nos. 5,801,012, 5,837,682, 5,733,876, 5,776,704, 5,639,725, 5,792,845, WO 96/035774, WO 95/29242, WO 96/41194 and WO 97/23500). The N-terminal amino acid sequence of the inhibitor also corresponds to an internal 20 amino acid peptide fragment found in human collagen alpha 1 type XVIII starting at amino acid 1132 and ending at amino acid 1151. Also encompassed by the present invention are endostatin mutants are endostatin mutants, as described PCT/US98/26057, "Mutants of Endostatin, 'EM1' Having Anti-Angiogenic Activity and Methods of Use Thereof," by Vikas P. Sukhatme filed on Dec. 8, 1998, and in U.S. Ser. No. 09/589,777, "Anti-Angiogenic Peptides and Method of Use Thereof", by Vikas P. Sukhatme, filed Jun. 8, 2000, the entire teachings of both of which are herein incorporated in their entirety by reference. The biological activity of these mutants can be evaluated as described herein and compared to the biological activity of the "wild type" endostatin, or endostatin produced by other methods.

Endostatin can be isolated from murine hemangioendothelioma EOMA. Endostatin may be produced from recombinant sources, from genetically altered cells implanted into animals, from tumors, and from cell cultures as well as other sources. Endostatin can be isolated from body fluids including, but not limited to, serum, urine and ascites, or synthesized by chemical or biological methods (e.g., cell culture, recombinant gene expression, peptide synthesis, and in vitro enzymatic catalysis of precursor molecules to yield active endostatin). Recombinant techniques include gene amplification from DNA sources using the polymerase chain reaction (PCR), and gene amplification from RNA sources using reverse transcriptase /PCR.

Also encompassed by the present invention are methods of producing restin. Applicants have discovered a new class of protein molecules described in PCT/US98/26058, "Restin and Methods of Use Thereof," by Vikas P. Sukhatme filed on Dec 8, 1998, and in U.S. Ser. No. 09/589,774, "Restin and Method of Use Thereof", by Vikas P. Sukhatme, filed Jun. 8, 2000 the teachings of both which are incorporated herein by reference in their entirety, that have the ability to inhibit endothelial proliferation when added to proliferating endothelial cells in vitro. Accordingly, these protein molecules and restin mutants have been functionally defined as restins, however, it is to be understood that this functional definition in no way limits the bioactivity of restins to inhibition of endothelial cell growth in vitro or in vivo. Many other functions of restins are likely. Restin is a proteolytic fragment, and part of the collagen XV family. (See FIGS. 22–23). The restin protein is an approximately 20 kD C-terminal fragment of collagen XV and has no affinity for heparin. Also, specifically encompassed by the present invention are fragments or mutants of restin.

One such fragment, designated "Apomigren", was found to have anti-angiogenic activity equivalent or superior to that of human or mouse endostatin, as determined by standard assays. Apomigren comprises the last approximately 85 amino acid residues of Restin itself, from about amino acid 97 to about amino acid 181 of SEQ ID NO:20:

IYS FDG RDI MTD PSW PQK VIW HGS SPH GVR LVD NYC EAW RTA

DTA VTG LAS PLS TGK ILD QKA YSC ANR LIV LCI ENS FMT DAR K The polynucleotide sequence encoding Apomigren therefore corresponds to about nucleotide 289 to about nucleotide 543 of SEQ ID NO: 19, and can be amplified out of SEQ ID NO: 19 with the forward primer 5'-TTT CAT ATG ATA TAC TCC TTT GAT GGT CGA GAC ATA ATG ACA (SEQ ID NO:25) and the same reverse primer as that used for Restin (SEQ ID NO:26). Cloning and expression of Apomigren is done as for Restin itself, as illustrated in the Examples below. Apomigren provides an advantage in treatment of angiogenic diseases in that increasingly smaller peptides are more potent on a weight basis, and may be able to better penetrate tissues.

It will be appreciated that the terms "angiostatin, endostatin and restin" include shortened proteins or peptides, referred to herein as mutants or fragments, wherein one or more amino acid is removed from either or both ends of endostatin, or from an internal region of the protein, yet the resulting molecule retains endothelial proliferation inhibiting activity. The terms "angiostatin, endostatin and restin" also include lengthened proteins or peptides wherein one or more amino acid is added to either or both ends of endostatin, or to an internal location in the protein, yet the resulting molecule retains endothelial proliferation inhibiting activity. Such molecules, for example with tyrosine added in the first position are useful for labeling such as radioiodination with $^{125}$iodine for use in assays. Labeling with other radioisotopes may be useful in providing a molecular tool for destroying the target cell containing endostatin receptors. Other labeling with molecules such as ricin may provide a mechanism for destroying cells with anti-angiogenic protein receptors.

Also included in the definition of the terms "angiostatin, endostatin and restin". are modifications of the protein, its subunits and peptide fragments. Such modifications include substitutions of naturally occurring amino acids at specific sites with other molecules, including but not limited to naturally and non-naturally occurring amino acids. Such substitutions may modify the bioactivity of the anti-angiogenic protein and produce biological or pharmacological agonists or antagonists. Modifications can also include modified amino acids within the protein sequence, or modifications to the intact protein sequence that inhibit protease activity, or otherwise enhance the stability of the protein and decrease protein degradation. Such modifications are well-known to those of skill in the art. See, for example U.S. Ser. No. 08/988,842, the teachings of which are herein incorporated by reference.

Modified proteins are also referred to herein as derivative proteins, or analogs. The term "derivative" or "analog" includes any protein/polypeptide having an amino acid residue sequence substantially identical to a sequence specifically shown herein in which one or more residues have been conservatively substituted with a functionally similar residue and which displays the activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between threonine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypetide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and omithine may be substituted for lysine. Polypeptides of the present invention also include any polypeptide having one or more additions and/or deletions of residues relative to the sequence of a polypeptide whose sequence is shown herein, so long as the requisite activity is maintained.

The present invention also contemplates amino acid residue sequences that are analogous to sequences of the proteins described herein, and the nucleic acid sequences encoding these proteins. It is well known in the art that modifications and changes can be made without substantially altering the biological function of the protein. In making such changes, substitutions of like amino acid residues can be made on the basis of relative similarity of side-chain substituents, for example, their size, charge, hydrophobicity, hydrophilicity and the like. Alterations of the type described may be made to enhance the peptide's potency or stability to enzymatic breakdown or pharmacokinetics. Thus, sequences deemed as within the scope of the invention, include those analogous sequences characterized by a change in amino acid residue sequence or type wherein the change does not alter the fundamental nature and biological activity of the aforementioned anti-angiogenic proteins, derivatives, mutants fragments and/or fusion proteins.

Anti-angiogenic fusion proteins of the present invention encompass a protein comprising one or more of the proteins, mutants, derivatives or fragments described herein as well as other anti-angiogenic molecules known to those of skill in the art. For example, a fusion protein encompassed by the present invention can be encoded by a polynucleotide encoding endostatin linked to restin wherein the expressed fusion protein comprises activity of both endostatin and restin, resulting in a reasonable increase of the biological activity of the fusion protein over either monomeric wild-type endostatin or restin. Another type of fusion protein encompassed by the present invention can be a fusion protein encoded by a polynucleotide encoding two restin molecules in tandem, optionally linked by a linker. Again, it is reasonable to predict that the fusion protein would have higher activity than the monomeric restin.

Other examples of anti-angiogenic fusion proteins of the present invention include conjugates of the proteins. Such fusion proteins may or may not be capable of being cleaved into the separate proteins from which they are derived. As used herein, the term "conjugate of an anti-angiogenic protein" means an anti-angiogenic protein chemically coupled to another protein to form a conjugate. Examples of conjugates include a protein fragment coupled to albumin or to a peptide fragment from another anti-angiogenic protein.

As used herein, the term "anti-angiogenesis activity" refers to the capability of a molecule to inhibit the growth of blood vessels. As used herein, the term "endothelial inhibiting activity" refers to the capability of a molecule to inhibit angiogenesis in general and, for example, to inhibit the growth or migration of bovine capillary endothelial cells in culture in the presence of fibroblast growth factor or other known growth factors. An anti-angiogenic protein, mutant, derivative, fragment or fusion protein of the present invention may be characterized on the basis of potency when tested for its "endothelial inhibiting activity". Other measures of endothelial inhibiting activity are described herein.

The anti-angiogenic proteins of the present invention are effective in treating diseases or processes that are mediated by, or involve, angiogenesis. The present invention includes the method of treating an angiogenesis-mediated disease with an effective amount of an anti-angiogenic protein produced by the methods described herein, or a biologically active mutant, derivative, fragment or fusion protein thereof, or combinations of proteins that collectively possess anti-angiogenic activity, or the activity of anti-angiogenic agonists and antagonists.

As used herein, the term "angiogenesis" means the generation of new blood vessels into a tissue or organ, and involves endothelial cell proliferation. Under normal physiological conditions, mammals (humans or animals) undergo angiogenesis only in very specific restricted situations. For example, angiogenesis is normally observed in wound healing, fetal and embryonal development, and formation of the corpus luteum, endometrium and placenta. The term "endothelium" means a thin layer of flat epithelial cells that lines serous cavities, lymph vessels, and blood vessels.

As used herein, the term "angiogenesis-associated factor" means a factor which either inhibits or promotes angiogenesis. An example of an angiogenesis-associated factor is an angiogenic growth factor, such as basic fibroblastic growth factor (bFGF), which is an angiogenesis promoter. Another example of an angiogenesis associated factor is an angiogenesis inhibiting factor such as angiostatin.

As used herein, the term "growth factor" means a molecule that stimulates the growth, reproduction, or synthetic activity of cells.

The angiogenesis mediated diseases include, encompassed herein but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Angiostatin is useful in the treatment of disease of excessive or abnormal stimulation of endothelial cells. These diseases also include, but are not limited to, intestinal adhesions, Crohn's disease, atherosclerosis, scleroderma, and hypertrophic scars, i.e., keloids. The anti-angiogenic proteins described herein can also be used as a birth control agent by preventing vascularization required for embryo implantation. The proteins are also useful in the treatment of diseases that have angiogenesis as a pathologic consequence such as cat scratch disease (*Rochele minalia quintosa*) and ulcers (*Helicobacter pylori*).

As used herein, the term "cancer" means angiogenesis-dependent cancers and tumors, i.e., tumors that require for their growth (expansion in volume and/or mass) an increase in the number and density of the blood vessels supplying them with blood. More specifically, as used herein, the term "cancer" means neoplastic growth, hyperplastic or proliferative growth or a pathological state of abnormal cellular development and includes solid tumors, non-solid tumors, and any abnormal cellular proliferation, such as that seen in leukemia. "Regression" refers to the reduction of tumor mass and size as measured using standard techniques.

Administration and Dosing

An anti-angiogenic protein produced by the methods of the present invention can be used in a composition, wherein the protein is combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The compositions of the present invention may also contain other anti-angiogenic proteins or chemical compounds, such as endostatin, angiostatin, restin, and mutants, derivatives, fragments, and analogs thereof. The composition may further contain other agents which either enhance the activity of the protein or compliment its activity or use in treatment, such as chemotherapeutic or radioactive agents. Such additional factors and/or agents may be included in the composition to produce a synergistic effect with protein of the invention, or to minimize side effects. Additionally, administration of the composition of the present invention may be administered concurrently with other therapies, e.g., administered in conjunction with a chemotherapy or radiation therapy regimen.

A protein of the present invention may be active in multimers (e.g., heterodimers or homodimers) or complexes with itself or other proteins. As a result, compositions of the invention may comprise a protein of the invention in such multimeric or complexed form. Such multimers, or complexes, are especially useful to prolong the half-life of the anti-angiogenic protein in circulation. Alternatively, it may be undesirable to administer the anti-angiogenic protein systemically because of side-affects. In this case, it is useful to conjugate the anti-angiogenic protein with a targeting agent to deliver (target) the anti-angiogenic protein to a specific tissue, or organ. For example, the anti-angiogenic protein can comprise a peptide to target to specific cell surface receptors (e.g., VEGF to target vasculature). Such targeting molecules are well known to those of skill in the art.

The compositions of the present invention can be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. The anti-angiogenic protein of the present invention can be administered in accordance with the method of the invention, either alone or in combination with other therapies. Such administration can be current or sequential. If administered sequentially, the attending physician will decide on the appropriate sequence of administering protein of the present invention in combination with the other factors.

As used herein, the term "prodrug" refers to compounds which are rapidly transformed in vivo to yield the parent compound, for example, by enzymatic hydrolysis in blood. A thorough discussion is provided in T. Higuchi and V. Stella, *Prodrugs as Novel Delivery Systems*, Vol. 14 of the ACS Symposium Series and in Edward B. Roche, ed., *Bioreversible Carriers in Drug Design*, American Pharmaceutical Association and Permagon Press, 1987, both of which are incorporated herein by reference. Also as used herein, prodrug can encompass an anti-angiogenic protein which requires processing in the mammal in order to become activated, for example an anti-angiogenic protein that requires proteolytic cleavage resulting in a protein with anti-angiogenic activity.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 micrograms to about 100 mg (preferably about 0.1 micrograms to about 10 mg, more preferably about 0.1 micrograms to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

The term "parenteral", as used herein, refers to modes of administration which include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyois (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly (orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The compounds of the present invention may be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences* (1977) 66:1 et seq., which is incorporated herein by reference. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention.

Polynucleotides encoding the anti-angiogenic proteins, mutants, derivatives, fragments and fusion proteins of the present invention can also be used for gene therapy. The use of gene therapy is supported when a steady supply (e.g., chronic supply) of the anti-angiogenic protein is desirable. Such polynucleotides can be introduced either in vivo or ex vivo into cells for expression in a mammalian subject. For example, a suitable vector containing the polynucleotide encoding the anti-angiogenic protein can be introduced into the bone marrow, muscle, liver or joint (in the case of rheumatorid arthritis, when the protein would be expressed in the synovial fluid). Methods of gene therapy are know to those of skill in the art (see for example, U.S. Pat. No 5,398,346, the teachings of which are incorporated herein in their entirety).

Polynucleotides of the invention may also be administered by other known methods for introduction of nucleic acid into a cell or organism (including, without limitation, in the form of viral vectors or naked DNA). Alternatively, cells can also be cultured ex vivo in the presence of proteins of the present invention in order to proliferate or to produce a desired effect on or activity in such cells. Treated cells can then be introduced into the mammal, wherein the anti-angiogenic proteins are expressed for therapeutic purposes.

Proteins of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc., 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The present invention is illustrated by the following examples, which are not intended to be limited in any way.

EXAMPLES

Example 1

Cell Lines

C-PAE, a calf pulmonary artery endothelial cell line, and ECV304, a human endothelial cell line, were obtained from ATCC (American Type Culture Collection, 10801 University Boulevard, Manassas, Va., 20110-2209, USA). The C-PAE cell line was maintained in DMEM and ECV304 in M199, both supplemented with 10% fetal calf serum (FCS), 100 U/ml penicillin, 100 g/ml of streptomycin and 2 mM L-glutamine. HUVE (human umbilical vein endothelial cell line) and HMVE-L (human microvascular endothelial cell (lung) cell line) were purchased from Clonetics Corporation (San Diego, Calif., USA). HUVE cells were maintained in EGM medium containing bovine brain extract (3 mg/ml), hEGF (10 g/ml), hydrocortisone (1 g/ml), 2% FCS, gentamicin (50 mg/ml, 0.5 ml), and amphotericin (50 g/ml). The HMVE-L cells were maintained in EGM-2 medium containing growth factors suggested by the manufacturer according to standard protocols (Clonetics, Inc., CA manufacturer's directions). The yeast expression system, *Pichia pastoris* (pPICZαA) was purchased from InVitrogen (San Diego, Calif., USA). Restriction enzymes and Vent DNA polymerase were purchased from New England Bio Labs (Beverly, Mass., USA). IMR-90 (ATCC No.: CCL-186) and WI-38 (ATCC No.: CCL-75), human fibroblast were also purchased from ATCC.

Example 2

Cloning and Expression of Mouse Endostatin into Prokaryotic System

The sequences for endostatin are shown in FIGS. 4 and 5. The sequence encoding the carboxy terminal portion of mouse collagen XVIII was amplified by PCR using Vent DNA polymerase. The endostatin pBACPak8 vector was used as a template for PCR amplification. The primers used were as follows:

5'-GGC-ATA-TGC-ATA-CTC-ATC-AGG-ACT-TT-3' (SEQ ID NO:4) 5'-AAC-TCG-AGCTA-TTT-GGA-GAA-AGA-GGT-3' (SEQ ID NO:5). PCR was carried out for 30 cycles, each cycle having the following parameters: 94° C. denaturation, 60° C. for annealing and 72° C. extension, for 1 minute each. The amplified DNA fragment (555 bp) was purified using a QIAquick PCR purification kit and then digested with NdeI and XhoI. The digested fragment was then ligated into a predigested expression vector pET17bhis (Dhanabal, M., Fryxell, D. K. & Ramakrishnan, S. (1995) J. Immunol. Methods 182:165–175). Initial transformation was carried out with the HMS 174 host strain. Positive clones were sequenced on both strands. The desired clones were finally transformed into BL21(DE3) for expression. The expression of recombinant protein in the pET system was carried out as described by the manufacturer.

Figure 6A:
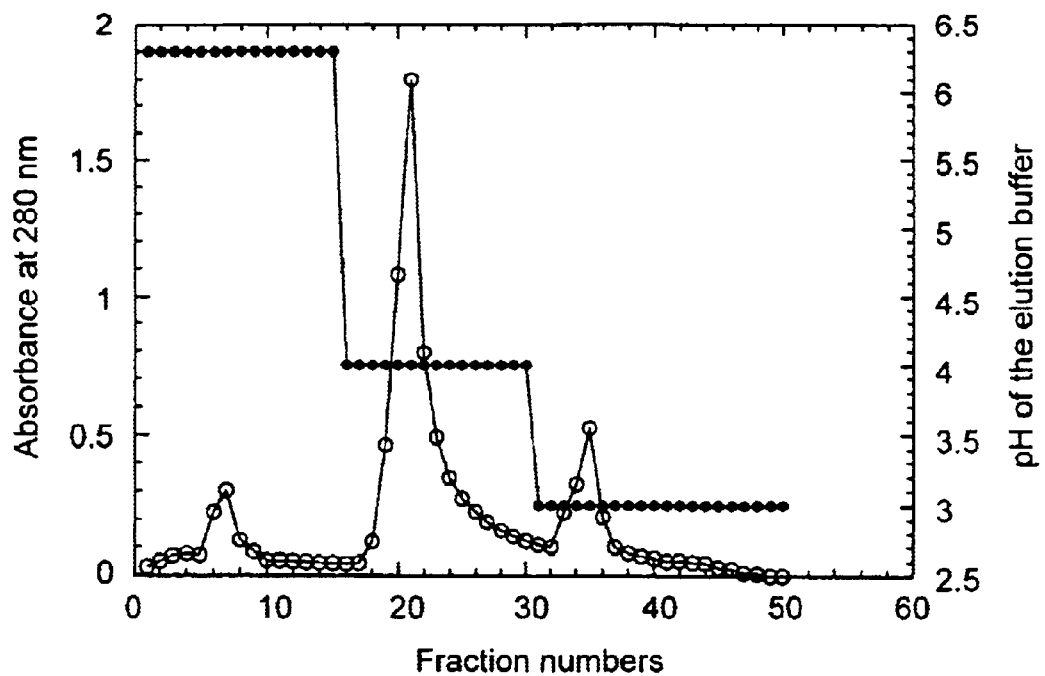
FIG. 6A shows the purification of recombinant mouse endostatin using a Ni-NTA column. The protein was purified under denaturing conditions. The solubilized protein containing 8 M urea was loaded on a Ni-NTA column and the bound protein was eluted by decreasing the pH of the elution buffer. (•) pH of the elution buffer. (○) Absorbance at 280 nm.
Figure 6B:
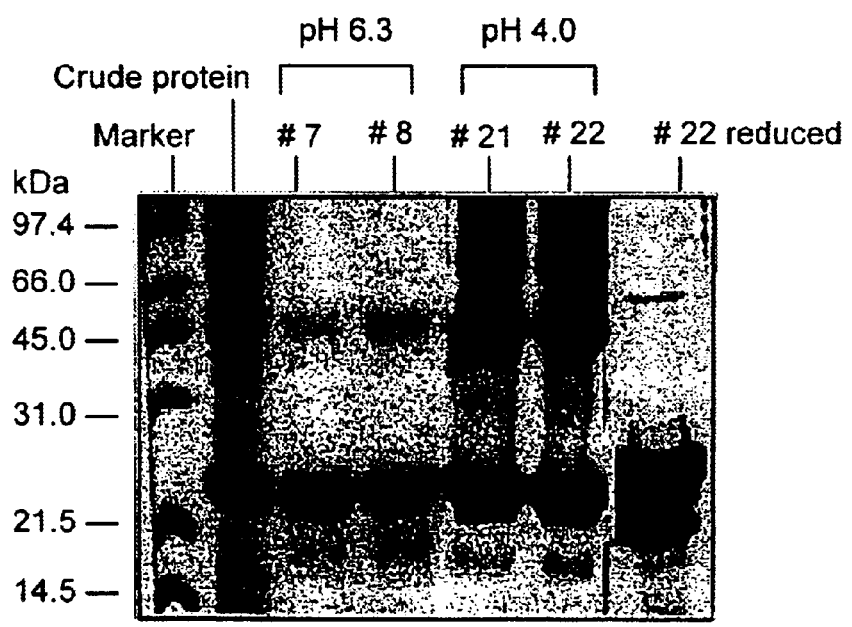
FIG. 6B shows the purified mouse endostatin protein was analyzed by 12% SDS-PAGE. kDa marker-low molecular weight protein standards are shown at left. 10 ml of selected fractions from each elution point were analyzed. In addition to the expected 22–24 kDa protein, considerable amounts of higher molecular weight complexes corresponding to 46 and 69 kDa were also seen. When the protein was reduced with DTT, all the higher molecular weight complexes converted to a monomeric subunit corresponding to 22–24 kDa.

An Ni-NTA agarose column was used to purify the recombinant protein (FIG. 6A). Protein present in inclusion bodies was solubilized in 8 M urea and purified under denaturing condition as described by O'Reilly et al. (O'Reilly, M. S., Boehm, T., Shing, Y., Fukai, N., Vasios, G., Lane, W. S., Flynn, E., Birkhead, J. R., Olsen, B. R. & Folkman, J. (1997) Cell 88:277–285). SDS-PAGE analysis showed a discrete band at 22–24 kDa under non-reducing conditions (FIG. 6B). In addition, higher molecular complexes were also observed, which upon reduction resulted in a discrete band at 22–24 kDa. The peaks at different pH elutions were pooled and dialyzed against decreasing concentrations of urea, and final dialysis was performed in PBS buffer pH 7.4, at which time most of the proteins precipitated out of solution. Since non-refolded precipitated protein expressed from a similar system had shown biological activity in vivo, the procedure followed was exactly that used for "protein refolding" (as described by O'Reilly et al. (O'Reilly, M. S., Boehm, T., Shing, Y., Fukai, N., Vasios, G., Lane, W. S., Flynn, E., Birkhead, J. R., Olsen, B. R. & Folkman, J. (1997) Cell 88:277–285). The precipitated protein was used in suspension form for in vivo experiments only, with the concentration of protein measured by the BCA method (solubilized in urea with a suitable blank) and stored at −70° C. in small aliquots. Unpublished observations cited in O'Reilly et al., (O'Reilly, M. S., Boehm, T., Shing, Y., Fukai, N., Vasios, G., Lane, W. S., Flynn, E., Birkhead, J. R., Olsen, B. R. & Follnan, J. (1997) Cell 88:277–285) indicated that a C-terminal His.Tag on endostatin destroyed its biological activity. Therefore endostatin mutant, EM 1, a 19 kDa protein, was generated with an 11 amino acid deletion from the C-terminus, leaving all 4 of the cysteine residues intact. Endostatin mutant EM 2 is a further 8 amino acid deletion that omits the most C-terminal cysteine.

Primers were designed such that 9 and 17 amino acids were deleted from the C-terminus of endostatin for EM 1 and EM 2 respectively. The amplified DNA fragments (525 bp for EM 1, 501 bp for EM 2) were purified, digested with NdeI and NotI, and ligated into a predigested pET28(a) expression vector. The rest of the protocol was carried out as described above. The induction conditions and processing of the bacterial pellet were carried out as described elsewhere (O'Reilly, M. S., Boehm, T., Shing, Y., Fukai, N., Vasios, G., Lane, W. S., Flynn, E., Birkhead, J. R., Olsen, B. R. & Folkman, J. (1997) Cell 88:277–285). The purification of recombinant protein was performed using a Ni-NTA column in the presence of 8M urea as described in the QIAexpressionist manual. Briefly, the bacterial pellet was solubilized in "equilibration buffer" (8M urea, 10 mM Tris and 100 mM sodium phosphate buffer pH 8.0) for one hour at room temperature. The suspension was sonicated 3–4 times, centrifuged at 10,000×gravity and the soluble fraction was loaded on a Ni-NTA vivo studies. EM 1 and EM 2 were purified using the Ni-NTA column. Non-specific proteins bound to the column were removed by an equilibration buffer wash, followed by a 10 mM imidazole wash. Bound proteins were eluted in equilibration buffer containing 10% glycerol and 0.2 M acetic acid. The purified proteins were refolded according to the method described above.

Example 3
Expression of Mouse Endostatin in *Pichia Pastoris*

Figure 3:
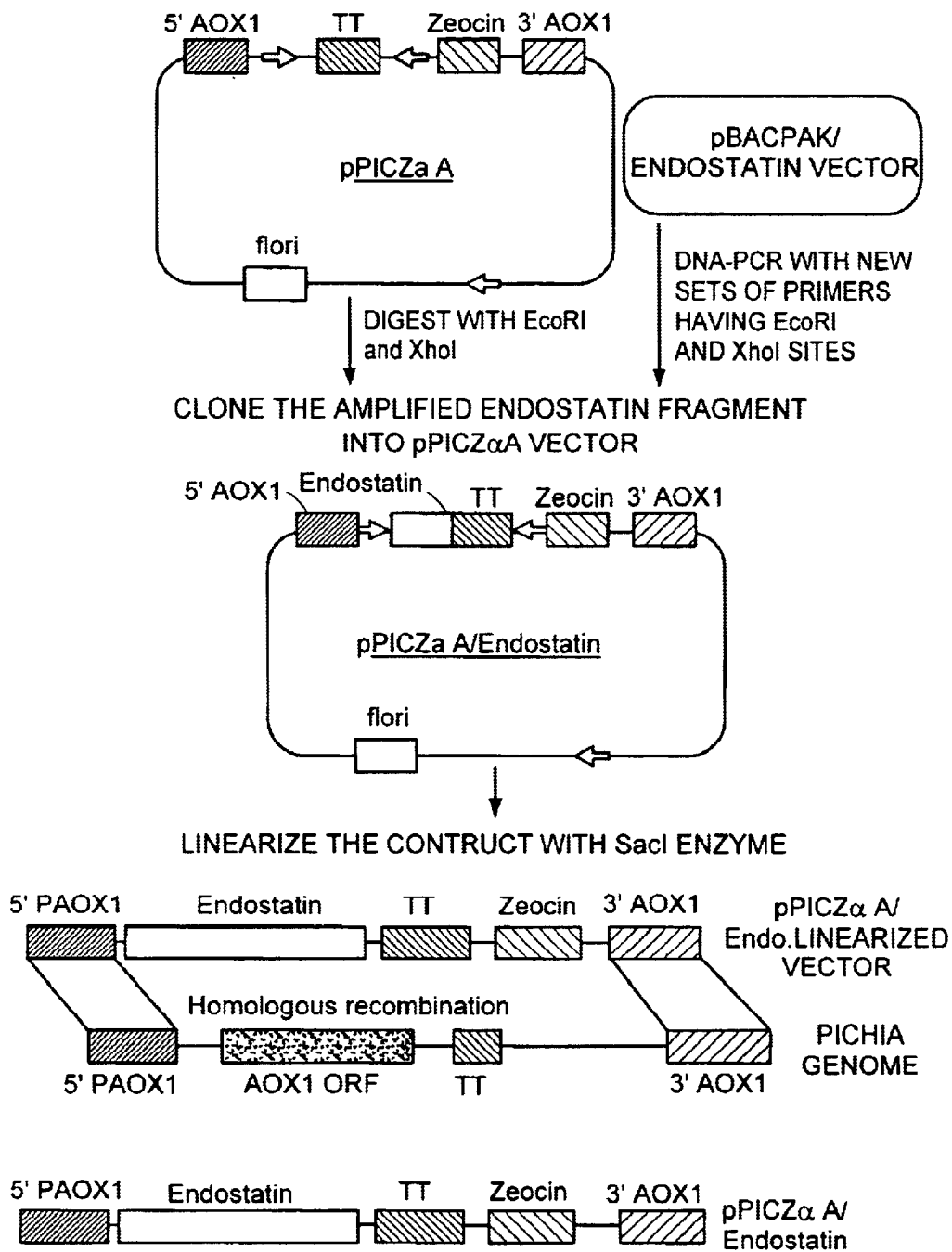
FIG. 3 is a schematic representation of the cloning of endostatin using the *Pichia pastoris* expression system of the present invention.

The pPICZαA is shown in FIGS. 1 and 2. The sequence encoding mouse endostatin was further modified by PCR using Vent DNA polymerase. The amplified fragment containing EcoRI and NotI restriction sites was subcloned into a predigested yeast expression vector (FIG. 3). The pPICZαA vector carries an alpha factor secretion signal sequence with a Zeocin marker for antibiotic selection. Initial transformation was done in the Top 10' host strain. The resultant clones were screened for insert and positive clones were sequenced. The plasmid was then linearized with SacI and used for homologous recombination into the yeast host strain GS 115. The transformation was carried out by the lithium chloride method as described in the Pichia expression manual. The recombinants were selected by plating on YPD plates containing 100 g/ml of Zeocin. The clones which grew on YPD/Zeocin plates were tested for expression.

The expression of mouse endostatin in large scale was carried out in 2 liter baffled shaker flasks. The overnight grown culture ($A_{600}$, 2–6) was used to inoculate 2 liter flasks. To each 2-liter flask, 500 ml of buffered glycerol medium was added. Cells were grown at 250 rpm at 30° C. until $A_{600}$, 16–20 (2 days). After two days, the cells were centrifuged at 5000 rpm for 10 minutes. Yeast were resuspended in 300–400 ml of buffered methanol induction medium. The supernatant containing the secreted recombinant protein was harvested on the second, third, and fourth day after induction. After the final harvest, the cell free supernatant was processed immediately.

*Pichia pastoris*, a methanotropic yeast strain, has many advantages of a higher eukaryotic expression system: (a) the presence of alpha factor signal sequence facilitates secretion of the expressed protein into the medium, (b) the yeast strain (GS115) secretes only very low levels of endogenous host protein which further simplifies the purification process, and (c) there is no endotoxin contamination. The vector pPICZαA was selected for expression of mouse endostatin. Initial screening was used to identify yeast clones with high levels of expression. Endostatin was expressed as a soluble protein (20 kDa) with a peak level of expression noted on the second day after induction.

Example 4
Purification of Mouse Endostatin Heparin-agarose Chromatography

Mouse endostatin binds to a heparin column through the heparin binding domain as reported by O'Reilly, et al. (O'Reilly, M. S., Boehm, T., Shing, Y., Fukai, N., Vasios, 20 G., Lane, W. S., Flynn, E., Birkhead, J. R., Olsen, B. R. & Folkman, J. (1997) Cell 88:277–285). Hence, a heparin-agarose column was used for purification. The crude supernatant containing recombinant protein was concentrated by ammonium sulfate precipitation (70/%). The precipitated protein was dissolved in 10 mM Tris buffer pH 7.4 containing 150 mM NaCl and dialyzed overnight at 4° C., with three changes at 6–8 hour intervals. The dialyzed sample was further concentrated by ultra-filtration using an Amicon concentrator (YM 10). A disposable polyprep column (Bio-Rad, Hercules, Calif., USA) was packed with heparinagarose resin and equilibrated with 10 mM Tris, 150 mM NaCl (pH 7.4). The concentrated sample was loaded on the column at a flow rate of 20 ml/hour using a peristaltic pump. The column was washed with equilibration buffer until the $A_{280}$ was<0.001 The bound proteins were eluted by a step-wise gradient of NaCl (0.3, 0.6, 1.0 and 2.0 M NaCl). The peak fractions from 0.6 M to 1.0 M were pooled and dialyzed against PBS pH 7.4. The concentration of protein was measured by the BCA assay (Pierce Chemical Co., Rockford, Ill., USA). The purification process was performed in a cold room at 4° C.

Figure 7A:
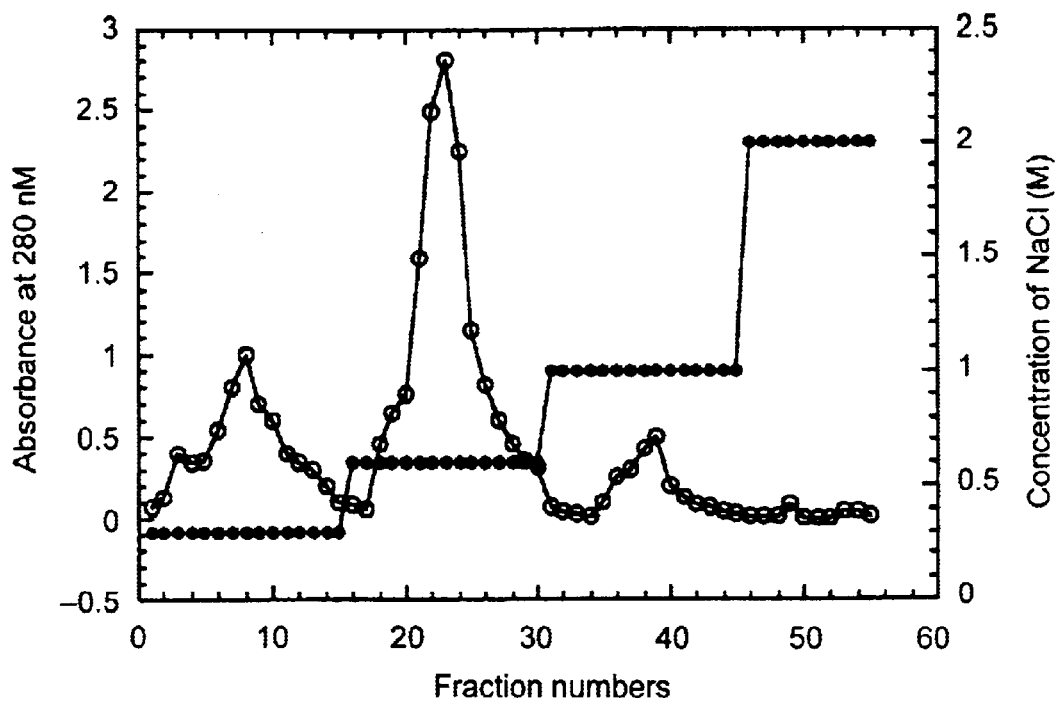
FIG. 7A shows the purification of soluble mouse endostatin expressed in yeast using a heparin-agarose column. The concentrated supernatant from one liter culture was loaded in batches. A step-wise gradient of NaCl from 0.3, 0.6, 1 and 2 M was used to elute bound endostatin from the column. The eluted fractions were collected as 2 ml per tube. (•) Concentration of NaCl. (○) Absorbance at 280 nm.
Figure 7B:
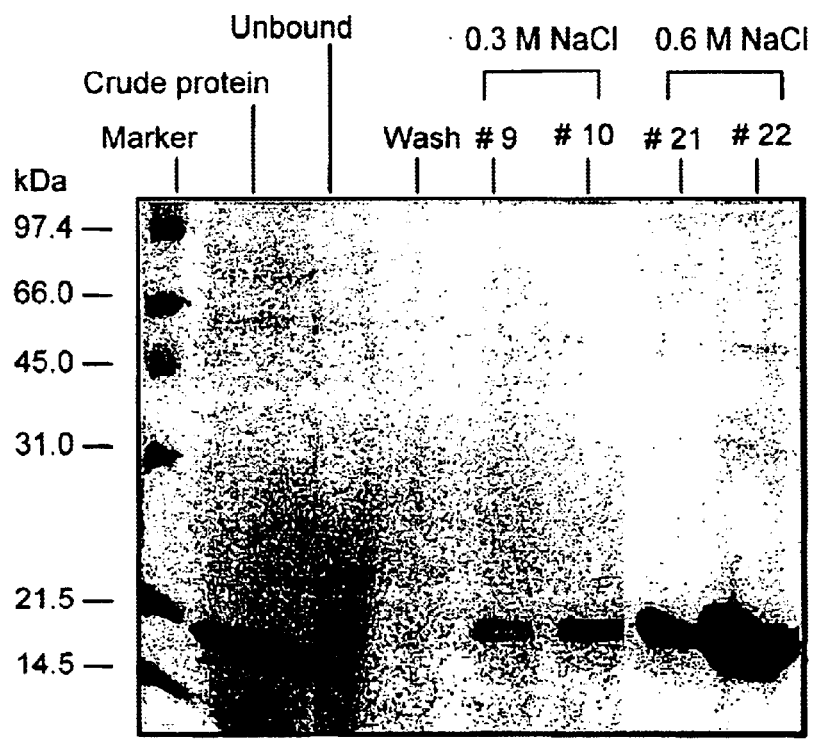
FIG. 7B shows the electrophoretic analysis of purified recombinant soluble mouse endostatin from heparin-agarose column by 12% SDS-PAGE. kDa marker-low molecular weight standards. The purified protein migrated as a single band corresponding to 20 kDa. A 10 microliter aliquot of selected fractions was used for analysis of purity of the eluted protein.

FIGS. 7A and 7B show the elution profile and SDS-PAGE analysis of purified protein. Two distinct peaks were obtained with increasing concentrations of NaCl (FIG. 7A). The first peak at 0.3 M NaCl was small when compared to the major peak at 0.6 M NaCl. Elution with 1 M NaCl did not show a distinct peak. Most of the endostatin protein bound to the column as shown by the lack of the protein in the flow-through fraction (FIG. 7B). The recombinant protein bound tightly to the column and washing with the low salt Tris buffer removed other yeast derived proteins. A small amount of endostatin was eluted from the column at 0.3 M NaCl (FIG. 7B). At 0.6 M NaCl, all the bound protein was eluted (FIG. 7B). The protein eluted from the 0.3 M NaCl fraction had a trace amount of endostatin but was contaminated with other host derived high molecular weight protein. The purified protein migrated at 20 kDa, and upon reduction migrated at 22 kDa. The protein fractions eluted at 0.6 M NaCl alone were pooled, concentrated and dialyzed against PBS pH 7.4. The purified protein was further separated by FPLC using a Superose 12 size separation column. The elution profile from this column showed a single peak. SDS-PAGE analysis showed the presence of single discrete band corresponding to endostatin. The level of expression was estimated to be in the range of 15–20 mg/L culture. The recombinant protein bound to the heparin-agarose column and was eluted at 0.6–1 M NaCl concentration. These data suggest that the protein expressed by the yeast was folded properly, because it had properties comparable to the baculovirus expressed endostatin.

Example 5
Cloning and Expression of His.Endostatin in the Pichia Expression System The coding region of the mouse endostatin construct in the pET expression vector is preceded by a His.Tag (10 histidine residues). By DNA-PCR the coding region including the His.Tag sequence was shuttled into pPICZαA vector. The linearization and recombination into the yeast host strain GS115 were done as described above. The cell free medium was precipitated with ammonium sulfate (70% saturation). The precipitated proteins were dissolved in 50 mM sodium phosphate buffer pH 8.0 containing 300 nM NaCl and dialyzed in the same buffer at 4° C. following three changes at 6–8 hour intervals. A nickel agarose column (Ni-NTA) was used for purification of His.endostatin recombinant protein. The purification was performed as described in the QIAexpressionist manual. The bound proteins were eluted with a step-wise imidazole gradient (10 mM, 25 mM, 50 mM, and 100 mM).

Figure 8A:
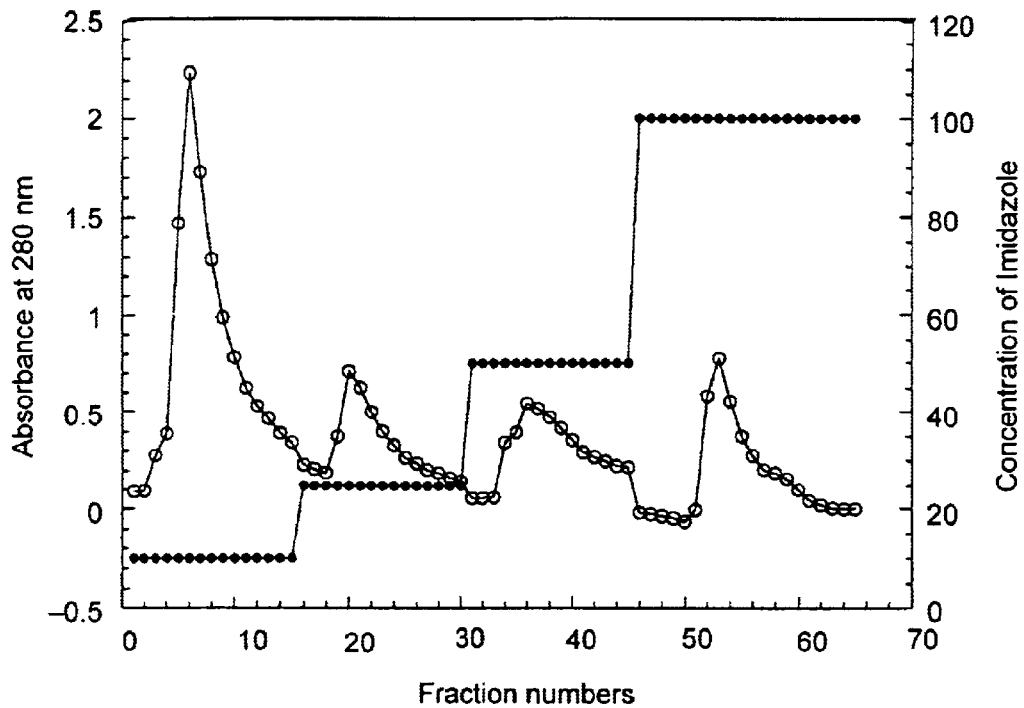
FIG. 8A shows the purification of soluble His.endostatin expressed in yeast using a Ni-NTA column. Elution profile from the Ni-NTA column. A step-wise gradient of imidazole (10, 25, 50 and 100 mM) was used to elute the bound proteins from the column. (•) Concentration of imidazole. (○) Absorbance at 280 nm.
Figure 8B:
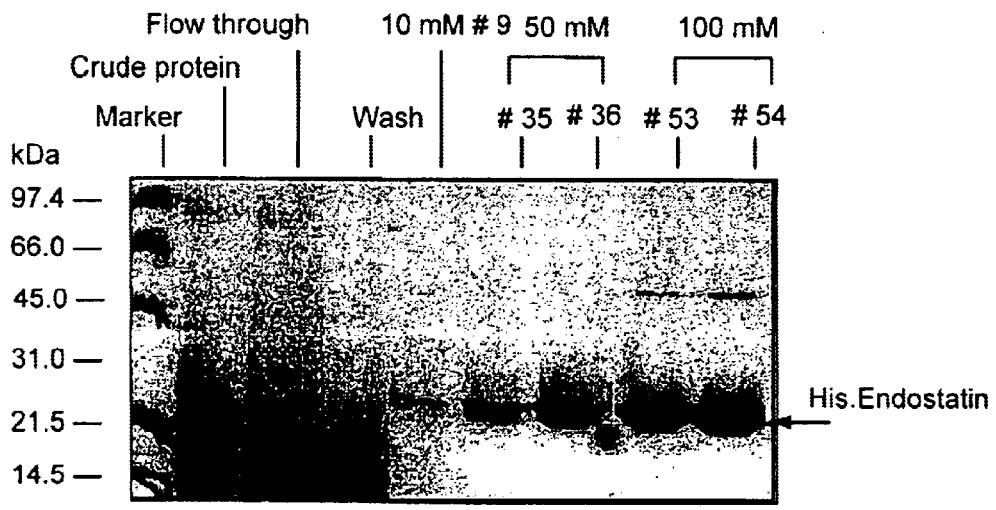
FIG. 8B shows the 12% non-reducing SDS-PAGE of selected fractions. kDa marker-low molecular weight standards. The purified recombinant His.endostatin migrated as a single band corresponding to 22–24 kDa in 50 mM imidazole, whereas 100 mM elution showed a trace amount of higher molecular weight complexes corresponding to 44–46 kDa.

The elution profile of His.endostatin from the Ni-NTA column showed that the recombinant protein bound tightly to the column (FIGS. 8A and 8B). The yeast derived host proteins in the culture supernatant did not bind to the column and were removed during the wash. Bound proteins were eluted by a stepwise gradient of imidazole (FIG. 8A). The non-specifically bound host derived proteins eluted with the addition of 10 mM imdiazole. At 25 mM imidazole, a small fraction of the recombinant protein was eluted along with proteins of higher molecular weight. Final elution with 100 mM imidazole showed a distinct peak. SDS-PAGE analysis (FIG. 8B) of the eluted proteins showed that the flowthrough fraction did not contain any endostatin, indicating that most of the protein bound to the column. Increasing the concentration of imidazole to 10 mM and 25 mM resulted in the elution of non-specific protein. A protein with a molecular weight of 22 kDa was seen at 100 mM along with a smaller amount of protein corresponding to 44–46 kDa. The concentration of purified protein was determined by the BCA method: The level of expression was estimated at 15 mg/L culture.

Example 6
Characterization of Recombinant Endostatin

To further characterize the recombinant protein, N-terminal microsequencing was carried out for seven cycles at the Harvard microsequencing facility. In addition, a polyclonal antiserum to mouse recombinant endostatin was raised by immunizing a rabbit with 10 micrograms of purified protein derived from the Pichia expression system. Recombinant endostatin expressed from bacteria and yeast system were separated on 12% SDS-PAGE. The proteins were transferred to PVDF membrane by semi-dry transfer (Trans-blot, Bio-Rad, Hercules, Calif., USA). The primary antiserum was diluted to 1:4000 in 1×TBS buffer containing 5% non-fat dry milk. Goat anti-rabbit IgG/HRP conjugate was used as secondary antibody (1:5000). Immunoreactivity was detected by chemiluminescence (Pierce Chemical Co., Rockford, Ill., USA).

The sequence analysis showed that the yeast alpha factor signal peptide was processed and cleaved at alanine. The first seven residues (EFHTHQD) of the purified protein after signal peptide cleavage matched exactly the known sequence of endostatin protein (Rehn, M., Hintikka, E., & Pihlajaniemi, T. (1994) J. Biol. Chem. 269:13929–13935). The first two residues (EF) were derived from linker sequence.

Example 7
Endostatin Polyclonal Antobodies and Western Blot Analysis

A polyclonal antibody was raised against purified mouse endostatin derived from the yeast expression system. The purified endostatin expressed from the bacterial and yeast expression systems were run under reducing and non-reducing conditions. The size of the protein estimated from the western blot ranges from 22–24 kDa. In addition, the recombinant His.endostatin from yeast and bacteria was probed with a Penta His.monoclonal antibody (QIAGEN, Calif.). The monoclonal antibody showed positive response only with the His.endostatin whereas native endostatin did not show any immunoreactivity. This confirmed the presence of the His.Tag in the recombinant protein. The antiserum did not show any cross reactivity to human or mouse angiostatin, demonstrating some degree of immunoreactivity specific to endostatin. Immunoreactivity of the polyclonal antibody was also observed with EM 1 and EM 2 proteins.

Example 8
Endothelial Proliferation Assay

The biological activity of recombinant endostatin was determined by in vitro. The anti-proliferative effect of endostatin produced in the yeast system was measured by $^3$H-thymidine incorporation using bovine pulmonary arterial endothelial cells (C-PAE). The cells were plated in 24 well fibronectin-coated plates (10 micrograms/ml) at 12,500 cells per well in 0.5 ml DMEM containing 2% FBS. After a 24 hour incubation at 37° C., the medium was replaced with fresh DMEM and 2% FBS containing 3 ng/ml of bFGF (R & D Systems, Minneapolis, Minn., USA) with or without recombinant mouse endostatin. The cells were pulsed with 1 Ci of $^3$H-thymidine for 24 hours. Medium was aspirated and the cells were washed three times with PBS. The cells were then solubilized by addition of 1.5 N NAOH (100 microliter/well) and incubated at 37° C. for 30 minutes. Cell-associated radioactivity was determined with a liquid scintillation counter.

Figure 9:
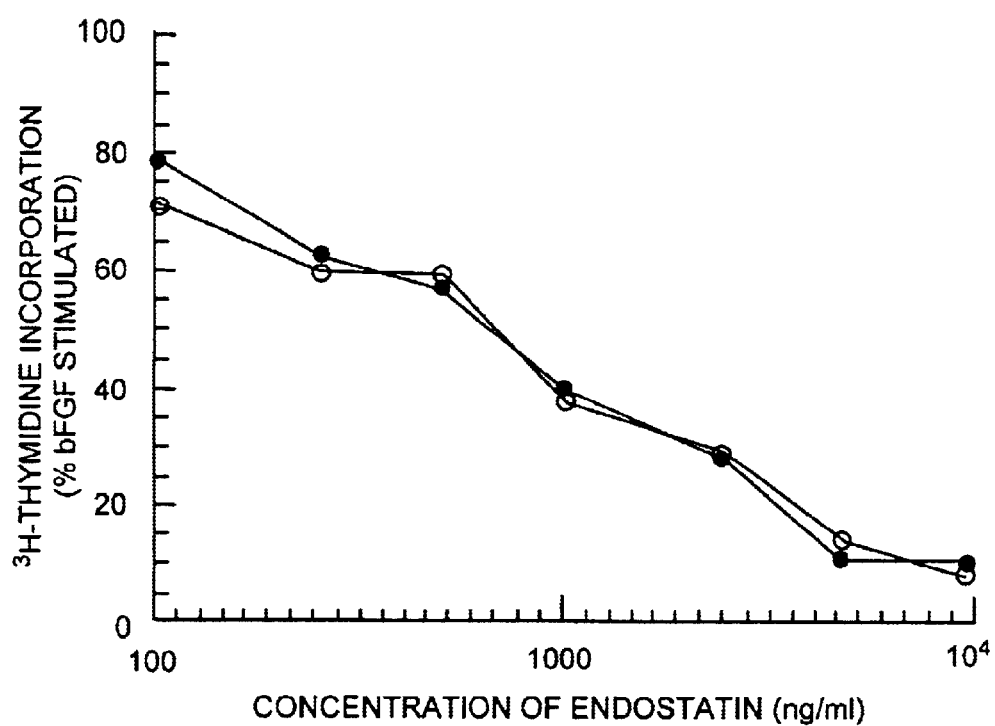
FIG. 9 shows the results of an endothelial cell proliferation assay. The purified mouse endostatin expressed from yeast was tested for its ability to inhibit (methyl-$^3$H) thymidine incorporation in C-PAE cells. bFGF at 3 ng/ml was used as a stimulus. Each value is a mean of triplicate cultures from a representative experiment and error bars represent standard deviation. DNA synthesis in the control culture was considered as 100%. The experiment was repeated more than 4–5 times under identical conditions.

A dose dependent inhibition of bFGF induced proliferation was seen with purified endostatin (FIG. 9). The inhibition range (30–94% of control) was seen with increasing concentrations of endostatin (0.1 micrograms/ml to 10.0 micrograms/ml), with an $ED_{50}$ value in the range of 600–700 ng/ml. A similar inhibitory effect on C-PAE cells was seen when His.endostatin from yeast was tested as described herein.

The biological activity of recombinant endostatin expressed from the yeast system was comparable to the protein expressed from the baculovirus system with regard to the $ED_{50}$ value. With baculovirus derived endostatin, maximum inhibition was observed at 600 ng/ml or greater. The yeast derived endostatin had a $ED_{50}$ value of 600–700 ng/ml. Also, endostatin at high doses (>100 micrograms/ml) did not inhibit the growth of the 786-0 cell line.

Example 9
Endothelial Migration Assay

To determine the ability of recombinant endostatin to block migration of ECV304 cells towards bFGF, a migration assay was performed using different concentrations of endostatin with bFGF as a stimulus. 12 well Boyden chemotaxis chambers (Neuro Probe, Inc., Cabin John, Md., USA) were used, with a polycarbonate membrane (25×80 mm PVD free, 8 pores, Poretics Corp., Livermore, Calif.). The non-specific binding of growth factor to the chambers was prevented by coating the chambers with a solution containing 0.5% gelatin, 1 mM $CaCl_2$ and 150 mM NaCl at 37° C. overnight. ECV304 cells were grown in 10% FBS containing 5 ng/ml Dil (1,1'-dioctadecyl-3,3,3',3'-tetramethylindocarbocyanine perchlorate DilC18. Molecular Probes, Eugene, Oreg.) overnight and washed with PBS containing 0.5% BSA. Following trypsinization, the cells were counted using a Coulter-Counter Z1 (Luton, U.K.) and diluted to 300,000 cells/ml in Medium 199 containing 0.5% FBS. The lower chamber was filled with Medium 199 containing 25 ng/ml bFGF. The upper chamber were plated with 15,000 cells/well along with different concentrations of recombinant endostatin. Cells were allowed to migrate for 4 hour at 37° C. At that time, the cells on the upper surface of the membrane were removed with a cell scraper and the (migrated) cells on the lower surface were fixed in 3% formaldehyde and washed in PBS. Images of the fixed membrane were obtained using fluorescence microscopy at 550 nM with a digital camera and the number of cells on each membrane was determined using the OPTIMAS (version 6.0) software (Media Cybernetics, L.P., Silver Spring, Md., USA).

Figure 10:
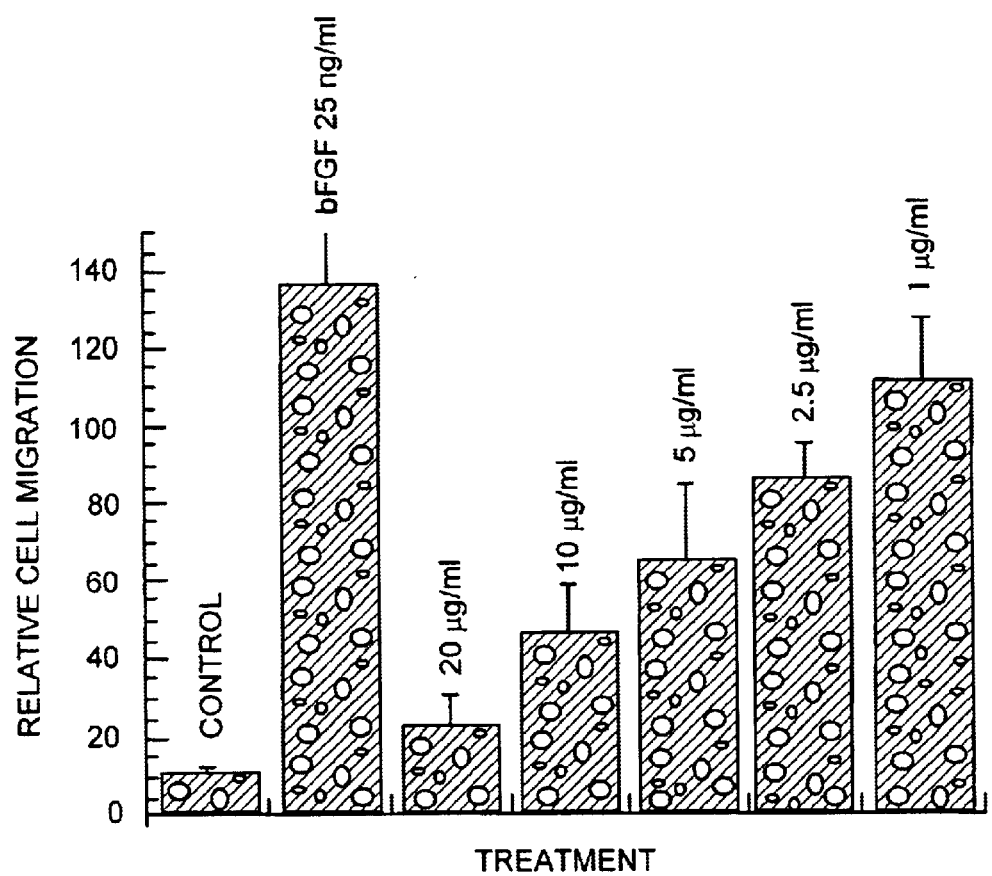
FIG. 10 shows the inhibition of migration of endothelial cells with different concentration of endostatin. Each treatment was done in duplicate. In each well, the number of cells migrated were counted in three different areas and the average obtained. Each value is a mean from representative experiments and error bars represent standard deviations.

Addition of endostatin resulted in a dose-dependent inhibition of proliferation that was maximal at 20 micrograms/ml (FIG. 10). At a concentration less than 1 micrograms/ml, marginal inhibition of migration was seen. At 10 micrograms/ml, inhibition of endothelial cell migration was 60%.

Example 10
Cam Assay

The ability of mouse endostatin to block bFGF induced angiogenesis in vivo was tested using the chorioallantoic membrane (CAM) assay. Fertilized white Leghorn chicken eggs (SPAFAS, Inc., Norwich Conn.) were opened on 100 mm$^2$ petri dishes and allowed to grow until day 11 in a humidified incubator at 38° C. Pellets containing vitrogen (Collagen Biomaterials, Palo Alto, Calif.) at a concentration of 0.73 mg/ml and supplemented with: a) vehicle alone; b) VEGF (250 ng/pellet); c) VEGF and endostatin (20 and 0.5 micrograms/pellet, respectively); d) bFGF (50 ng/pellet); and e) bFGF and endostatin (20 and 0.5 micrograms/pellet, respectively) were allowed to polymerize at 37° C. for 2 hours. The pellets were placed on a nylon mesh and oriented on the periphery of the CAM. Embryos were returned to the incubator for 24 hours. Invasion of new capillaries on the collagen mesh was assessed by injection of FITC-dextran into the circulation of the chicken embryo. At the end of the experiment, the meshes were dissected and evaluation of vascular density was done using the program NIH Image 1.59. Assays were performed in triplicate and four independent experiments were conducted.

Figure 11A:
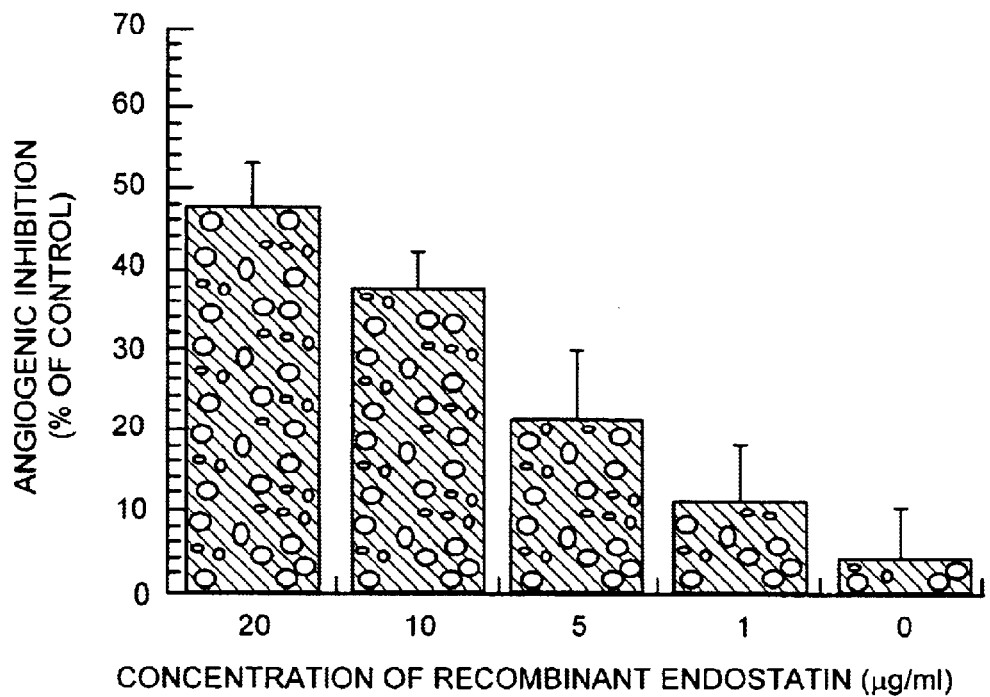
FIGS. 11A and 11B show the inhibition of VEGF (11A) and BFGF (11B) mediated angiogenic response by endostatin. Different concentrations of endostatin were added on the nylon mesh and vessel growth was determined as described herein. All the counts were normalized to the negative control.
Figure 11B:
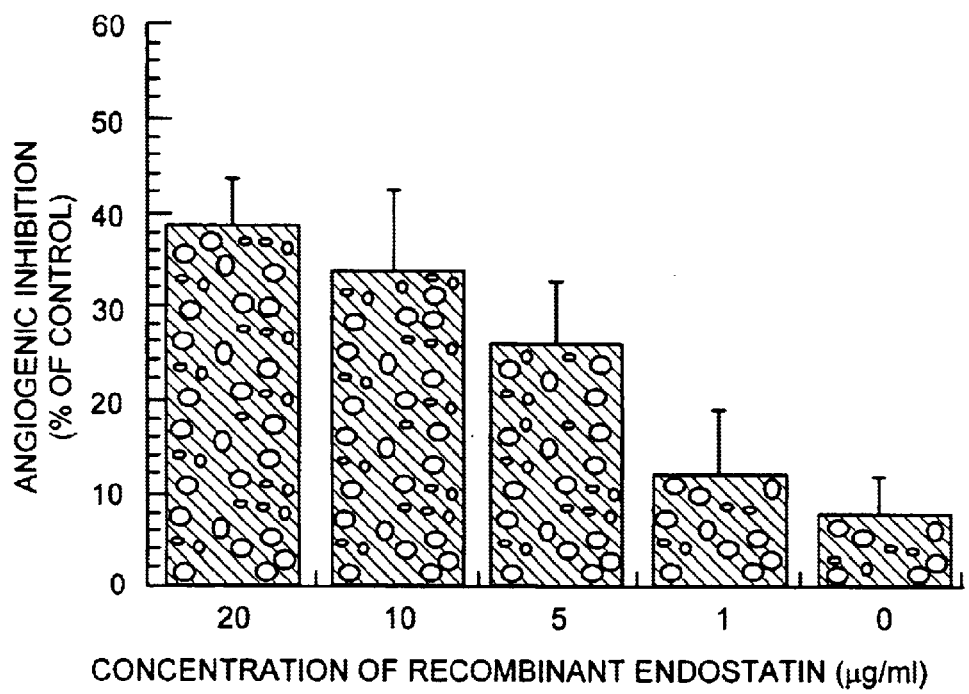

Endostatin was able to suppress the angiogenic response mediated by both bFGF and VEGF (FIGS. 11A and 11B). The inhibition was dose-dependent with a plateau at 5 micrograms/mesh. Blocking of the VEGF-response was somewhat more effective (47%) than the suppression of the bFGF-response (39%). In the CAM assay, endostatin at 20 micrograms/disc inhibited angiogenesis induced by bFGF. The effect of endostatin on the CAM assay showed stronger potency on a molar basis than the inhibitors thrombospondin-I (35), fumagillin (AGM 1470) or antibodies against the integrin$_{v3}$ (Iruela-Arispe, unpublished observations) in the same assay. Our studies on endothelial cell migration are novel in providing an additional mechanism of action for endostatin and a new in vitro assay for its efficacy.

Example 11
Neutralization of Endostatin Inhibitory Effect

The specificity of endostatin inhibitory effect was demonstrated by neutralization studies using endothelial proliferation and CAM assays. Briefly, in the endothelial proliferation assay, the endostatin was pre-incubated with polyclonal antiserum and then added to the C-PAE cells. Pre-immune serum was used as negative control. In addition, purified IgG was also used as a control. The cells were then pulsed with $^3$H-thymidine for 24 hours and cell associated radioactivity was measured as described previously. For the CAM assay, endostatin (10 micrograms) and antiserum (50 micrograms) were pre-incubated overnight end-over-end at 40° C. prior to the preparation of the pellets. Controls for these experiments included IgG alone and preimmune serum alone. Evaluation of the angiogenic response was determined as indicated above.

Figure 12:
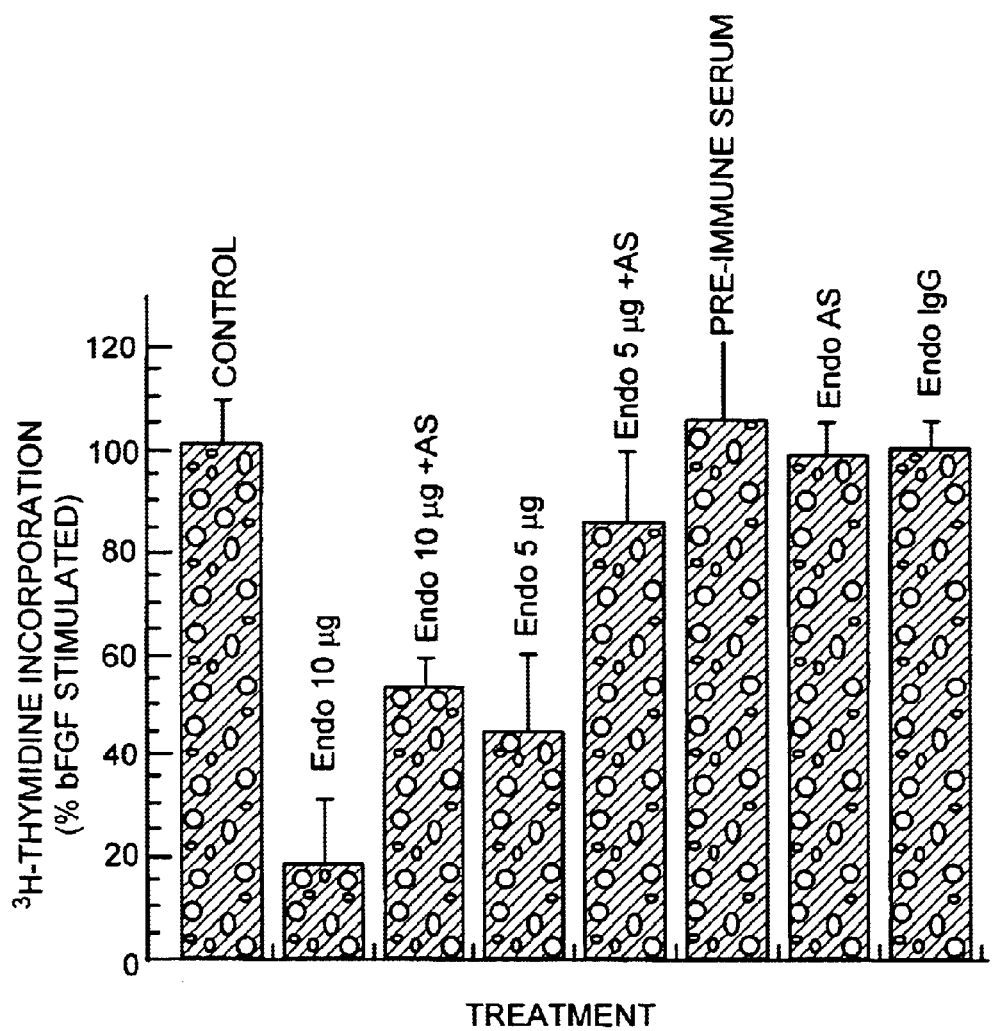
FIG. 12 shows the neutralization of the inhibitory effect of mouse endostatin by polyclonal antiserum in the endothelial proliferation assay. A 24 well fibronectin-coated plate was seeded with C-PAE cells at 24,500 cells/well. Recombinant endostatin (10 micrograms/ml and 5 micrograms/ml) was mixed with excess of polyclonal antiserum to endostatin or pre-immune or control IgG for 1 h at RT. The mixture was then added to C-PAE cells in the presence of 3 g/ml bFGF. DNA synthesis was measured by adding 1 ci/well $^3$H-thymidine. Each value is a mean from triplicate culture and error bars represent standard deviation.

FIG. 12 demonstrates that the inhibitory effect of endostatin can be suppressed by incubation with specific antiserum. Anti-endostatin blocked the suppressive effect by 95%. The pre-immune serum alone did not have a stimulatory effect nor did normal rabbit IgG.

Example 12
Inhibition of Primary 786-0 Tumor in Nude Mouse Model

Six-to eight-week-old male beige nude mice were injected sub-cutaneously in the right flank with 2 million 786-0 cells in a 100 microliter volume. Tumors appeared approximately two weeks after implantation. Tumor size was measured using calipers and tumor volume was calculated using a standard formula. The tumor volume ranged from 350 mm$^3$ to 400 mm$^3$. The animals were randomized and each group had five mice with tumor size comparable within and among the groups. Treatment was started with recombinant endostatin (bacterial or yeast versions) with each mouse receiving 10 mg/kg body weight of recombinant protein daily, administered for a period of ten days via intra peritoneal injection. Control animals received PBS each day. Tumor size in all groups was measured on alternate days and tumor volume was calculated. The activity and behavior of the animals were monitored during this period. The treatment was terminated on day 10 and animals were sacrificed and tumors from each mouse removed and fixed in 10% buffered formalin.

For the mutant study, each mouse received 20 mg/kg body weight of the protein daily for two weeks intraperitoneally. The tumor volume ranged from 150–200 mm$^3$. Wild type endostatin, also produced in the pET28(a) vector, was given at 20 mg/kg body weight for the experiment as a positive control and PBS was given as a negative control.

Figure 13A:
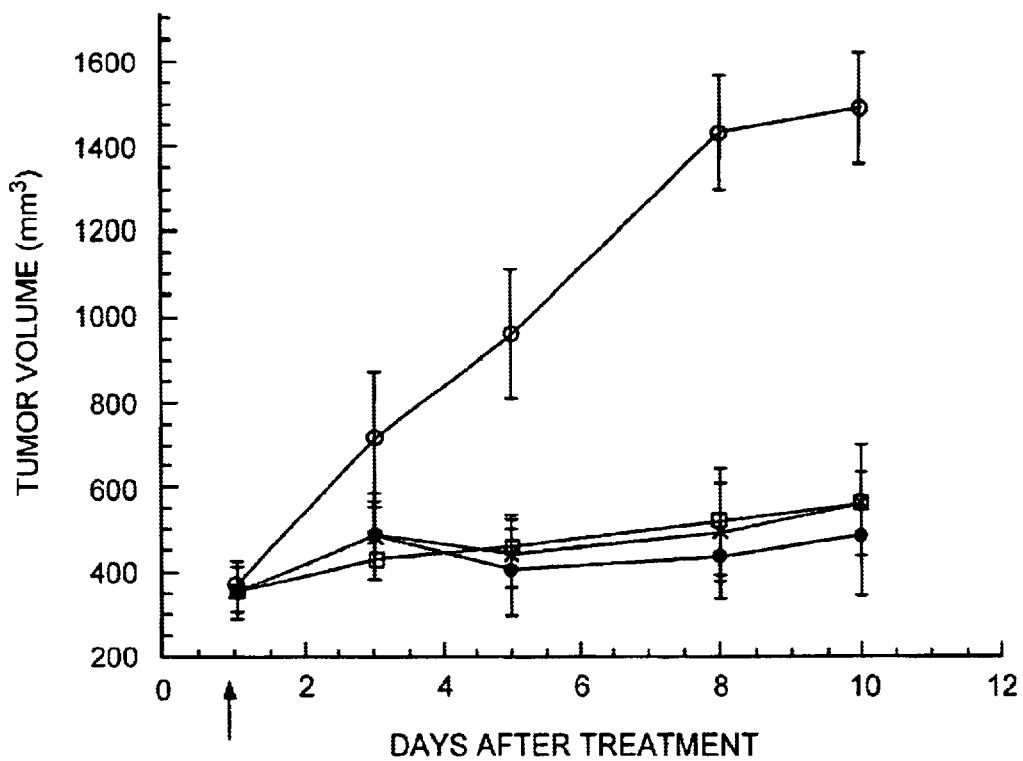
FIG. 13A shows the inhibition of 786-0 tumor growth by systemic treatment with recombinant endostatin. Athymic nude mice carrying 786-0 tumor cells were treated with recombinant endostatin when the tumor volume was approximately 350–400 mm$^3$. Intra-peritoneal injection of endostatin was given at 10 mg/kg on a daily basis. The tumor size was measured on alternate days using a caliper and tumor volume was calculated using the standard formula width$^2$×length×0.52. Each time point represents the average from five different mice in each group and the error bar represents S.E.M.; (○) control PBS; (•) native endostatin from yeast, (X) His.endostatin from yeast; (□) His.endostatin from bacteria.

On the fifth day after treatment there was a difference between control (963 mm$^3$) and treated (endo yeast, 405 mm$^3$; endo bacteria, 442 mm$^3$, and His.endo, 462 mm$^3$). A 2.5-fold decrease in tumor volume was observed on the fifth day after treatment between the controls and treated (FIG. 13A). The growth of the tumor was suppressed in all the treatment groups: a slower growth rate was seen compared to the control group, Bacterial (His.Tag) or yeast derived (with or without His.Tag) endostatin at a dose of 10 mg/kg all worked equally well. On the tenth day after treatment, the tumor volume in the control animal was 1490 mm$^3$, whereas in the treated group it was found to be in the range of 480–570 mm$^3$ (p<0.005). The administration of endostatin did not inhibit the growth of the tumor completely; but the growth of the tumor slowed, maintaining a marginal increase in tumor volume during that period.

Figure 13B:
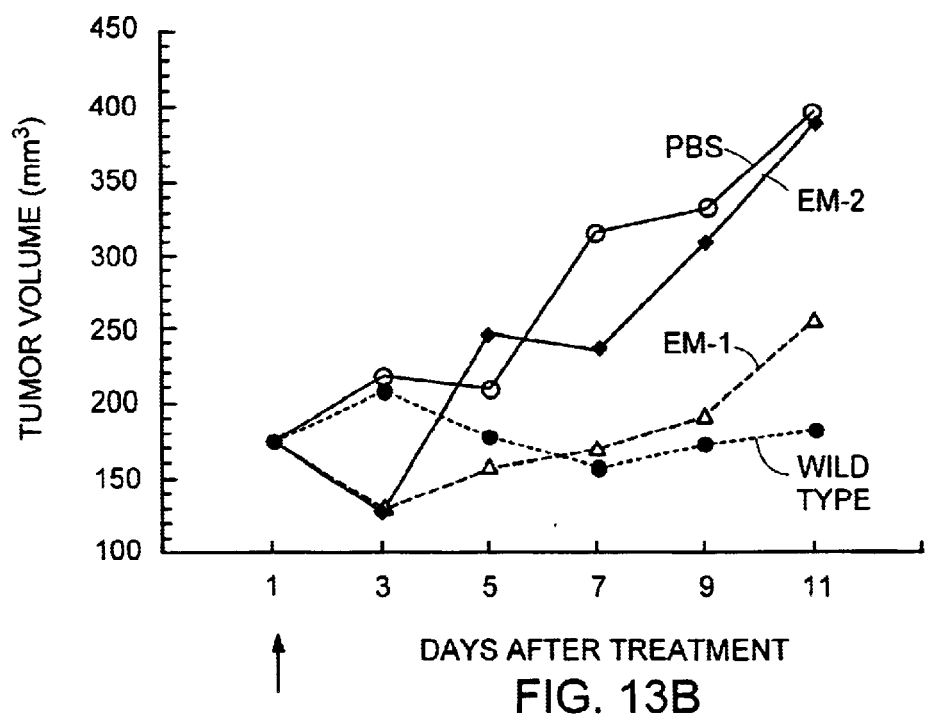
FIG. 13B shows athymic nude mice carrying 786-0 tumor cells were treated with recombinant endostatin when the tumor volume was approximately 150–200 mm³. Intraperitoneal injection of endostatin was given at 20 mg/kg on a daily basis. The tumor size was measured on alternate days using a caliper and tumor volume was calculated using the standard formula width²×length×0.52. Each time point represents the average from five different mice in each group. (○) control PBS; (•) His.endostatin from bacteria; (Δ) His.EM 1 from bacteria; (♦)His.EM 2 from bacteria.

A second set of experiments with endostatin and mutants EM 1 and EM 2 at a dosage of 20 mg/kg body weight were tested in an RCC model. The tumor volumes after 11 days of treatment are shown in FIG. 13B. Nine days after treatment, the difference between groups was apparent. On the eleventh day after treatment, the tumor volume in the control group (397 mm$^3$) is approximately twice the size of the two treated groups of endostatin (182 mm$^3$) or EM 1 (259 mm$^3$). However, on the same day, the tumor volume of the EM 2 treated group (389 mm$^3$) was similar to that of the control group (397 mm$^3$). Significance was at the 90% confidence level between the EM 2 and endostatin groups and 95% confidence level between endostatin and control groups. Dropping the value of the largest and smallest tumors on day 11 in each group increased the confidence level to 95% between EM 2 and EM 1 and between EM 2 and endostatin. The EM 1 protein therefore, retained the native biological activity of endostatin, whereas EM 2 did not. The marked difference in efficacy between the two mutant endostatin proteins also show that endostatin and not a possible contaminant is the active molecule giving an anti-angiogenic effect. Moreover, the mutant protein data points to the importance of 8 residues (SYIVLCEE) surrounding and including the last cysteine as critical for endostatin activity.

With regard to its ability to inhibit the growth of a primary tumor, irrespective of the source of protein either non-refolded or native protein had comparable inhibitory profile. Moreover, the presence of a His.Tag sequence in yeast derived protein did not affect the biological activity. Though there was significant difference in tumor volume between control and treated mice, the tumors in the treated group continued to grow slowly during the treatment period. On the tenth day after treatment, when administration of endostatin was stopped, the tumor grew rapidly and within a week the average size of the tumors was comparable to controls. In the first study with relatively large tumor volume, we were unable to induce tumor dormancy. The effects of endostatin (and its mutants) were subsequently tested on tumors ranging from 150–200 mm$^3$ and also increased the dosage to 20 mg/kg body weight. Under these conditions tumor growth was inhibited, although tumor dormancy was not observed.

Example 13

Cloning, Expression, and Purification of Human Endostatin in *Pichia Pastoris*

The sequence encoding the carboxy terminal portion of human collagen XVIII was amplified from a human fetal kidney (HFK) cDNA library using Vent DNA polymerase. The primers used were: 5'-TTT GAA TTCGCC CAC AGC CAC CGC GAC TTC CAG CCG GTG CTC CAC-3' (SEQ ID NO:12) and 5'-AAA AGC GGCCGCCTA CTT GGA GGC AGT CAT GAA GCT GTT CTC AAT-3' (SEQ ID NO:13) based on human collagen XVIII sequence (Oh et al. (1994) *Genomics* 19:494–499). Amplification was carried out for 30 cycles with the following parameters: 94° C. for denaturation, 60° C. for annealing, and 72° C. for extension, each for 1 minute. The amplified fragment of 549 bp was purified using the QIAquick purification kit (Qiagen, Hilden, Germany), digested with EcoRI and NotI (these restriction sites are underlined in the above primers). The resulting fragment was ligated into a pre-digested yeast expression shuttle plasmid (pPICZαA, FIG. 1), and transformed into *Pichia pastoris*. Positive clones were sequenced on both strands. Transformation, recombination and selection were carried out as described for mouse endostatin by Dhanabal et al. (1999) (*Biochem:. Biophys. Res. Commun.*) 258:345–52), and in PCT/US98/26057 Mutants of Endostatin, 'EM 1' Having Anti-Angiogenic Activity and Methods of Use Thereof by Vikas P. Sukhatme, filed Dec. 8, 1998, the entire teachings of incorporated herein by reference.

The expression of human endostatin in large scale was carried out in 2-liter baffled shaker flasks as described for mouse endostatin, and the supernatant containing secreted recombinant protein was processed as described by Dhanabal et al. (1999) (*Biochem. Biophys. Res. Commun.* 258:345–52), and in PCT/US98/26057, "Mutants of Endostatin, 'EM 1' Having Anti-Angiogenic Activity and Methods of Use Thereof" by Vikas P. Sukhatme, filed Dec. 8, 1998, and in U.S. Ser. No. 09/589,777, "Anti-Angiogenic Peptides and Methods of Use Thereof", by Vikas P. Sukhatme, filed Jun. 8, 2000, the entire teachings of both of which are incorporated herein by reference. It was concentrated by 70% ammonium sulfate precipitation. The precipitated protein was dialyzed against 50 mM sodium phosphate buffer, pH 7.4 containing 50 mM NaCl. The purification of human endostatin was carried out using a heparin-agarose column. The protein sample was loaded on the column using a peristaltic pump. The column was washed with 50 mM phosphate buffer containing 50 mM NaCl followed by the same buffer containing 100 mM NaCl. Bound proteins were eluted by stepwise elution using 0.2 M and 1 M NaCl. The peak fractions from the 1M NaCl elutant were pooled and dialyzed against PBS buffer (pH 7.4). Protein concentration was measured by the BCA assay (Pierce Chemical Co., Rockford, Ill., USA).

Figure 14A:
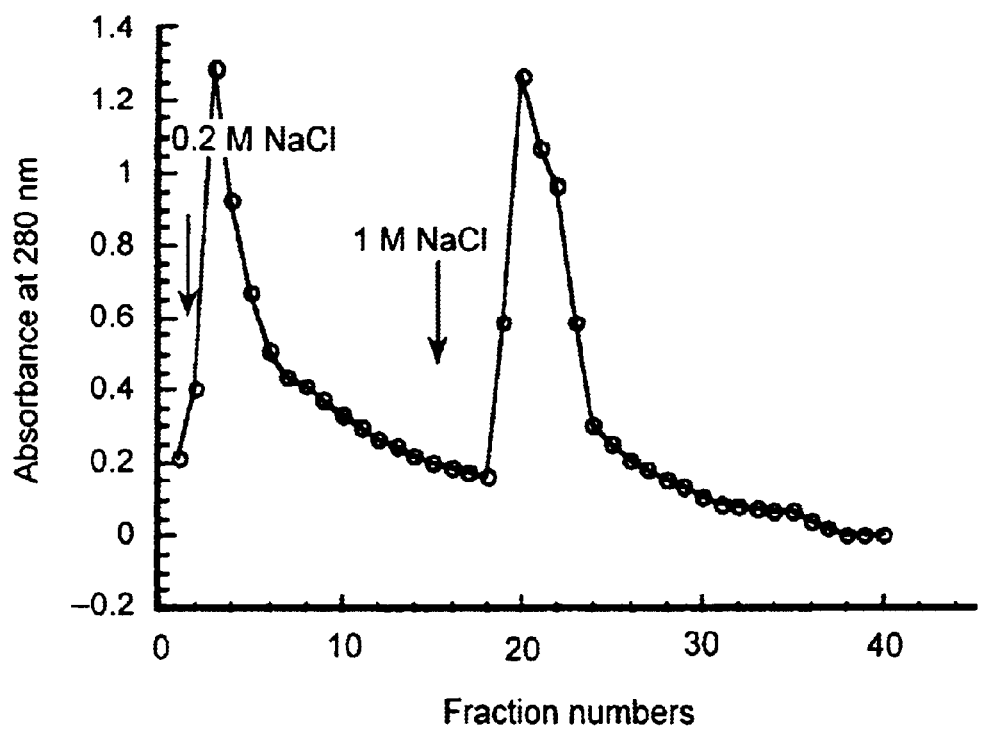
FIG. 14A shows a graph showing the purification of soluble human endostatin expressed in Pichia pastoris using a heparin-agarose column. Fraction numbers are displayed along the x-axis, and Absorbance at 280 nm is shown on the y-axis. A step-wise gradient of NaCl from 0.2 M to 1.0 M was used to elute bound endostatin from the column. The arrows indicate the concentration of NaCl used for elution purposes (0.2 M NaCl starting at fraction 1, and 1 M NaCl starting at approximately fraction 15–16). The eluted protein was collected in fractions of 2 ml. Two distinct peaks were observed, one at about fraction 4 and the other at about fractions 20 to 23.
Figure 14B:
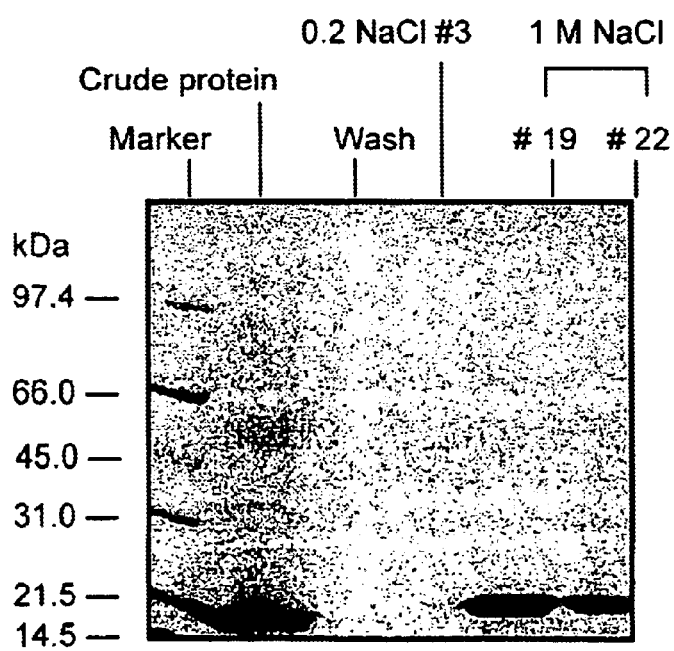
FIG. 14B shows an electrophoretic analysis of purified recombinant human endostatin from a heparin-agarose column by an 12% SDS-PAGE gel. Sizes in kDa are on the left. Six lanes are shown. Lane 1 contains marker, lane 2, crude protein; lane 3, wash; lane 4, fraction 3, eluted under 0.2 M NaCl; lanes 5 and 6, the elutions from fractions 19 and 20, respectively, which were eluted under 1 M NaCl.
Figure 15A:
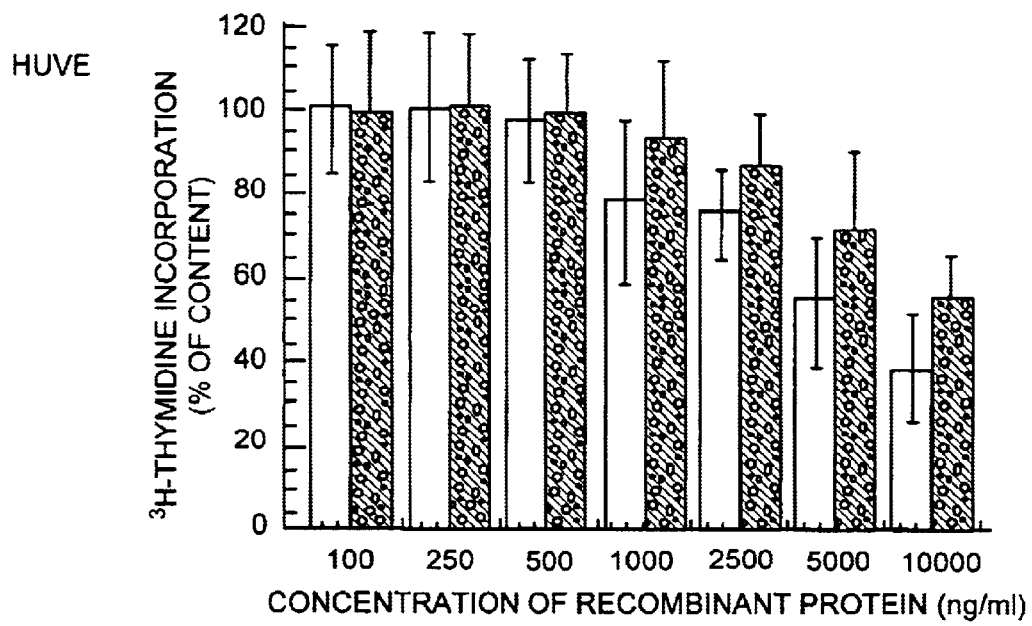
FIGS. 15A and 15B are bar graphs showing endostatin-mediated inhibition of endothelial cell proliferation in HUVE cells (FIG. 15A) and HMEV-L cells (FIG. 15B). The x-axis of each graph shows the concentration of recombinant protein in ng/ml, and the y-axis shows ³H-thymidine incorporation as a percentage of the control. Light and shaded bars represent human and mouse endostatin, respectively.
Figure 15B:
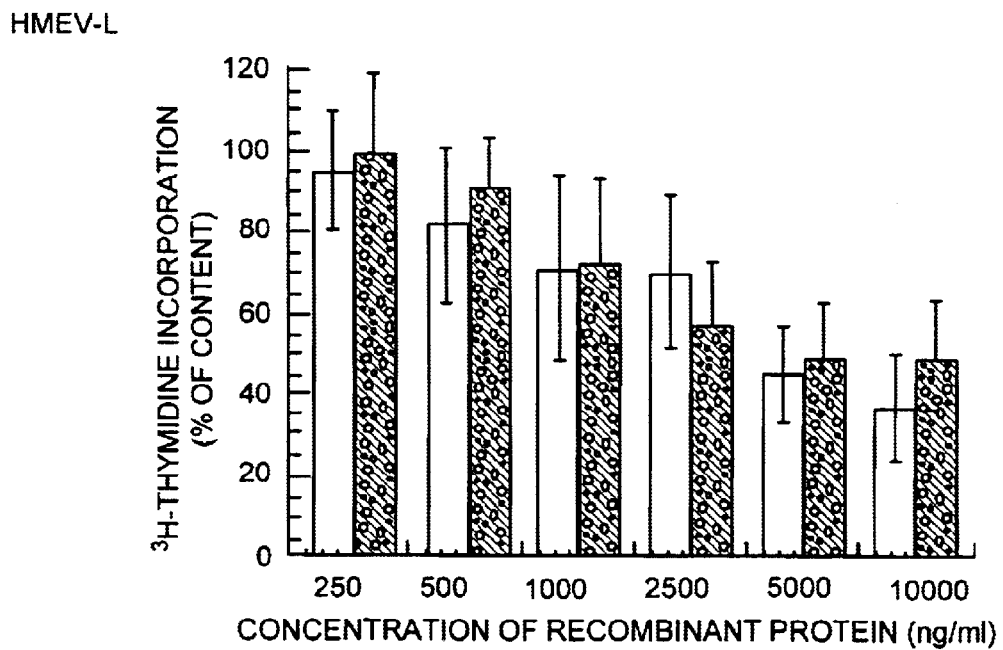

Initial small scale expression showed a maximum level of expression on the second day after induction. Endostatin was expressed as a soluble protein 20 kDa. A heparin-agarose column was used for endostatin purification. FIGS. 14A and 14B show the elution profile and SDS-PAGE analysis, respectively of the purified protein. In this study, human endostatin bound less efficiently to the heparin-agarose column, as compared to mouse endostatin. Hence, the binding was performed in 50 mM NaCl followed by washes at 0.1 M NaCl; final elution was performed with 0.2 M NaCl and 1 M NaCl. Two distinct elution peaks were observed. A 10 ml aliquot from selected fractions was used for analysis of purity of the eluted protein. The crude protein was relatively pure with some host-derived protein as contaminants. Trace amounts of protein were eluted from the column at 0.1 M NaCl. Protein eluted from the 0.2 M NaCl fraction also had a trace amount of endostatin, despite the $A_{280}$ reading. The protein eluted at 1 M NaCl was relatively pure and migrated on a 12% SDS-PAGE gel at 20 kDa which upon reduction migrated more slowly. The protein fractions eluted at 1 M NaCl alone were pooled, concentrated and dialyzed against PBS, pH 7.4. This pool was further size separated using a Superose 12 column (FPLC), from which a single elution peak was obtained. The level of expression was estimated by the BCA assay to be approximately 10 mg/L culture.

Example 14

Characterization of Human Endostatin

Initial characterization of human endostatin was done by N-terminal microsequencing for eight cycles, and showed proper processing of the yeast alpha factor signal peptide. The first eight residues (EFAHSHRD) matched exactly the published sequence of endostatin protein, with the first two residues (EF) derived from linker sequence. Sequencing of both the strands matched completely the published sequence of human collagen XVIII. The human and mouse endostatin protein show 85% identity and 93% similarity at amino acid level, demonstrating a high degree of homology and structural conservation (Sasaki et al. (1998) *Embo J.* 17:4249–56). All of the cysteine residues are completely conserved, as well.

Example 15

Western Blot Analysis

The immunoreactivity of human endostatin to purified rabbit polyclonal antibody was analyzed by western blot. Purified polyclonal antibody (IgG) raised against mouse endostatin was used to evaluate its reactivity to human endostatin. The polyclonal antiserum to mouse recombinant endostatin was raised by immunizing a rabbit with 10 micrograms of purified protein that was also derived from the Pichia expression system. Recombinant endostatin expressed from the yeast system was separated on a 12% SDS-PAGE gel. The proteins were transferred to PVDF membrane by semi-dry transfer (Trans-blot, Bio-Rad). The primary antiserum was diluted to 1:4000 in 1× TBS buffer containing 5% non-fat dry milk. Goat anti-rabbit IgG/HRP conjugate was used as a secondary antibody (1:5000). Immunoreactivity was detected by chemiluminescence Pierce Chemical Co., Rockford, Ill., USA).

Results show that the immunoreactive bands corresponding to mouse and human endostatin. Signal detected from 300 ng of human endostatin was equivalent to 100 ng of mouse endostatin. The size of the protein estimated from the western blot was 20 kDa. No signal was seen with an antibody directed against mouse angiostatin. Moreover, the endostatin antibody was specific to mouse and human endostatin and did not shown any cross-reactivity to human and mouse angiostatin, demonstrating specificity to endostatin.

Example 16
Effect of Endostatin on Endothelial Cell Proliferation

The ability of human endostatin to inhibit the proliferation of C-PAE cells was tested using $^3$H-thymidine incorporation as described for mouse endostatin by Dhanabal et al. (1999) (*Biochem. Biophys. Res. Commun.* 258:345–52), and in PCT/US98/26057, "Mutants of Endostatin, 'EM1' Having Anti-Angiogenic Activity and Methods of Use Thereof" by Vikas P. Sukhatme, filed Dec. 8, 1998, and in U.S. Ser. No. 09/589,777, "Anti-Angiogenic Peptides and Methods of Use Thereof", by Vikas P. Sukhatme, filed Jun. 8, 2000 the entire teachings of both of which are incorporated herein by reference. Subsequently, HUVE and HMVE-L cells were used to evaluate the anti-proliferative effect of human endostatin. Human endothelial cells were seeded at $2\times10^4$ in 1% FCS cells per well in a 24-well plate coated with fibronectin (10 micrograms/ml). The cells were stimulated with bFGF (3 ng/ml), with different concentrations of human endostatin added at the same time. The cells were incubated at 37° C. for 24 hours, followed by a $^3$H-thymidine pulse of 1 micro Ci for 24 hours. Medium was aspirated, cells washed three times with PBS, and then solubilized by addition of 1.5 N NaOh (100 microliters/well) and incubated at 37° C. for 30 minutes. Cell-associated radioactivity was measured with a scintillation counter.

Human endostatin showed no inhibitory effect in C-PAE cells, whereas mouse endostatin showed a dose-dependent inhibition of these same cells. Human endothelial cells (HUE and HMVE-L) were then used, and FIGS. 13A and 13B show the dose dependent inhibition of bFGF-induced proliferation in the presence of mouse and human endostatin. For both types of cells, bFGF at 3 ng/ml was used as a stimulus. Each value is a mean of triplicate cultures from a representative experiment and error bars represent standard deviations. DNA synthesis in the control culture was considered as 100%. Shaded and light bars represent mouse and human endostatin, respectively.

Mouse endostatin was less potent than human endostatin under these conditions. At 10 micrograms/ml, human endostatin inhibited 40% and 36% of $^3$H-thymidine incorporation in HUVE and HMVE-L cells, respectively. The calculated $ED_{50}$ value for human endostatin in these cells was in the range of 5.0 to 7.5 micrograms/ml. The recombinant human endostatin did not inhibit the proliferation of the human 786-0 renal cell carcinoma cells or of the human WI–38 fibroblasts at concentrations ranging from 0.5 micrograms/ml to 10 micrograms/ml.

Example 17
Cell Cycle Analysis

HUVE and HMVE-L cells were growth arrested by contact inhibition for 48 hours in complete medium. The cells were harvested by trypsinization and seeded into a 6-well plate coated with fibronectin (10 micrograms/ml). Each well was seeded with $0.2\times10^6$ cells in 1% FCS supplemented with 3 ng/ml of bFGF. For the dose-response study, different concentrations of human endostatin were added and the cells harvested at 24 hours after treatment. The cells were washed in PBS buffer and fixed in 70% ice cold ethanol. The fixed cells were rehydrated at room temperature for 30 minutes in PBS buffer containing 2% FCS and 0.1% Tween-20, centrifuged at 1500×g for 10 minutes and resuspended in 0.5 ml of the above buffer to which RNase (5 micrograms/ml) was added. RNase digestion was carried at 37° C. for 1 hour, followed by staining with propidium iodide (5 micrograms/ml). The cells were analyzed using a Becton Dickinson FACStar Plus flow cytometer (Becton Dickinson, Waltham, Mass., USA). For calculating the percentage of cells in different phases of the cell cycle, the ModFit software was used. For the time course study, 10 micrograms/ml of human endostatin was added and cells were harvested at different time points (15, 18, 24 and 32 hours). For testing the specificity of human endostatin, the non-endothelial fibroblast cell lines IMR-90 and WI-38 were used in the cell cycle analysis.

Figure 16A:
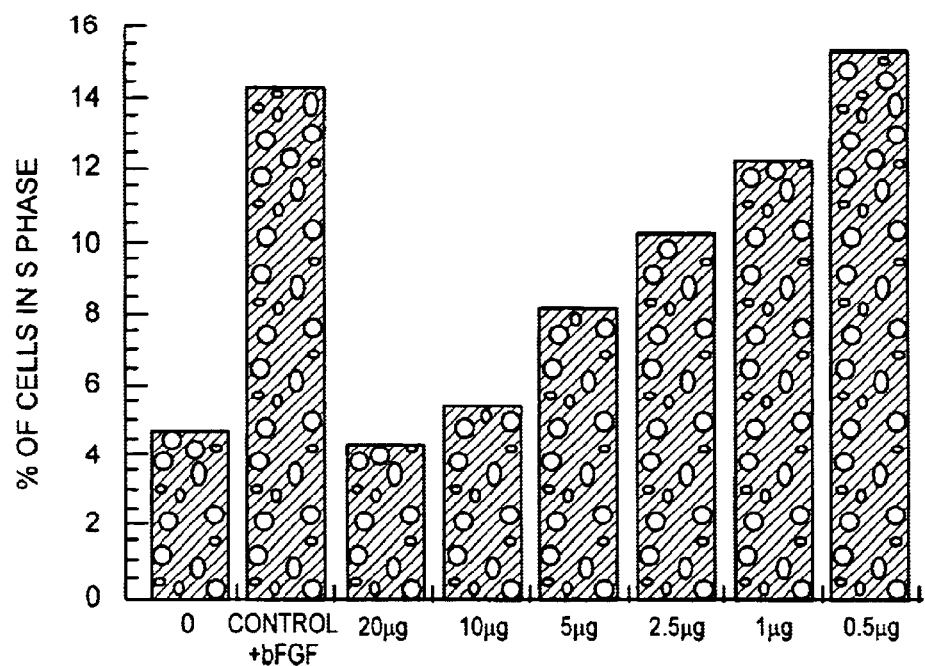
FIG. 16A shows human endostatin treatment of HUVE cells specifically affects cells in S phase. Growth arrested HUVE cells were treated with different concentrations of human endostatin ranging from 0.5 micrograms/ml to 20 micrograms/ml. The cells were grown in 1% FCS and stimulated with 3 ng/ml of bFGF.
Figure 16B:
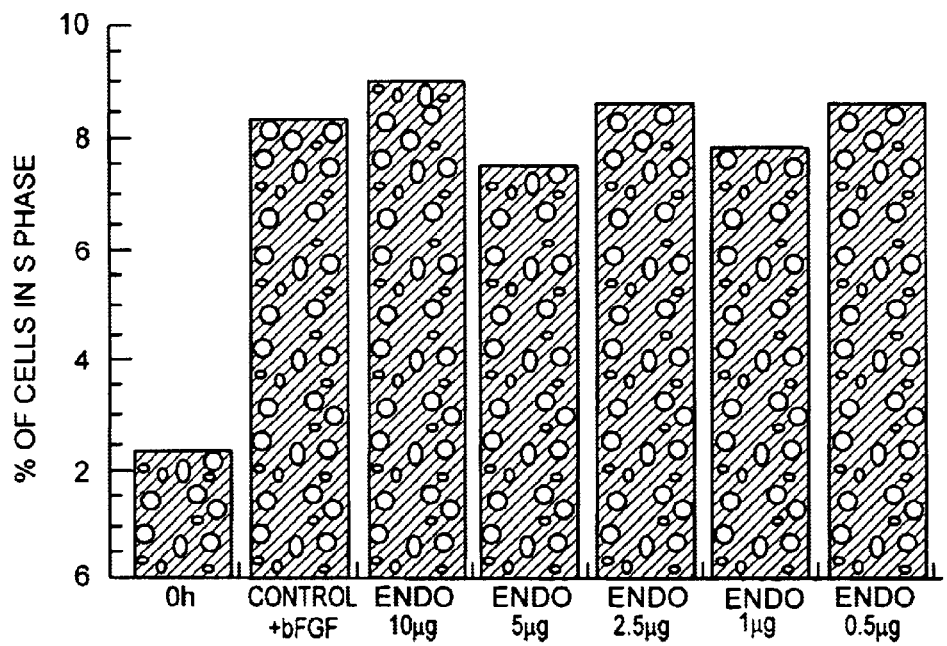
FIGS. 16B and 16C show non-endothelial IMR-90 (B) and Wi-38 (C) cells were treated with 10 micrograms/ml of human endostatin and processed as described herein.
Figure 16C:
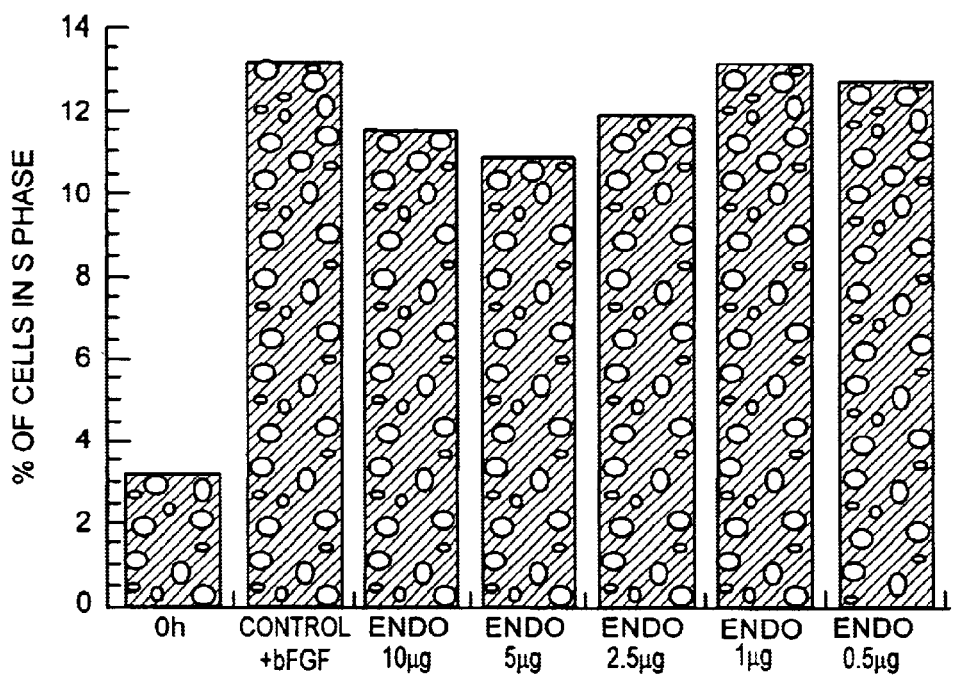

At time 0 hours, 4.5% of the "growth arrested" contact-inhibited cells were in S phase (FIG. 16A). When the cells were stimulated with bFGF (3 ng/ml) alone for 24 hours, there was a 3.5-fold increase in the percentage of cells in S phase. Upon treatment with 20 g/ml of endostatin, the percentage of cells in S phase was reduced to baseline. A dose-dependent inhibition was seen with increasing concentrations of endostatin (0.5 g/ml to 20 g/ml). In non-endothelial cells (IMR-90 and WI-38) treated with human endostatin, the percentage of cells in S phase was unaffected (FIGS. 16B and 16C).

Figure 16D:
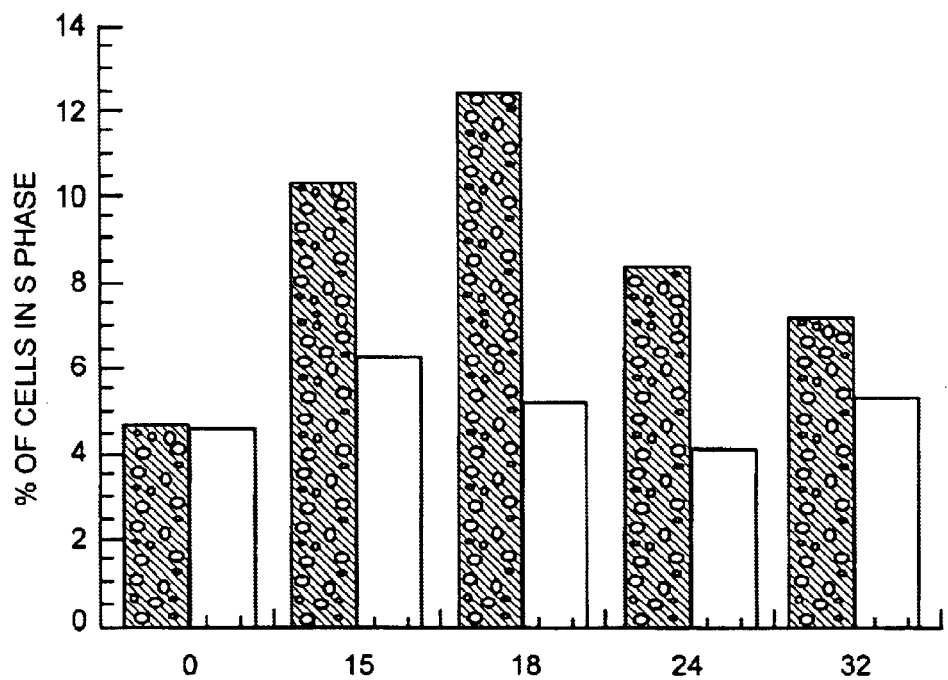
FIG. 16D shows HUVE cells were treated with 10 micrograms/ml of human endostatin and harvested at 15, 18, 24 and 32 h after treatment.

In order to determine the earliest time point at which endostatin exerts its inhibitory effect on endothelial cells, a time course study with 10 micrograms/ml of human endostatin was conducted. FIG. 16D shows the time course effect of human endostatin, and indicates that the effect of human endostatin can be seen as early as 15 hours after treatment in HUVE cells.

Example 18
Endothelial Cell Tube Formation in Matrigel®

24-well tissue culture plates were coated with 0.5 ml of MATRIGEL® complete (Collaborative Biomedical Products, Bedford, Mass., USA). The plate was incubated at 37° C. for one hour (Gately et al. (1996) *Cancer Res.* 56:4887–90). ECV304 cells at a concentration of $5\times10^4$ in 0.5 ml of M199 medium were added to the top of the gel followed by different concentrations of recombinant human endostatin. The cultures were incubated for 8 to 10 hours at 37° C. in a 5% $CO_2$ humidified atmosphere. A representative area of the tube network was photographed using a Nikon camera at final magnification of 200×.

Endothelial cell tube formation was significantly inhibited with endostatin treatment at 10 micrograms/ml. In the control cells, tube formation was continuous and formed a distinct, continuous, hexagonal structure without significant interruption. In contrast, the mean diameter of endostatin-treated tubes was smaller and was marked by frequent interruptions, indicating the effect of human endostatin on endothelial cell tube formation.

Example 19
Annexin V-FITC Assay

After initiation of apoptosis, most cell types translocate the membrane phospholipid phosphatidylserine (PS) from the inner surface of the plasma membrane to the outside (van Engeland et al. (1998) *Cytometry* 31:1–9; Zhang et al. (1997) *Biotechniques* 23:525–31; Koopman et al. (1994) *Blood* 84: 1415–20). PS, and therefore apoptosis, can be detected by staining with an FITC conjugate of Annexin V, a calcium-dependent phospholipid binding protein of 38 kDa that has a high affinity for PS. PS can generally be detected prior to bleb formation and DNA fragmentation.

Briefly, 200,000 cells were plated onto a fibronectin-coated 6-well plate in EGM medium containing 1% FCS and 3 ng/ml bFGF. Different concentrations of human and mouse endostatin were added to the wells, and cells were harvested and processed 18 hours after treatment. Human recombinant TNF-alpha (40 ng/ml) was used as a positive control. The cells were washed in PBS and resuspended in binding buffer (10 mM HEPES/NaOH, pH 7.4, 140 mM NaCl, 2.5 mM $CaCl_2$). Annexin V-FITC was added to a final concentration of 100 ng/ml, and the cells were incubated in the dark for 10 minutes, then washed again in PBS and resuspended in 300 ml of binding buffer. 10 microliters of propidium iodide (PI) was added to each sample prior to flow cytometric analysis. Data analysis was performed with the standard Cell Quest software (Becton-Dickinson, Waltham, Mass., USA). The quadrant settings were set so that the negative control allowed less than 1% positivity. Non-endothelial cells IMR-90 and WI-38, were treated with human endostatin (10 micrograms/ml) and processed as described above.

Endostatin at 10 micrograms/ml showed a distinct shift in Annexin fluorescence intensity with a more pronounced effect noted in the HMEV-L cells. The mean fluorescence intensity difference between control and treated cells was significant (p=0.01) at 10 micrograms/ml of endostatin. The shift in fluorescence intensity was similar for endostatin at 10 micrograms/ml and the positive control TNF-alpha (40 ng/ml). Concentrations of endostatin below 1 microgram/ml did not show any significant Annexin V positivity. Interesting, mouse endostatin did not show any increase in Annexin positivity in these cells, but in C-PAE and BAE cells, it showed comparable fluorescence staining as that seen in HUVE cells in the presence of human endostatin (Dhanabal et al. (1999) *J. Biol. Chem.* 274:11721–6). With regard to non-endothelial cells IMR-90 and WI-38, no annexin positivity was seen. Based on these results, endostatin action appears to be selective for endothelial cells. Similar data have been obtained with mouse endostatin in C-PAE cells (Dhanabal et al. (1999) *J Biol. Chem.* 274:11721–6).

Example 20
Cell Migration Assay

Previous experiments showed that C-PAE cells did not migrate in response to bFGF and VEGF, so ECV304 cells were used to assess the ability of human endostatin to block bFGF mediated migration. The migration assay was performed using a 12-well Boyden chemotaxis chamber (Neuro-probe, Inc., Cabin John, Mich.) with a polycarbonate membrane (25×80 mm, PVD free, 8 pores, Poretics Corp., Livermore, Calif., USA). The non-specific binding of growth factor to the chambers was prevented by coating the chambers with a solution containing 0.5% gelatin, 1 mM $CaCl_2$, and 150 mM NaCl at 37° C. overnight. ECV304 cells were grown in 10% FBS containing 5 ng/ml Dil (1, 1'-dioctadecyl-3,3,3',3'-tetramethylindocarbocyanine perchlorate DiIC 18, Molecular Probes, Eugene, Oreg., USA) overnight and washed with PBS containing 0.5% BSA. Following trysinization, the cells were counted using a Coulter-Counter Z1, (Luton, U.K.), and diluted to 300,000 cells/ml in Medium 199 containing 0.5% FBS. The lower chamber was filled with Medium 199 containing 25 ng/ml bDFD. The upper chamber was seeded with 15,000 cells/ well with different concentrations of recombinant endostatin. Cells were allowed to migrate for 4 hours at 37° C. The cells on the upper surface of the membrane were then removed with a cell scraper and the (migrated) cells on the lower surface were fixed in 3% formaldehyde and washed with PBS. Images of the fixed membrane were obtained using fluorescence microscopy at 550 nM with a digital camera and the number of cells on each membrane was determined using the OPTIMAS v.6.0 software. Each treatment was done in duplicate, and recombinant mouse endostatin was used as a positive control.

Figure 17:
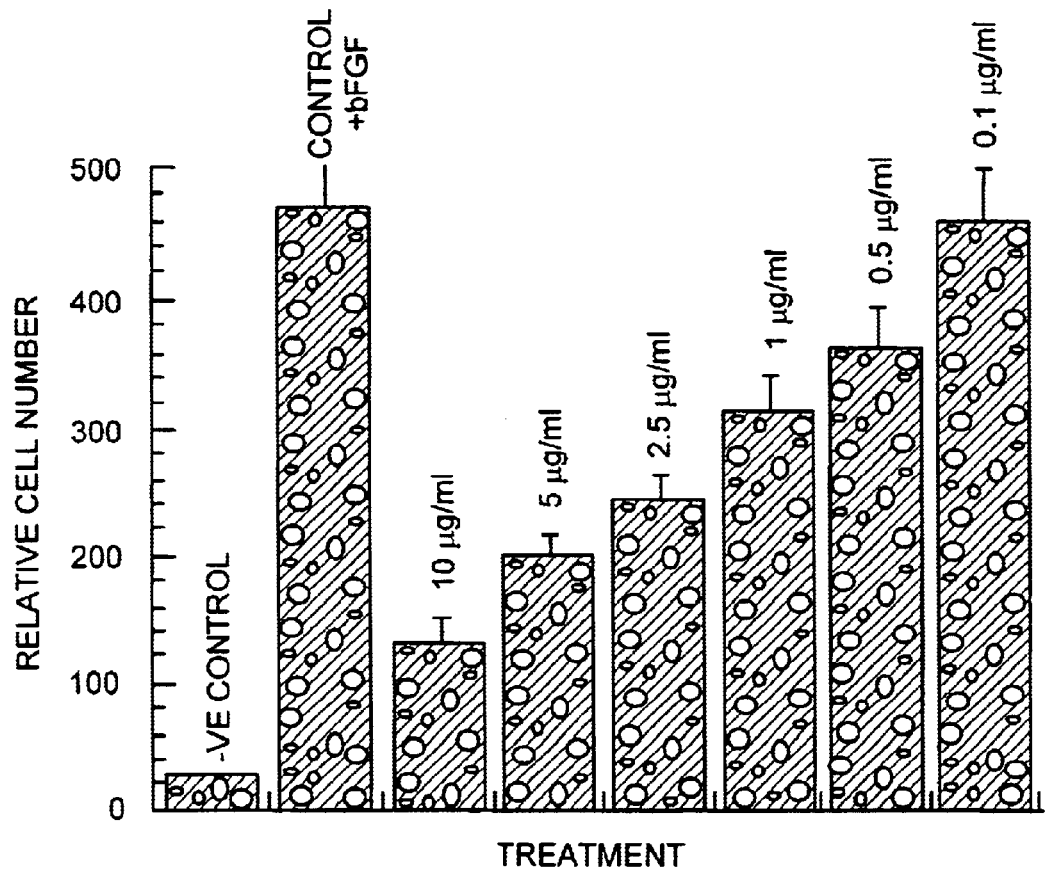
FIG. 17 is a bar graph showing the inhibition of endothelial cell migration resulting from exposure to different concentrations of endostatin. Treatments (control, control+ bFGF, and endostatin at 10, 5, 2.5, 1, 0.5, and 0.1 micrograms/ml) are displayed along the x-axis, and the y-axis shows the cell number relative to representative experiments. Each value is a mean from representative experiments and error bars represent standard deviations.

A dose-dependent inhibition of migration was observed. In each well, the number of cells migrated was counted in three different areas and the average obtained. The results are shown in FIG. 17, which is a bar graph. Each value is a mean from representative experiments and error bars represent standard deviations. Significant levels of inhibition were seen at 10 micrograms/ml and 5 micrograms/ml. At concentrations of less than 0.1 micrograms/ml, only marginal inhibition of migration was observed. HUVE cells were then tested under identical conditions which also showed a comparable response profile. In the case of HUVE cells, the cells were allowed to migrate for 16 to 20 hours.

Example 21
Elisa Titer Determination for Angiostatin 96-well plates were coated with 10 micrograms/ml purified angiostatin antigen, incubated at room temperature for 1 hour, and washed three times with phosphate buffered saline/0.05% TWEEN 20. The plates were then blocked for 1 hour at room temperature with 5% milk powder and 0.01% BSA, then washed three times with PBS/0.05% TWEEN 20. Different dilutions of test bleed antisera were diluted tenfold, and added to triplicate wells, then incubated for 1 hour at room temperature. They were then washed three times with PBS/0.05% TWEEN 20, and secondary antibody added (anti-rabbit IgG/alkaline phosphatase), and incubated at room temperature for 1 hour, then washed three times. Phosphatase substrate was added, and incubated for 20–30 minutes, and the absorbance read at 405 nM. Mouse and human angiostatin showed roughly equivalent results.

Example 22
Effect of Angiostatin in the Endothelial Cell Proliferation Assay

Figure 18A:
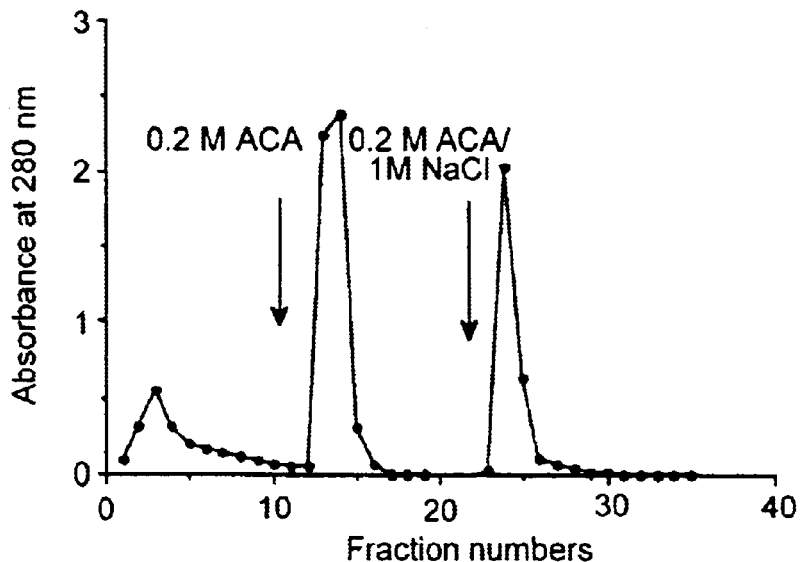
FIGS. 18A–B show the results of the purification of mouse angiostatin on a lysine Sepharose 4B column.
Figure 18B:
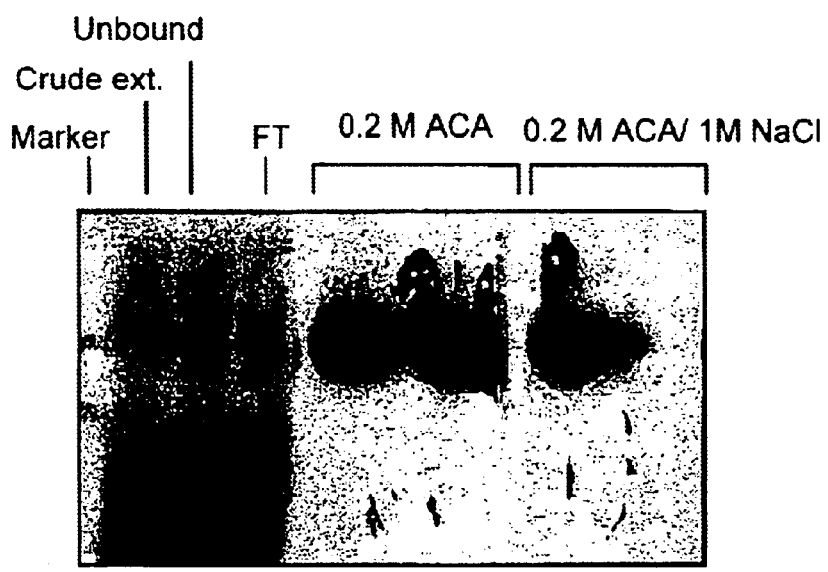
Figure 19:
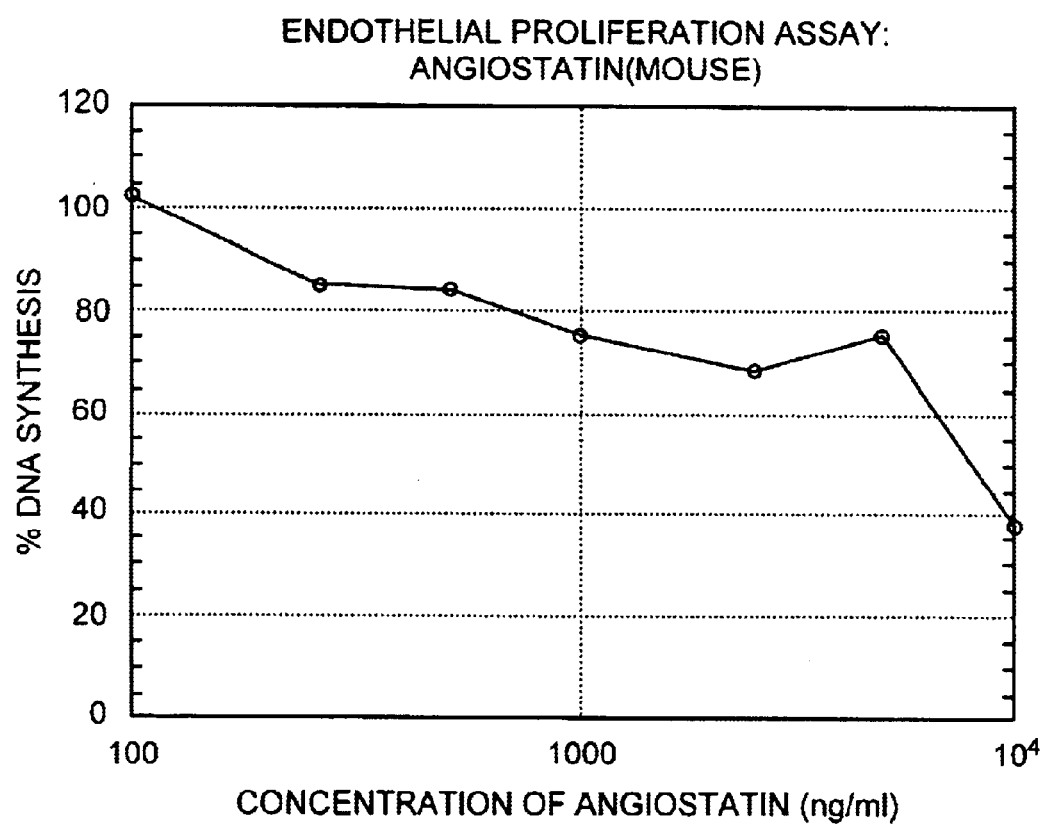
FIG. 19 shows the results of the endothelial proliferation assay using mouse angiostatin.

Mouse angiostatin was produced as described herein (see FIGS. 18A and 18B). The crude supernatant containing recombinant angiostatin protein was concentrated by ammonium sulfate precipitation (70%). The precipitated protein was dissolved in 50 mM sodium phosphate buffer, pH 7.4 and dialyzed overnight at 4° C. (three changes at 6–8 hour intervals). The dialyzed sample was further concentrated by ultra-filtration using an Amicon concentrator (YM 10). A Bio-Rad column was packed with Lysine-Sepharose 4B resin (Pharmacia, New Jersey) and equilibrated with 50 mM sodium phosphate buffer, pH 7.4. The concentrated sample was loaded on the column using a peristaltic pump. The column was washed with equilibration buffer until the $A_{280}$ was <0.001. The column was again washed with 10 column volumes of sodium phosphate buffer, pH7.4 containing 200 mM NaCl. Recombinant angiostatin protein was eluted with 0.2 m ε-amino-N-caproic acid, pH 7.4. Fractions containing significant amount of protein as measured by absorbance and SDS-PAGE analysis were pooled and dialyzed against PBS, pH 7.4 for 24–36 h. Protein concentration was measured by the BCA assay (Pierce). All the purification process was performed in the cold room (4° C.). The recombinant protein was further purified by size separation on FPLC using Superdex-75 column.

Figure 20:
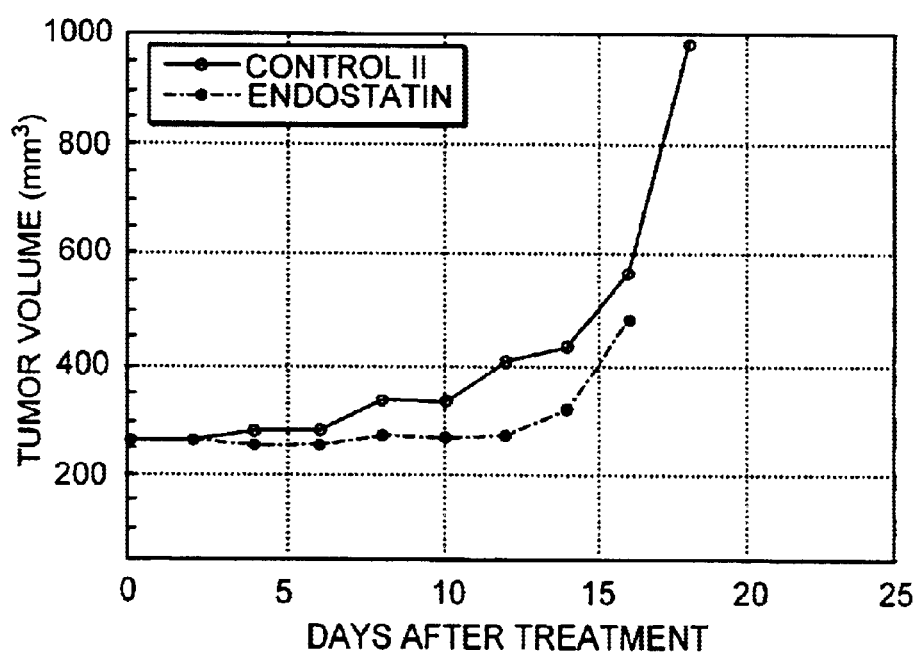
FIG. 20 is a graph showing the effect of recombinant mouse angiostatin on growth of renal cancer cell line 786-0. Time (days after treatment) is shown on the x-axis, and the rumor volume on the y-asix. Growth of control tumors (dashed line, ●) showed increased growth relative to tumors treated with recombinant mouse angiostatin (solid line, ○).

C-PAE cells were seeded at 12,500 per well on a gelatin-coated plate in low serum. Cells were allowed to adhere overnight at 37° C. Spent medium was removed and new low serum medium containing 3 ng/ml of bFGF was added. Different dilutions of purified recombinant angiostatin was added, and incubated at 37° C. for 48 hours. The cells were then pulse-labeled with $^3$H-thymidine (I microCi/20 microliters/well) for 24 hours. They were then harvested, and the incorporation of thymidine was measured. Results are shown in FIG. 20, which is a graph showing DNA synthesis is shown on the y-axis, and concentration of angiostatin on the x-axis. DNA synthesis generally dropped with increasing concentrations of angiostatin.

Example 23
Effect of Angiostatin in a Renak Tumor Model

Athymic nude mice were transplanted subcutaneously with renal tumor cell line 786-0. Approximately 5 million cells in 200 ml of phosphate buffered saline were inoculated in the flank of each mouse. Each tumor was allowed to reach approximately 200 cubic millimeters.

About 20 micrograms of purified recombinant mouse angiostatin (1 mg/kg) was given to each animal intraperitoneally on a daily basis for 3 weeks.

Example 24
Expression of Angiostatin in the Pichia Expression System

The mouse angiostatin cDNA clone and its sequence were provided by the ATCC (American Type Culture Collection, 10801 University Blvd., Manassas, Va., USA) clone MPL8-2000 (plasminigen encoding plasmid). Two primers were made from this sequence: 5'-AAG AAT TCG TGT TGT ATC TGT CAG AAT GT-3' (SEQ ID NO;31) and 5'-AGC GGC CGC CTA CCC TCC TGT CTC TGA-3' (SEQ ID NO:32).

The human angiostatin cDNA clone and its sequence were provided by the ATCC (American Type Culture Collection), clone PKSK067. Two primers were made from this sequence: 5'-AAG AAT TCG TGT ATC TCT CAG AGT GC-3' (SEQ ID NO:33), and 5'-AGC GGC CGC CTA TTC TGT TCC TGA GTA-3' (SEQ ID NO:34).

Figure 21A:
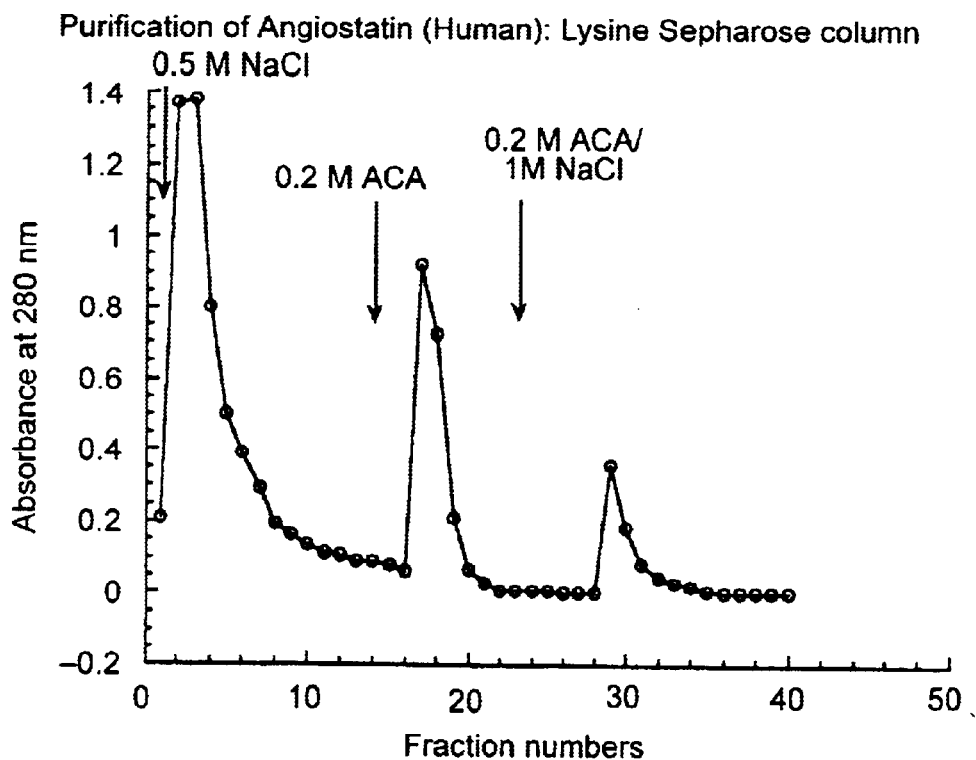
FIGS. 21A–B show the purification of human angiostatin on a lysine Sepharose column.
Figure 21B:
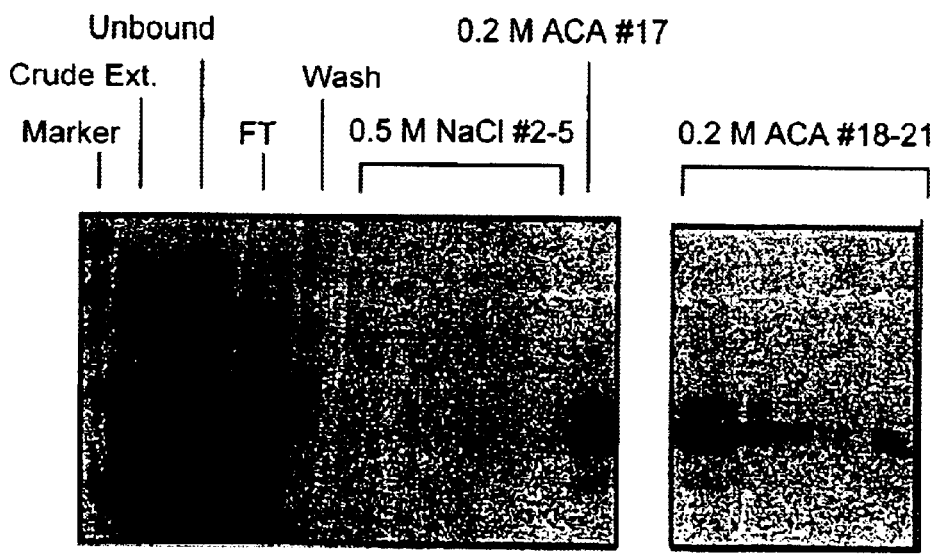

Cloning and expression of both angiostatins in the modified Pichia yeast expression system were done as described herein (see FIGS. 21A–B).

Example 25
Restin

Isolation of carboxy terminal portion of Collagen XV:
The following CDNA libraries were used as template for DNA-PCR.

K562—erthyroid library
JMN—human mesothiolioma
HFK—human fetal kidney library
786-0—human renal cell carcinoma
MAB—human adult brain
293—control Primers corresponding to "C" terminal portion of Collagen XV NC-1 domain (FIG. 22, and the amino acid sequence of Restin is shown in FIG. 23) were synthesized from GIBCO-BRL.

Upstream Primer

TTT TTT GAA TTC ATT TCA AGT GCC AAT TAT GAG AAG
    CCT GCT CTG CAT TTG                    (SEQ ID NO:21)

Downstream Primer

AAG AAT GCG GCC GCT TAC TTC CTA GCG TCT GTC ATG
    AAA CTG TTT TCG AT                     (SEQ ID NO:22)

DNA-PCR was carried out using standard protocols. Briefly, 100 ng of DNA from each cDNA library was used as template. The amplification conditions were 94° C.×1 min., 65° C.×1 min., and 72° C.×40 seconds for 30 cycles.

Figure 24:
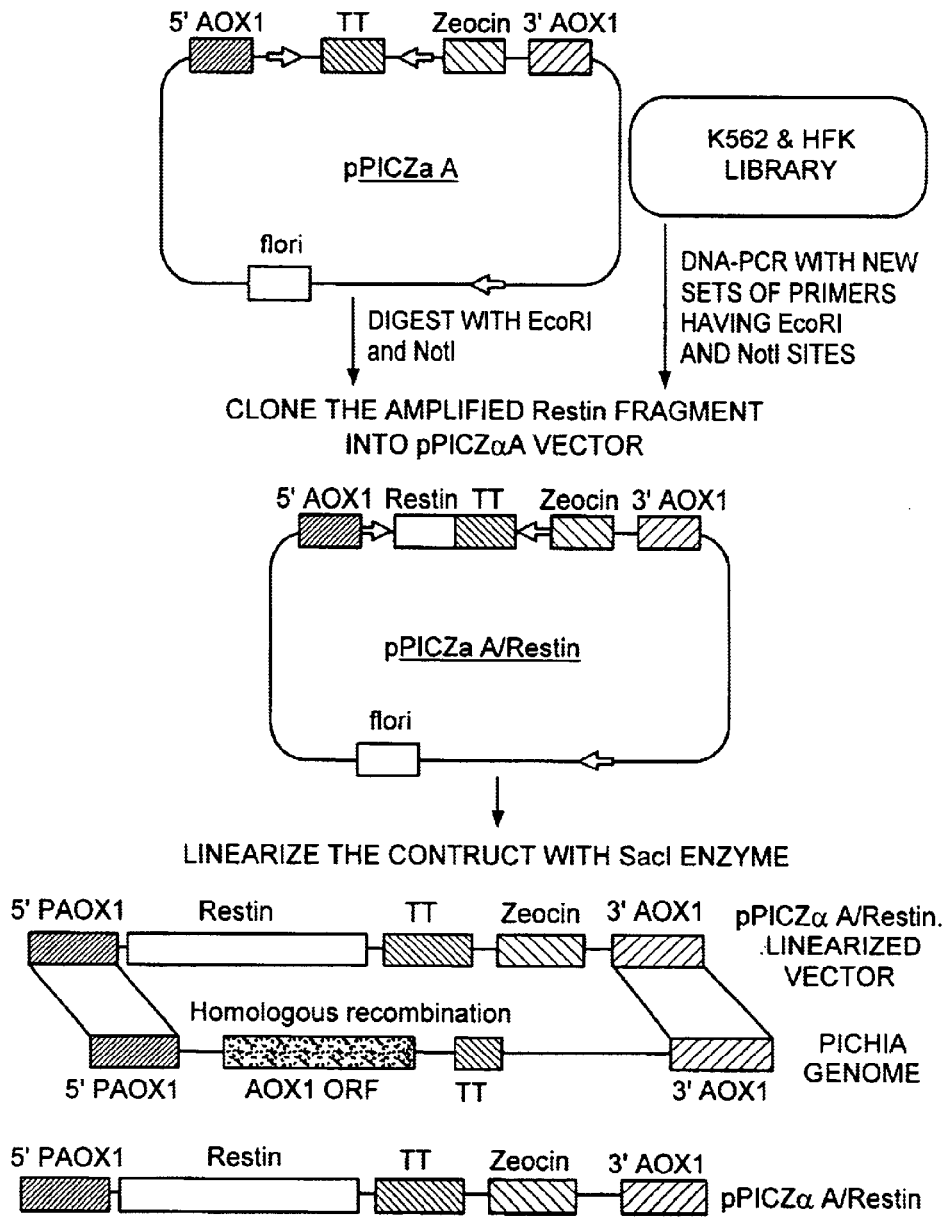
FIG. 24 is a schematic representation of the cloning of restin into the Pichia expression system.

The 540 bp amplified fragment, hereafter named "RESTIN," was purified and digested with EcoRI and NotI. Cloning of Collagen XV into the Pichia expression vector (pPICZαA, commercially available from In Vitrogen, San Diego, Calif.) is shown schematically FIG. 24. Constructs, vectors, etc. are shown in FIG. 25. The vector pPICZαA was also digested with the above restriction enzymes and ligated with the Restin fragment. Initial transformation was carried out with the host strain Top 10F'. Positive clones were sequenced to confirm the modification. The plasmid was then linearised with SacI enzyme and used for homologous recombination into the yeast host strain GS 115 via lithium chloride transformation. The recombination was carried out as described in the Pichia expression manual. The colonies were allowed to grow for two days at 30° C. on YPD/Zeocin plates. Clones which grew on Zeocin were selected for small scale induction. The induction procedure was carried out as suggested by the manufacturer (InVitrogen, San Diego, Calif., USA).

Expression of Restin in Pichia Expression System

A single colony was inoculated from YPD/Zeocin into 25 ml of BMGY/Zeo (100 ug/ml) in a 500 ml baffled flask. The culture was grown at 30° C. in a shaking incubator (250 rpm) until the culture reached an $OD_{600}$ of 2–6 (approximately 16–24 hours). The cells in the log phase of growth were used in a 1:100 dilution to inoculate a 1-liter culture. 500 ml of BMGY medium was added, and the cells were grown in a 2-liter baffled flask and the culture reached an $OD_{600}$ of 15–20 (2–3 days). The cells were harvested by centrifugation at 5000 rpm for 10 minutes at room temperature. The supernatant was decanted, and the cell pellet resuspended in 300–400 ml of BMMY medium to induce expression of the recombinant protein. To maintain induction, 100% methanol was added to a final concentration of 0.5% every 24 hours. Supernatant was collected on the second, third, and fourth days after induction, and analyzed for protein expression by Coomassie stained SDS-PAGE.

Purification of Restin using Heparin-Sepharose Column

The supernatant was concentrated by precipitation with 60–70% ammonium sulfate. The precipitated protein was centrifuged at 10,000 rpm for 10 min and the pellet was resuspended in phosphate-buffered saline and dialyzed overnight at 4° C. The final dialysis was done with 10 mM Tris and 50 mM NaCl, pH 7.4. A polyprep column was packed with 5 ml of Heparin-Sepharose (Pharmacia Biotech, Inc. Piscatawy, N.J., USA) resin and equilibrated with 10 mM Tris, 50 MM NaCl, pH 7.4. The concentrated crude protein sample was loaded in 20–30 ml batches onto the column at a flow rate of 10–15 ml/hour. The column was washed with equilibration buffer until the absorbance at 280 nm was<0.001. The elution of bound proteins was carried by step-wise gradients of NaCl (0.2M, 0.6M and 1.0 M). The elution profile failed to show any distinct protein peak, and when the samples were analyzed by SDS-PAGE, a majority of the protein did not bind to the column. Lowering the sodium chloride concentration and changing the pH did not change the binding profile. The recombinant protein did not bind to the heparin column. Hence we decided to add His.Tag motif to the Restin molecule at the amino terminus to simplify purification.

Construction of HIS.TAG Restin Recombinant Protein

Two complementary oligonucleotides were synthesized coding for histidine residues (six histidine residue at stretch), flanked by the EcoRI restriction site. The vector pPICZαA was digested with EcoRI. Fifty microliters of each primer (100 microM) was mixed and denatured at 95° C. for 5 min. and cooled immediately on ice. The annealed primer was ligated into EcoRI digested vector backbone at 16° C. overnight. The ligase was heat-inactivated at 70° C. for 10 min. and the excess primer was removed using Glass Max purification column. The ligated vector was transformed using the host strain Top 10F'. The recombinant clones were screened by PCR and restriction enzyme analysis. The presence of His.Tag motif was further confirmed by sequencing.

The recombinant pPICZαA/His.Restin was linearized with SacI and recombination was carried out using the strain GS115 using standard protocols.

Figure 26:
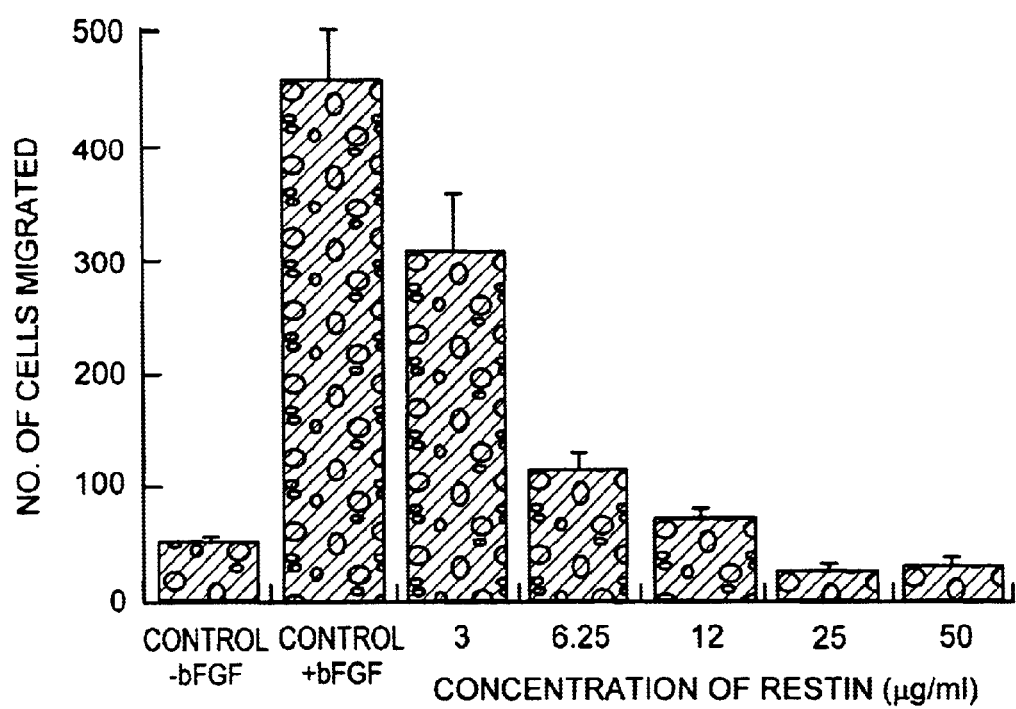
FIG. 26 shows the results of the effects of restin in a migration assay.
Figure 27:
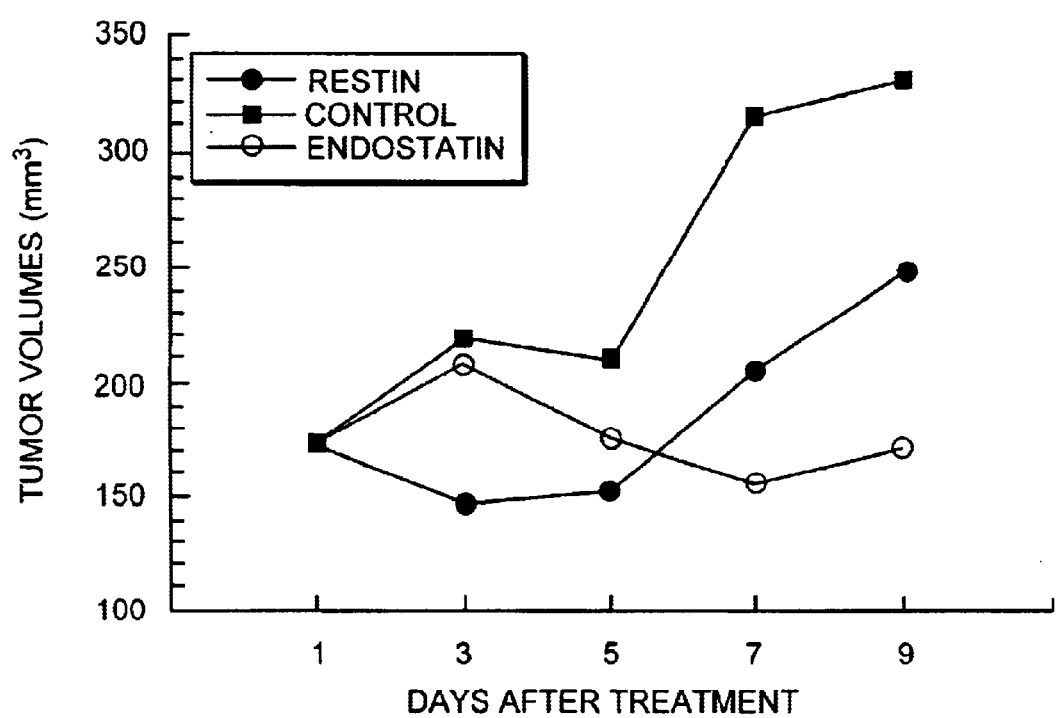
FIG. 27 shows the results of the effects of restin in tumor growth. Restin and endostatin were used at a concentration of 10 mg/kg.

The biological activity of restin was evaluated in the assays described herein. FIG. 26 shows the activity of restin in the cell migration assay described elsewhere herein, and FIG. 27 shows the activity of restin in the tumor assay describe elsewhere herein.

The fragment of restin, Apomigren can also be produced as restin was produced as described herein and its biological activity evaluated using the methods described.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of producing a biologically active anti-angiogenic protein, comprising:
   (a) inserting an isolated polynucleotide sequence encoding a biologically active anti-angiogenic restin protein into a yeast expression vector, wherein the vector contains a multiple cloning site; and
   (b) transforming an appropriate yeast strain with the vector of step (a) and maintaining the yeast strain under suitable conditions for the production of the biologically active anti-angiogenic restin protein;
thereby producing a biologically active anti-angiogenic restin protein.

2. The method of claim 1 wherein the yeast strain is *Pichia pastoris*.

3. The method of claim 1 wherein the expression vector comprises the pPICZαA vector.

4. The method of claim 1 wherein the biological activity is evaluated by one or more of the following assays: endothelial cell migration, inhibition of tumor growth in a mammal, arrest of endothelial cells in $G_1$ phase of the cell cycle, and induction of apoptosis in endothelial cells.

5. The method of claim 1 wherein the biologically active anti-angiogenic restin protein, or biologically active anti-angiogenic mutant, fragment or fusion protein thereof is produced at a concentration of 10–20 milligrams or more per liter of culture fluid.

6. The method of claim 1 wherein the isolated polynucleotide of step (a) additionally comprises a polynucleotide linker, and the biologically active anti-angiogenic restin protein produced in step (b) additionally comprises at least one amino acid residue resulting from the polynucleotide linker.

7. The method of claim 6 wherein the biologically active anti-angiogenic restin protein comprises two additional amino-terminus amino acid residues.

8. The method of claim 1 wherein the vector of step (a) comprises a pPICzαA plasmid wherein the plasmid contains a multiple cloning site, said cloning site comprising a His.Tag motif and wherein the biologically active anti-angiogenic restin protein produced in step (b) comprises a histidine tag motif.

9. The method of claim 8 wherein the yeast strain is *Pichia pastoris*.

10. The method of claim 8 wherein the biological activity is evaluated by one, or more of the following assays: endothelial cell migration; inhibition of tumor growth in a mammals; arrest of endothelial cells in $G_1$ phase of the cell cycle; or induction of apoptosis in endothelial cells.

11. The method of claim 8 wherein the biologically active anti-angiogenic restin protein is produced at a concentration of 10–20 milligrams or more per liter of culture fluid.

12. A method of producing a biologically active anti-angiogenic restin protein comprising:
   (a) inserting an isolated polynucleotide sequence encoding a biologically active anti-angiogenic restin protein wherein the polynucleotide additionally comprises a linker, wherein the polynucleotide linker encodes at least one amino acid, into a yeast expression vector comprising a pPICzαA plasmid wherein the plasmid contains a multiple cloning site; and
   (b) transforming a *Pichia pastoris* yeast strain with the vector of step (a) and maintaining the yeast strain under suitable conditions for the production of the biologically active anti-angiogenic restin protein, comprising at least one amino acid residue resulting from the linker polynucleotide;
thereby producing a biologically active anti-angiogenic restin protein.

13. The method of claim 12 wherein the polynucleotide additionally encodes angiostatin, endostatin, or mutants, fragments or fusion proteins thereof.

14. A method of producing a biologically active anti-angiogenic protein, comprising:
   (a) inserting an isolated polynucleotide sequence encoding a biologically active anti-angiogenic restin protein, wherein the polynucleotide additionally comprises a linker and wherein the polynucleotide linker encodes at least one amino acid, into a least expression vector comprising a pPICzαA plasmid wherein the plasmid contains a multiple cloning site and wherein the cloning site additionally comprises a histidine tag motif; and
   (b) transforming a *Pichia pastoris* yeast strain with the vector of step (a) and maintaining the yeast strain under suitable conditions for the production of the biologically active anti-angiogenic restin protein comprising at least one amino acid residue resulting from the linker polynucleotide, and wherein the protein additionally comprises a histidine tag motif;
thereby producing a biologically active anti-angiogenic restin protein.

15. The method of claim 4 wherein the polynucleotide additionally encodes endostatin, angiostatin, or mutants, fragments or fusion proteins thereof.

16. A method of producing a biologically active anti-angiogenic apomigren polypeptide, comprising:
   (a) inserting an isolated polynucleotide sequence encoding a biologically active anti-angiogenic apomigren polypeptide into a yeast expression vector, wherein the vector contains a multiple cloning site; and
   (b) transforming an appropriate yeast strain with the vector of step (a) and maintaining the yeast strain under suitable conditions for the production of the biologically active anti-angiogenic apomigren polypeptide; thereby producing a biologically active anti-angiogenic apomigren polypeptide.

17. The method of claim 16, wherein the isolated polynucleotide of step (a) additionally comprises a polynucleotide linker, and the biologically active anti-angiogenic apomigren polypeptide produced in step (b) additionally comprises at least one amino acid residue resulting from the polynucleotide linker.

18. The method of claim 16, wherein the biologically active anti-angiogenic apomigren polypeptide comprises two additional amino-terminus amino acid residues.

19. The method of claim 16, wherein the vector of step (a) comprises a pPICzαA plasmid wherein the plasmid contains a multiple cloning site, said cloning site comprising a His.Tag motif and wherein the biologically active anti-angiogenic apomigren polypeptide produced in step (b) comprises a histidine tag motif.

20. The method of claim 16, wherein the biologically active anti-angiogenic apomigren polypeptide comprises amino acids 97–181 of SEQ ID NO:20.

21. The method of claim 16, wherein the yeast strain is *Pichia pastoris*.

* * * * *